US008841421B2

(12) United States Patent
Bjork et al.

(10) Patent No.: US 8,841,421 B2
(45) Date of Patent: Sep. 23, 2014

(54) S100A9 INTERACTION SCREENING METHOD

(75) Inventors: Per Bjork, Lund (SE); Frederik Ivars, Lund (SE); Tomas Leanderson, Lund (SE)

(73) Assignee: Active Biotech, AB, Lund (SE)

( * ) Notice: Subject to any disclaimer, the term of this patent is extended or adjusted under 35 U.S.C. 154(b) by 907 days.

(21) Appl. No.: 12/597,735

(22) PCT Filed: Apr. 24, 2008

(86) PCT No.: PCT/EP2008/003303
§ 371 (c)(1),
(2), (4) Date: Mar. 3, 2010

(87) PCT Pub. No.: WO2008/131908
PCT Pub. Date: Nov. 6, 2008

(65) Prior Publication Data
US 2010/0166775 A1    Jul. 1, 2010

Related U.S. Application Data

(60) Provisional application No. 60/914,180, filed on Apr. 26, 2007, provisional application No. 61/021,961, filed on Jan. 18, 2008.

(30) Foreign Application Priority Data

Apr. 26, 2007 (EP) .................................... 07251762
Jan. 21, 2008 (GB) .................................... 0801084.5

(51) Int. Cl.
C07K 16/18 (2006.01)
C07K 14/52 (2006.01)
G01N 33/566 (2006.01)
G01N 33/68 (2006.01)
C07K 14/705 (2006.01)

(52) U.S. Cl.
CPC ................ C07K 14/52 (2013.01); C07K 16/18 (2013.01); *C07K 2316/96* (2013.01); G01N 33/566 (2013.01); G01N 33/6842 (2013.01); *G01N 2500/00* (2013.01); *G01N 2333/70503* (2013.01); *G01N 2333/705* (2013.01); C07K 14/705 (2013.01); *C07K 2317/56* (2013.01)
USPC ..................................... 530/388.1; 530/388.8

(58) Field of Classification Search
None
See application file for complete search history.

(56) References Cited

U.S. PATENT DOCUMENTS

2006/0140933 A1   6/2006 Pittman et al.
2007/0253950 A1   11/2007 Jacobsen
2007/0286858 A1 * 12/2007 Clancy et al. .............. 424/133.1

FOREIGN PATENT DOCUMENTS

EP       1724589 A2      11/2006
WO       03/057715 A2     7/2003
WO       2004/016229 A2   2/2004
WO       2006/122723 A1  11/2006
WO       2007/109747 A2   9/2007

OTHER PUBLICATIONS

Rudikoff et al, Proc. Natl. Acad. Sci. USA, 79(6):1979-1983, Mar. 1982.*
Coleman P. M. Research in Immunology, 145:33-36, 1994.*
MacCallum et al, J. Mol. Biol., 262, 732-745, 1996.*
Paul, Fundamental Immunology, 3rd Edition, 1993, pp. 292-295.*
Gebhardt, Christoffer, et. al., "S100A8 and S100A9 in inflammation and cancer"; Biochemical Pharmacology Nov. 30, 2006, vol. 72, No. 11; XP005848640; ISSN: 0006-2952; pp. 1622-1631.
Foell, Dirk, et al., "S100 proteins expressed in phagocytes: a novel group of damage-associated molecular pattern molecules"; Journal Leukocyte Biology, Jan. 2007, vol. 841, No. 1; XP009092039; ISSN: 0741-5400; pp. 28-37.
Extended European Search Report issued Nov. 23, 2007, by the European Patent Office in European Application No. 07251762.6 (5 pages).
International Search Report and Written Opinion issued Oct. 21, 2008, by the Patent Cooperation Treaty (PCT) in Internatonial Application No. PCT/EP2008/003303 (18 pages).
International Preliminary Report on Patentability issued by the Patent Cooperation Treaty (PCT) on Nov. 5, 2009, in International Application No. PCT/EP2008/003303 (10 pages).
Vogl, Thomas, et al., "Biophysical characterization of S100A8 and S100A9 in the absence and presence of bivalent cations"; Elsevier, ScienceDirect, Biochimica et Biophysica Acta 1763 (2006), 1298-1306.
Lin, Li, "Rage on the Toll Road?", Cellular & Molecular Immunology, vol. 3, No. 5, Oct. 2006; pp. 351-358.
Xie, Jingjing, et al., "Hexameric Calgranulin C (S100A12) Binds to the Receptor for Advanced Glycated End Products (RAGE) Using Symmetric Hydrophobic Target-binding Patches"; Journal of Biological Chemistry, vol. 282, No. 6, Feb. 9, 2007; pp. 4218-4230.

* cited by examiner

Primary Examiner — Mark Halvorson
(74) Attorney, Agent, or Firm — David L. Fox; The JL Salazar Law Firm

(57) ABSTRACT

A method of identifying a compound for use in therapy which modulates the interaction of S1OO A9 with a ligand comprising:—determining whether a candidate compound is capable of modulating the interaction of S1OO A9 with RAGE or the interaction of S1OO A9 with a TLR (Toll like receptor), or—determining whether a candidate compound is capable of binding to S100A9 in a manner which disrupts binding of S1OO A9 with RAGE or the binding of S100A9 with a TLR, to thereby identify whether the compound may be used in therapy.

10 Claims, 23 Drawing Sheets

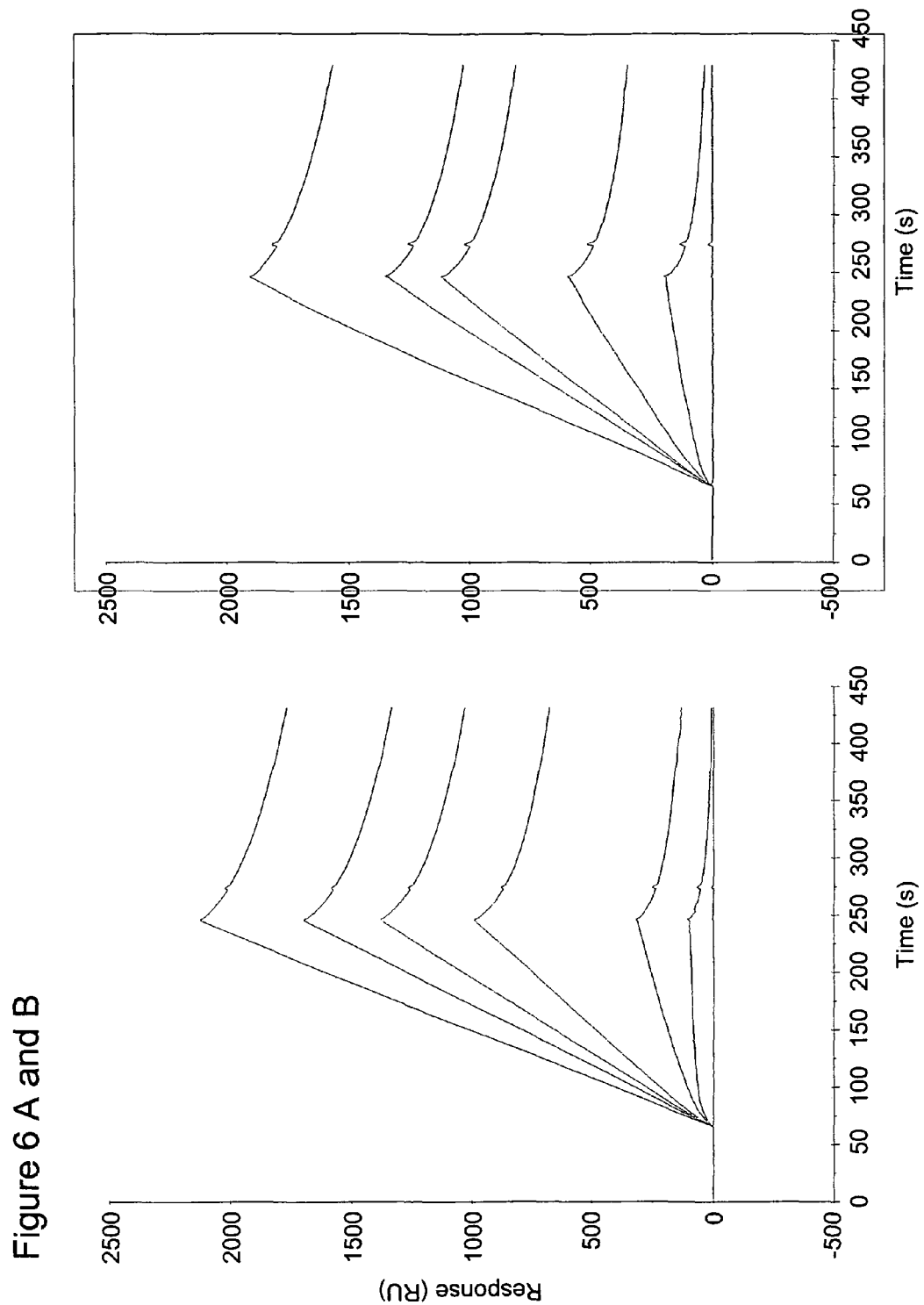
Figure 6 A and B

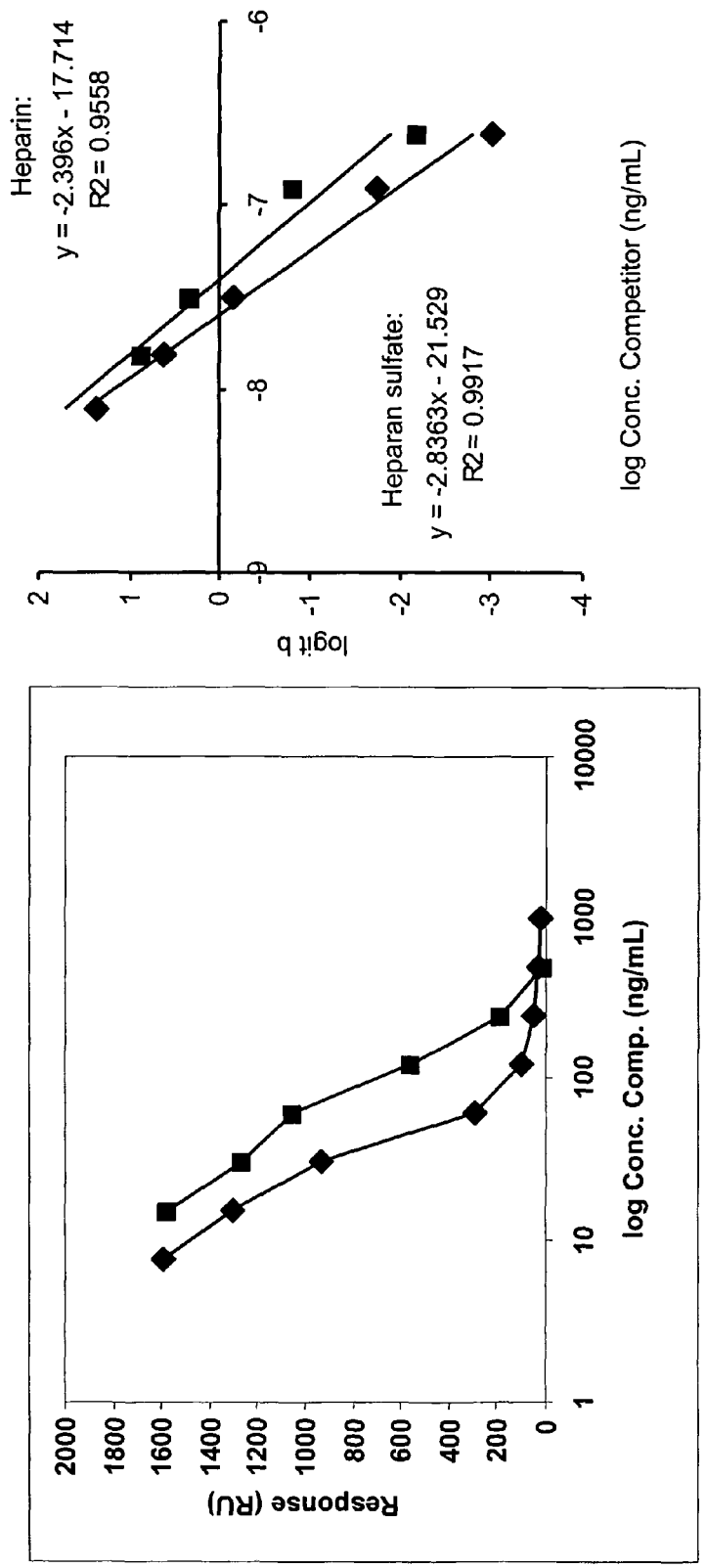
Figure 6 C and D

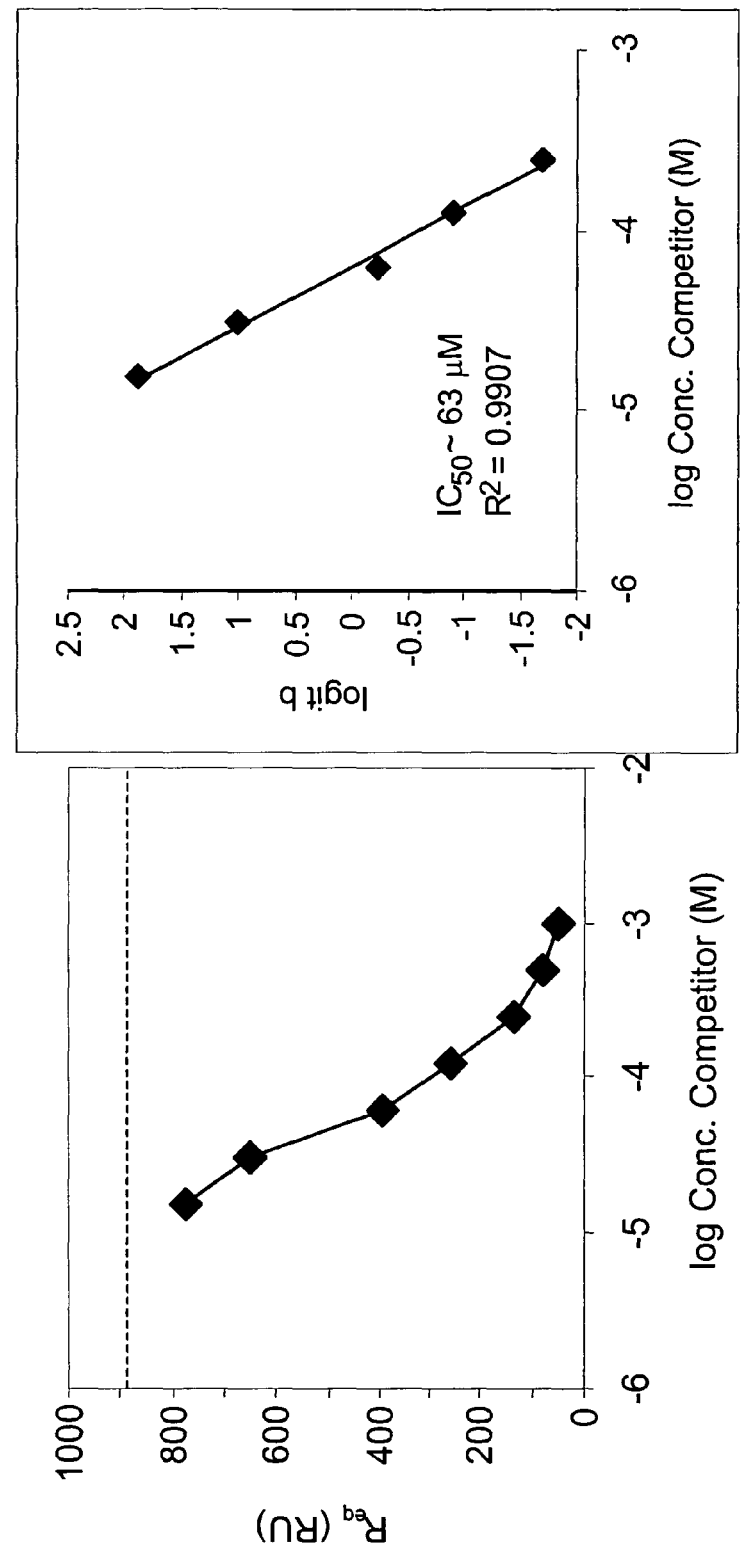
Figure 7 B and C

Figure 10. Cartoon showing an in vitro activity assay for a S100A9-binding compound A Figure 11. TOLL-induced MLR cell population.

Figure 12. Total DC population are reduced in human SLE patients.

Figure 13. Plasmacytoid DC populations.

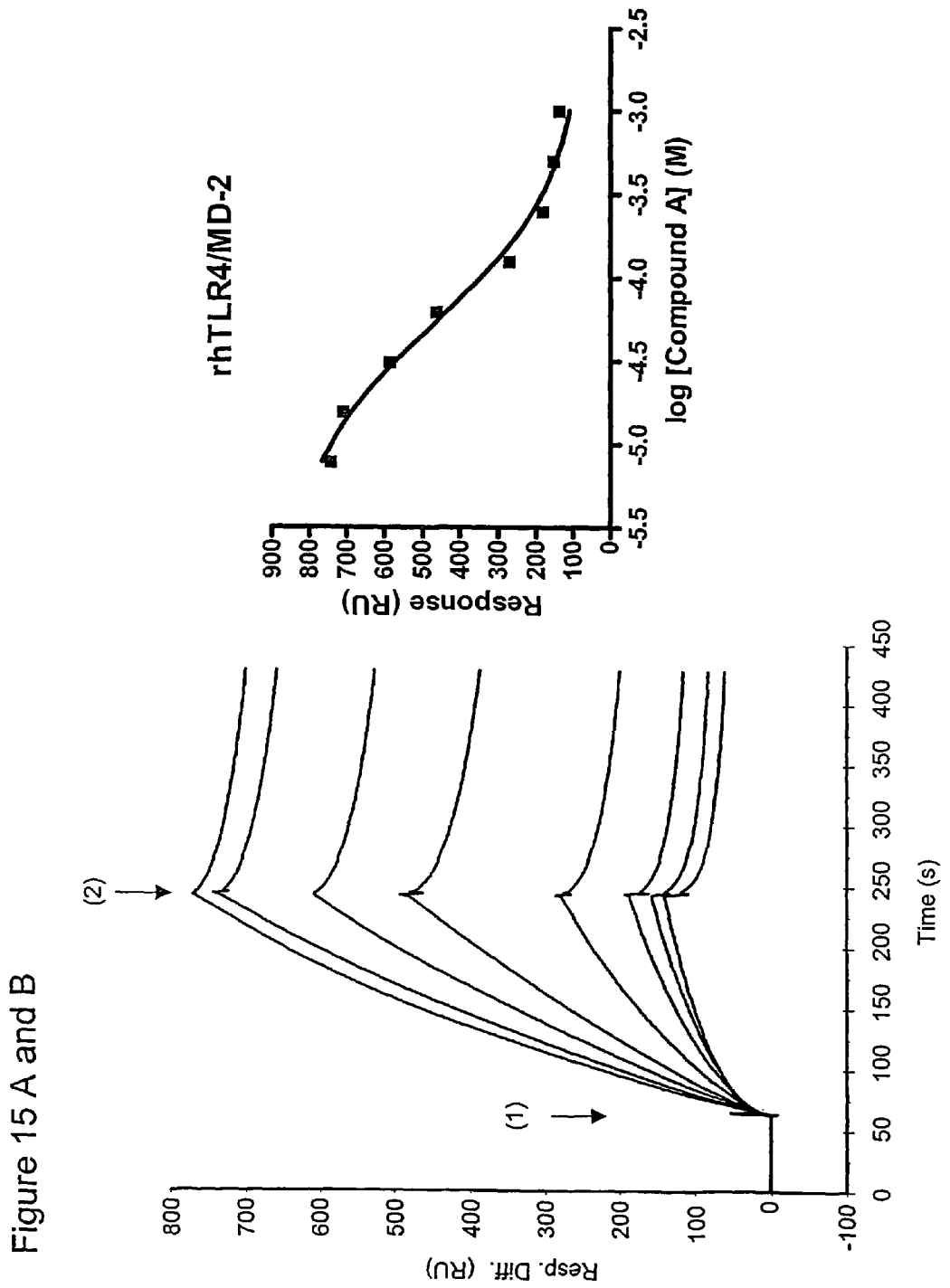
Figure 15 A and B

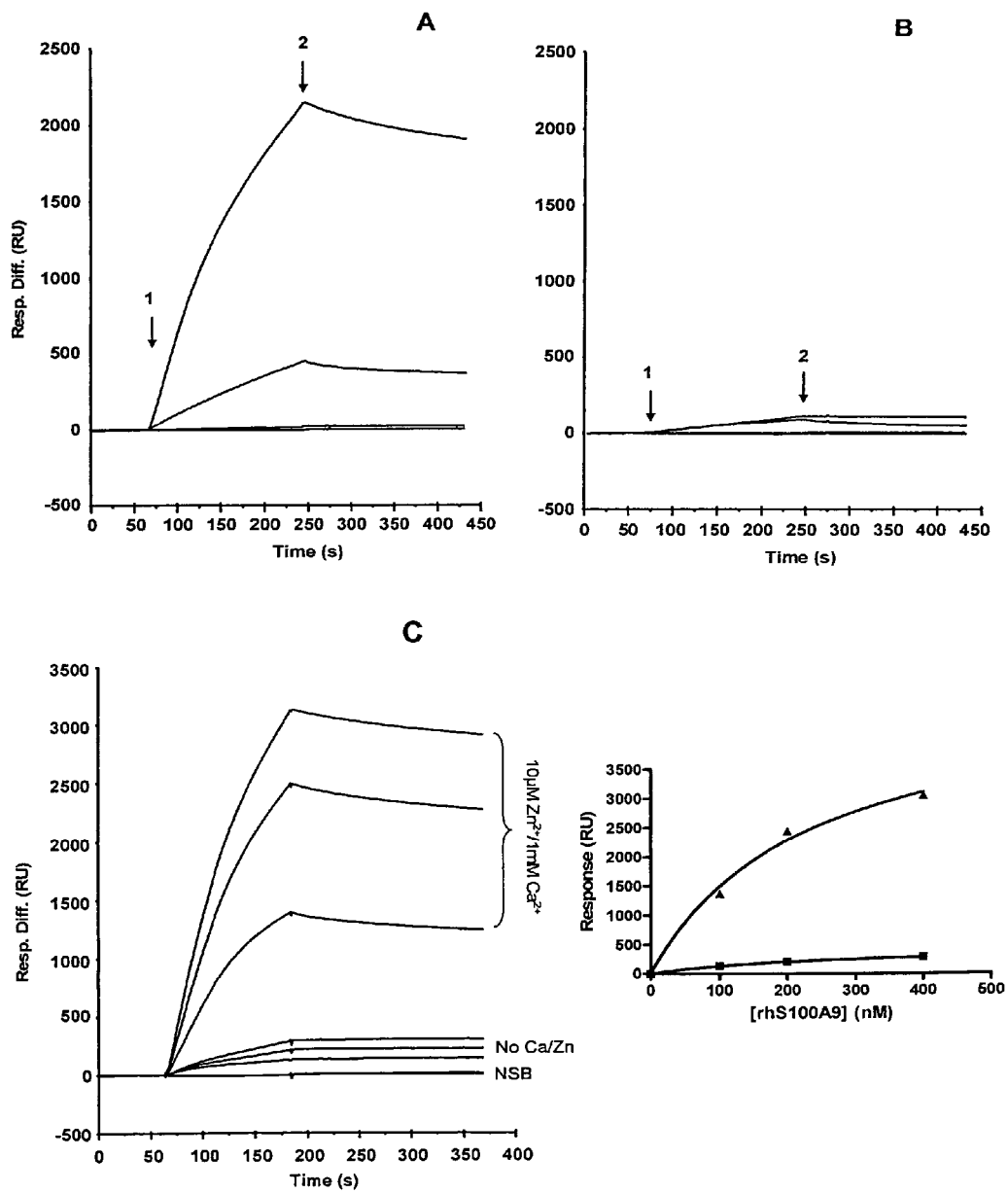
Figure 16. Characterisation of the S100A9-antibody mAb 43/8

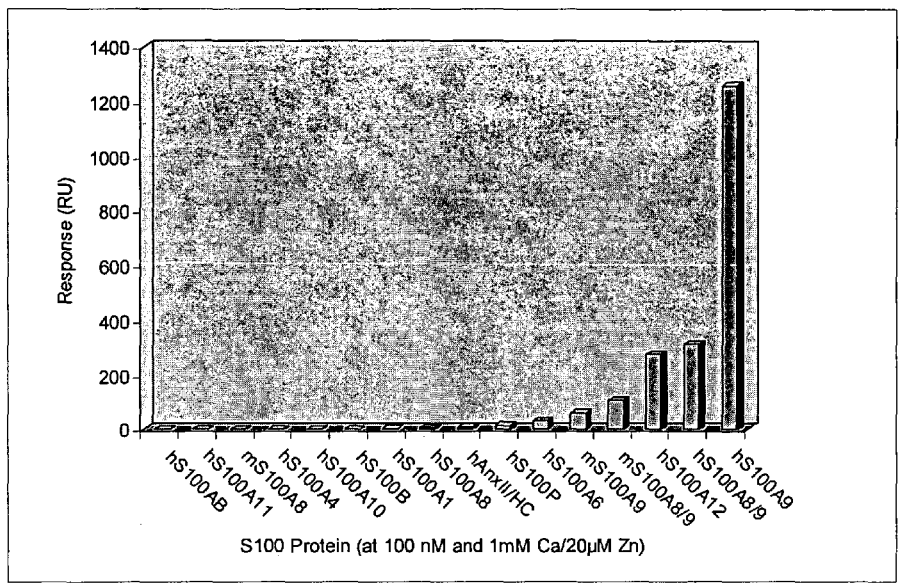
Figure 17. Binding of various S100 proteins to immobilized anti-S100A9 antibody 43/8
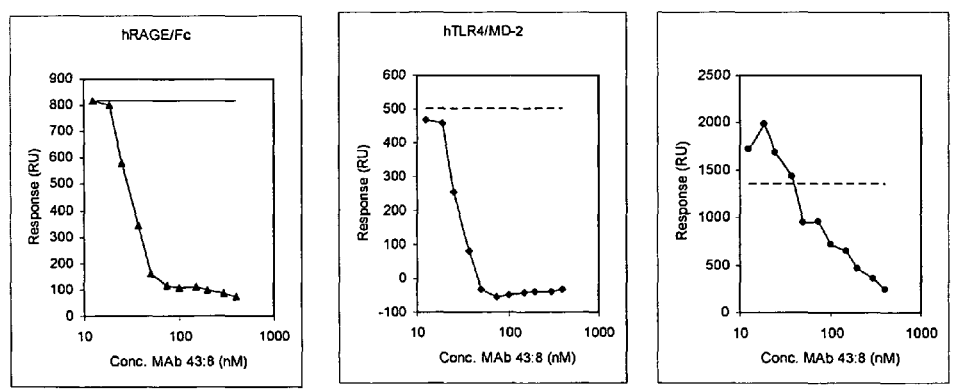
Figure 18. The S100A9-antibody mAb 43/8 blocks binding of hS100A9 to RAGE, hS100A9 to TLR4/MD-2, and hS100A9 to Compound A

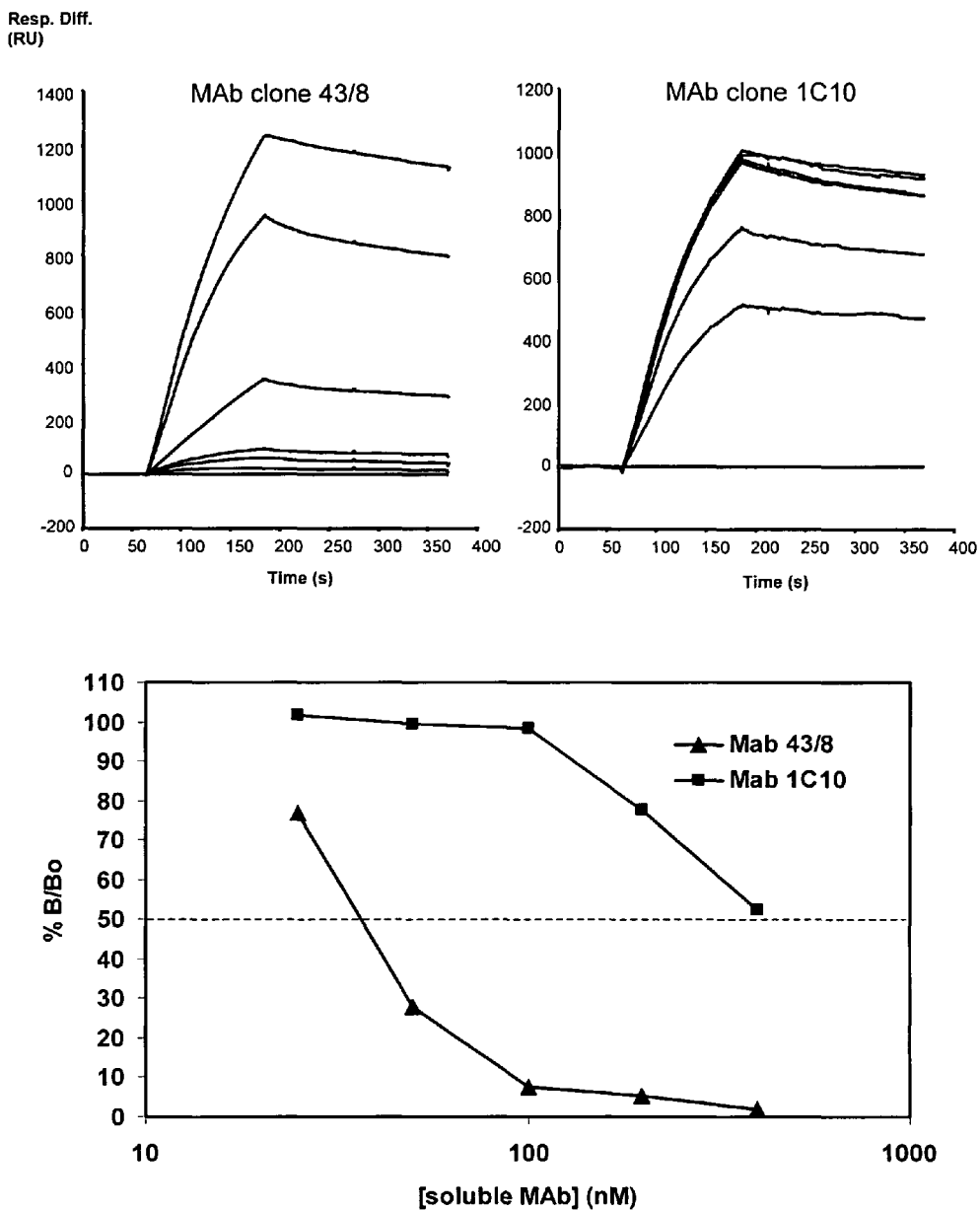
Figure 19. Binding of S100A9 to immobilized anti-S100A9 antibody is blocked by addition of anti-S100A9 antibody or 1C10 anti-S100A9 antibody. The difference in inhibition of binding S100A9 to anti-S100A9 antibody by the anti-S100A9 antibody and the 1C10 anti-S100A9 antibody

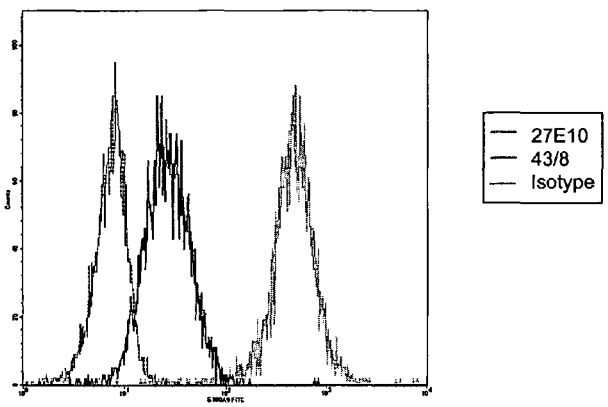

Figure 20 Shows FACS analysis of Peripheral Blood Mononuclear Cells stained with the anti-S100A9 mAb 43/8 and the 27E10 antibody, reactive to the S100A9/S100A8 complex

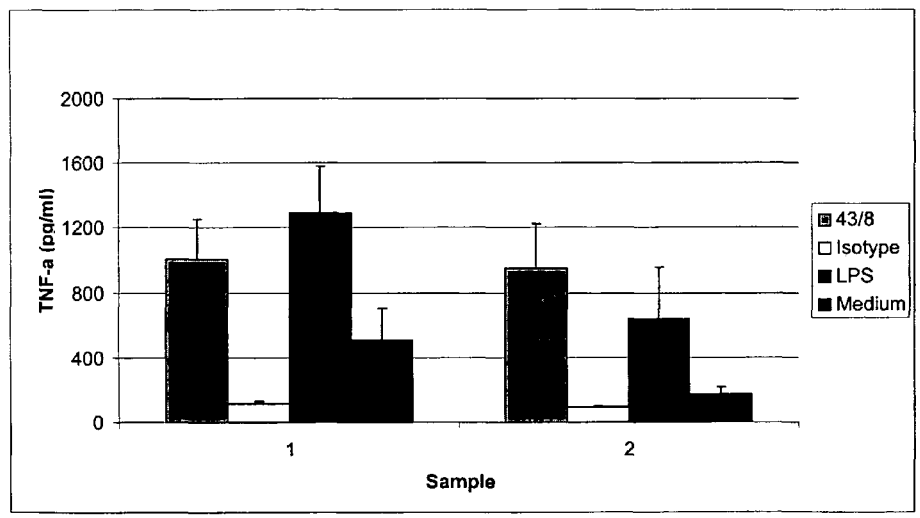

Figure 21 Shows TNFα production in Peripheral Blood Mononuclear Cells after stimulation with the beads the anti-S100A9 mAb 43/8 (10 µg/ml) or isotype control antibody (10 µg/ml). As controls are included cells incubated with medium alone or 0.5 µg/ml lipopolysaccharide (LPS).

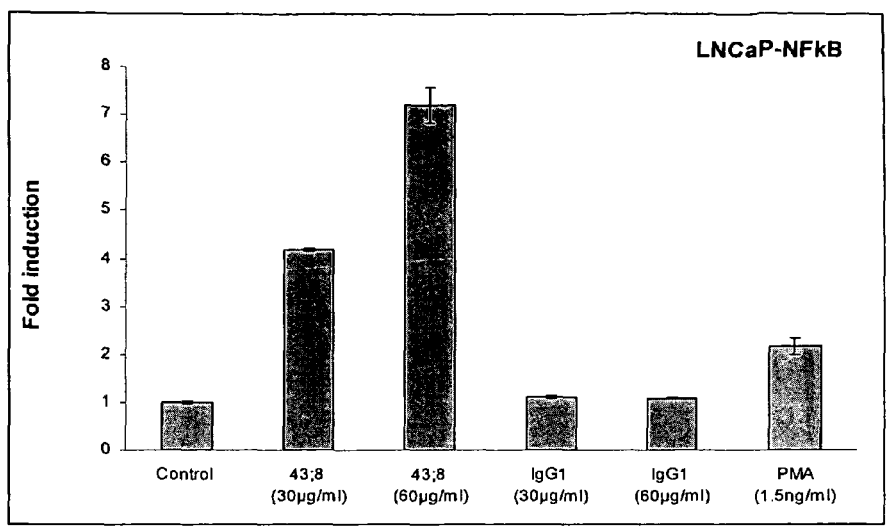
Figure 22 shows NFκB reporter gene activity in human prostate cancer cell line LNCaP after stimulation with soluble S100A9 antibody 43/8 for 4h. IgG1 was used as a negative isotype control and PMA was used as a positive control.

SEQUENCE LISTING

<160> NUMBER OF SEQ ID NOS: 21

<210> SEQ ID NO 1
<211> LENGTH: 114
<212> TYPE: PRT
<213> ORGANISM: Homo sapiens

<400> SEQUENCE: 1

```
Met Thr Cys Lys Met Ser Gln Leu Glu Arg Asn Ile Glu Thr Ile Ile
1               5                   10                  15

Asn Thr Phe His Gln Tyr Ser Val Lys Leu Gly His Pro Asp Thr Leu
            20                  25                  30

Asn Gln Gly Glu Phe Lys Glu Leu Val Arg Lys Asp Leu Gln Asn Phe
        35                  40                  45

Leu Lys Lys Glu Asn Lys Asn Glu Lys Val Ile Glu His Ile Met Glu
    50                  55                  60

Asp Leu Asp Thr Asn Ala Asp Lys Gln Leu Ser Phe Glu Glu Phe Ile
65                  70                  75                  80

Met Leu Met Ala Arg Leu Thr Trp Ala Ser His Glu Lys Met His Glu
                85                  90                  95

Gly Asp Glu Gly Pro Gly His His His Lys Pro Gly Leu Gly Glu Gly
            100                 105                 110

Thr Pro
```

<210> SEQ ID NO 2
<211> LENGTH: 237
<212> TYPE: PRT
<213> ORGANISM: Homo sapiens

<400> SEQUENCE: 2

```
Met Asp Leu Trp Ser Ala Gly Cys Val Phe Tyr Glu Ile Ala Ser Leu
1               5                   10                  15

Gln Pro Leu Phe Pro Gly Val Asn Glu Leu Asp Gln Ile Ser Lys Ile
            20                  25                  30

His Asp Val Ile Gly Thr Pro Ala Gln Lys Ile Leu Thr Lys Phe Lys
        35                  40                  45

Gln Ser Arg Ala Met Asn Phe Asp Phe Pro Phe Lys Lys Gly Ser Gly
    50                  55                  60

Ile Pro Leu Leu Thr Thr Asn Leu Ser Pro Gln Cys Leu Ser Leu Leu
65                  70                  75                  80

His Ala Met Val Ala Tyr Asp Pro Asp Glu Arg Ile Ala Ala His Gln
                85                  90                  95

Ala Leu Gln His Pro Tyr Phe Gln Glu Gln Arg Lys Thr Glu Lys Arg
            100                 105                 110

Ala Leu Gly Ser His Arg Lys Ala Gly Phe Pro Glu His Pro Val Ala
        115                 120                 125
```

```
Pro Glu Pro Leu Ser Asn Ser Cys Gln Ile Ser Lys Glu Gly Arg Lys
        130                 135                 140

Gln Lys Gln Ser Leu Lys Gln Glu Glu Asp Arg Pro Lys Arg Arg Gly
145                 150                 155                 160

Pro Ala Tyr Val Met Glu Leu Pro Lys Leu Lys Leu Ser Gly Val Val
                165                 170                 175

Arg Leu Ser Ser Tyr Ser Ser Pro Thr Leu Gln Ser Val Leu Gly Ser
            180                 185                 190

Gly Thr Asn Gly Arg Val Pro Val Leu Arg Pro Leu Lys Cys Ile Pro
        195                 200                 205

Ala Ser Lys Lys Thr Asp Pro Gln Lys Asp Leu Lys Pro Ala Pro Gln
210                 215                 220

Gln Cys Arg Leu Pro Thr Ile Val Arg Lys Gly Gly Arg
225                 230                 235
```

<210> SEQ ID NO 3
<211> LENGTH: 786
<212> TYPE: PRT
<213> ORGANISM: Homo sapiens

<400> SEQUENCE: 3

```
Met Thr Ser Ile Phe His Phe Ala Ile Ile Phe Met Leu Ile Leu Gln
1               5                   10                  15

Ile Arg Ile Gln Leu Ser Glu Glu Ser Glu Phe Leu Val Asp Arg Ser
            20                  25                  30

Lys Asn Gly Leu Ile His Val Pro Lys Asp Leu Ser Gln Lys Thr Thr
        35                  40                  45

Ile Leu Asn Ile Ser Gln Asn Tyr Ile Ser Glu Leu Trp Thr Ser Asp
    50                  55                  60

Ile Leu Ser Leu Ser Lys Leu Arg Ile Leu Ile Ser His Asn Arg
65                  70                  75                  80

Ile Gln Tyr Leu Asp Ile Ser Val Phe Lys Phe Asn Gln Glu Leu Glu
                85                  90                  95

Tyr Leu Asp Leu Ser His Asn Lys Leu Val Lys Ile Ser Cys His Pro
            100                 105                 110

Thr Val Asn Leu Lys His Leu Asp Leu Ser Phe Asn Ala Phe Asp Ala
        115                 120                 125

Leu Pro Ile Cys Lys Glu Phe Gly Asn Met Ser Gln Leu Lys Phe Leu
    130                 135                 140

Gly Leu Ser Thr Thr His Leu Glu Lys Ser Ser Val Leu Pro Ile Ala
145                 150                 155                 160

His Leu Asn Ile Ser Lys Val Leu Leu Val Leu Gly Glu Thr Tyr Gly
                165                 170                 175

Glu Lys Glu Asp Pro Glu Gly Leu Gln Asp Phe Asn Thr Glu Ser Leu
            180                 185                 190

His Ile Val Phe Pro Thr Asn Lys Glu Phe His Phe Ile Leu Asp Val
        195                 200                 205

Ser Val Lys Thr Val Ala Asn Leu Glu Leu Ser Asn Ile Lys Cys Val
    210                 215                 220

Leu Glu Asp Asn Lys Cys Ser Tyr Phe Leu Ser Ile Leu Ala Lys Leu
225                 230                 235                 240

Gln Thr Asn Pro Lys Leu Ser Asn Leu Thr Leu Asn Asn Ile Glu Thr
                245                 250                 255
```

-continued

```
Thr Trp Asn Ser Phe Ile Arg Ile Leu Gln Leu Val Trp His Thr Thr
                260                 265                 270

Val Trp Tyr Phe Ser Ile Ser Asn Val Lys Leu Gln Gly Gln Leu Asp
        275                 280                 285

Phe Arg Asp Phe Asp Tyr Ser Gly Thr Ser Leu Lys Ala Leu Ser Ile
    290                 295                 300

His Gln Val Val Ser Asp Val Phe Gly Phe Pro Gln Ser Tyr Ile Tyr
305                 310                 315                 320

Glu Ile Phe Ser Asn Met Asn Ile Lys Asn Phe Thr Val Ser Gly Thr
                325                 330                 335

Arg Met Val His Met Leu Cys Pro Ser Lys Ile Ser Pro Phe Leu His
        340                 345                 350

Leu Asp Phe Ser Asn Asn Leu Leu Thr Asp Thr Val Phe Glu Asn Cys
    355                 360                 365

Gly His Leu Thr Glu Leu Glu Thr Leu Ile Leu Gln Met Asn Gln Leu
370                 375                 380

Lys Glu Leu Ser Lys Ile Ala Glu Met Thr Thr Gln Met Lys Ser Leu
385                 390                 395                 400

Gln Gln Leu Asp Ile Ser Gln Asn Ser Val Ser Tyr Asp Glu Lys Lys
                405                 410                 415

Gly Asp Cys Ser Trp Thr Lys Ser Leu Leu Ser Leu Asn Met Ser Ser
        420                 425                 430

Asn Ile Leu Thr Asp Thr Ile Phe Arg Cys Leu Pro Pro Arg Ile Lys
    435                 440                 445

Val Leu Asp Leu His Ser Asn Lys Ile Lys Ser Ile Pro Lys Gln Val
450                 455                 460

Val Lys Leu Glu Ala Leu Gln Glu Leu Asn Val Ala Phe Asn Ser Leu
465                 470                 475                 480

Thr Asp Leu Pro Gly Cys Gly Ser Phe Ser Ser Leu Ser Val Leu Ile
                485                 490                 495

Ile Asp His Asn Ser Val Ser His Pro Ser Ala Asp Phe Phe Gln Ser
        500                 505                 510

Cys Gln Lys Met Arg Ser Ile Lys Ala Gly Asp Asn Pro Phe Gln Cys
    515                 520                 525

Thr Cys Glu Leu Gly Glu Phe Val Lys Asn Ile Asp Gln Val Ser Ser
530                 535                 540

Glu Val Leu Glu Gly Trp Pro Asp Ser Tyr Lys Cys Asp Tyr Pro Glu
545                 550                 555                 560

Ser Tyr Arg Gly Thr Leu Leu Lys Asp Phe His Met Ser Glu Leu Ser
                565                 570                 575

Cys Asn Ile Thr Leu Leu Ile Val Thr Ile Val Ala Thr Met Leu Val
        580                 585                 590

Leu Ala Val Thr Val Thr Ser Leu Cys Ser Tyr Leu Asp Leu Pro Trp
    595                 600                 605

Tyr Leu Arg Met Val Cys Gln Trp Thr Gln Thr Arg Arg Arg Ala Arg
610                 615                 620

Asn Ile Pro Leu Glu Glu Leu Gln Arg Asn Leu Gln Phe His Ala Phe
625                 630                 635                 640

Ile Ser Tyr Ser Gly His Asp Ser Phe Trp Val Lys Asn Glu Leu Leu
                645                 650                 655

Pro Asn Leu Glu Lys Glu Gly Met Gln Ile Cys Leu His Glu Arg Asn
        660                 665                 670
```

```
Phe Val Pro Gly Lys Ser Ile Val Glu Asn Ile Ile Thr Cys Ile Glu
            675                 680                 685
Lys Ser Tyr Lys Ser Ile Phe Val Leu Ser Pro Asn Phe Val Gln Ser
        690                 695                 700
Glu Trp Cys His Tyr Glu Leu Tyr Phe Ala His His Asn Leu Phe His
705                 710                 715                 720
Glu Gly Ser Asn Ser Leu Ile Leu Ile Leu Leu Glu Pro Ile Pro Gln
                725                 730                 735
Tyr Ser Ile Pro Ser Ser Tyr His Lys Leu Lys Ser Leu Met Ala Arg
                740                 745                 750
Arg Thr Tyr Leu Glu Trp Pro Lys Glu Lys Ser Lys Arg Gly Leu Phe
        755                 760                 765
Trp Ala Asn Leu Arg Ala Ala Ile Asn Ile Lys Leu Thr Glu Gln Ala
    770                 775                 780
Lys Lys
785

<210> SEQ ID NO 4
<211> LENGTH: 586
<212> TYPE: PRT
<213> ORGANISM: Homo sapiens

<400> SEQUENCE: 4

Met Pro His Thr Leu Trp Met Val Trp Leu Gly Val Ile Ile Ser
1                5                  10                  15
Leu Ser Lys Glu Glu Ser Ser Asn Gln Ala Ser Leu Ser Cys Asp Arg
            20                  25                  30
Asn Gly Ile Cys Lys Gly Ser Ser Gly Ser Leu Asn Ser Ile Pro Ser
        35                  40                  45
Gly Leu Thr Glu Ala Val Lys Ser Leu Asp Gln Ser Asn Asn Arg Ile
    50                  55                  60
Thr Tyr Ile Cys Asn Ser Asp Leu Gln Arg Cys Val Asn Leu Gln Ala
65                  70                  75                  80
Leu Val Leu Thr Ser Asn Gly Ile Asn Thr Ile Glu Glu Asp Ser Phe
                85                  90                  95
Ser Ser Leu Gly Ser Leu Glu His Leu Asp Leu Ser Tyr Asn Tyr Leu
            100                 105                 110
Ser Asn Leu Ser Ser Ser Trp Phe Lys Pro Leu Ser Ser Leu Thr Phe
        115                 120                 125
Leu Asn Leu Leu Gly Asn Pro Tyr Lys Thr Leu Gly Glu Thr Ser Leu
    130                 135                 140
Phe Ser His Leu Thr Lys Leu Gln Ile Leu Arg Val Gly Asn Met Asp
145                 150                 155                 160
Thr Phe Thr Lys Ile Gln Arg Lys Asp Phe Ala Gly Leu Thr Phe Leu
                165                 170                 175
Glu Glu Leu Glu Ile Asp Ala Ser Asp Leu Gln Ser Tyr Glu Pro Lys
            180                 185                 190
Ser Leu Lys Ser Ile Gln Asn Val Ser His Leu Ile Leu His Met Lys
        195                 200                 205
Gln His Ile Leu Leu Leu Glu Ile Phe Val Asp Val Thr Ser Ser Val
    210                 215                 220
Glu Cys Leu Glu Leu Arg Asp Thr Asp Leu Asp Thr Phe His Phe Ser
225                 230                 235                 240
Glu Leu Ser Thr Gly Glu Thr Asn Ser Leu Ile Lys Lys Phe Thr Phe
                245                 250                 255
```

Arg Asn Val Lys Ile Thr Asp Glu Ser Leu Phe Gln Val Met Lys Leu
            260                 265                 270

Leu Asn Gln Ile Ser Gly Leu Leu Glu Leu Glu Phe Asp Asp Cys Thr
            275                 280                 285

Leu Asn Gly Val Gly Asn Phe Arg Ala Ser Asp Asn Asp Arg Val Ile
            290                 295                 300

Asp Pro Gly Lys Val Glu Thr Leu Thr Ile Arg Arg Leu His Ile Pro
305                 310                 315                 320

Arg Phe Tyr Leu Phe Tyr Asp Leu Ser Thr Leu Tyr Ser Leu Thr Glu
            325                 330                 335

Arg Val Lys Arg Ile Thr Val Glu Asn Ser Lys Val Phe Leu Val Pro
            340                 345                 350

Cys Leu Leu Ser Gln His Leu Lys Ser Leu Glu Tyr Leu Asp Leu Ser
            355                 360                 365

Glu Asn Leu Met Val Glu Tyr Leu Lys Asn Ser Ala Cys Glu Asp
            370                 375                 380

Ala Trp Pro Ser Leu Gln Thr Leu Ile Leu Arg Gln Asn His Leu Ala
385                 390                 395                 400

Ser Leu Glu Lys Thr Gly Glu Thr Leu Leu Thr Leu Lys Asn Leu Thr
            405                 410                 415

Asn Ile Asp Ile Ser Lys Asn Ser Phe His Ser Met Pro Glu Thr Cys
            420                 425                 430

Gln Trp Pro Glu Lys Met Lys Tyr Leu Asn Leu Ser Ser Thr Arg Ile
            435                 440                 445

His Ser Val Thr Gly Cys Ile Pro Lys Thr Leu Glu Ile Leu Asp Val
            450                 455                 460

Ser Asn Asn Asn Leu Asn Leu Phe Ser Leu Asn Leu Pro Gln Leu Lys
465                 470                 475                 480

Glu Leu Tyr Ile Ser Arg Asn Lys Leu Met Thr Leu Pro Asp Ala Ser
            485                 490                 495

Leu Leu Pro Met Leu Leu Val Leu Lys Ile Ser Arg Asn Ala Ile Thr
            500                 505                 510

Thr Phe Ser Lys Glu Gln Leu Asp Ser Phe His Thr Leu Lys Thr Leu
            515                 520                 525

Glu Ala Gly Gly Asn Asn Phe Ile Cys Ser Cys Glu Phe Leu Ser Phe
            530                 535                 540

Thr Gln Glu Gln Gln Ala Leu Ala Lys Val Leu Ile Asp Trp Pro Ala
545                 550                 555                 560

Asn Tyr Leu Cys Asp Ser Pro Ser His Val Arg Gly Gln Gln Val Gln
            565                 570                 575

Asp Val Arg Leu Ser Val Ser Glu Cys His
            580                 585

<210> SEQ ID NO 5
<211> LENGTH: 904
<212> TYPE: PRT
<213> ORGANISM: Homo sapiens

<400> SEQUENCE: 5

Met Arg Gln Thr Leu Pro Cys Ile Tyr Phe Trp Gly Gly Leu Leu Pro
1               5                   10                  15

Phe Gly Met Leu Cys Ala Ser Ser Thr Thr Lys Cys Thr Lys Cys Val Ser His
            20                  25                  30

-continued

Glu Val Ala Asp Cys Ser His Leu Lys Leu Thr Gln Val Pro Asp Asp
    35                  40                  45

Leu Pro Thr Asn Ile Thr Val Leu Asn Leu Thr His Asn Gln Leu Arg
50                  55                  60

Arg Leu Pro Ala Ala Asn Phe Thr Arg Tyr Ser Gln Leu Thr Ser Leu
65                  70                  75                  80

Asp Val Gly Phe Asn Thr Ile Ser Lys Leu Glu Pro Glu Leu Cys Gln
                85                  90                  95

Lys Leu Pro Met Leu Lys Val Leu Asn Leu Gln His Asn Glu Leu Ser
            100                 105                 110

Gln Leu Ser Asp Lys Thr Phe Ala Phe Cys Thr Asn Leu Thr Glu Leu
        115                 120                 125

His Leu Met Ser Asn Ser Ile Gln Lys Ile Lys Asn Asn Pro Phe Val
    130                 135                 140

Lys Gln Lys Asn Leu Ile Thr Leu Asp Leu Ser His Asn Gly Leu Ser
145                 150                 155                 160

Ser Thr Lys Leu Gly Thr Gln Val Gln Leu Glu Asn Leu Gln Glu Leu
                165                 170                 175

Leu Leu Ser Asn Asn Lys Ile Gln Ala Leu Lys Ser Glu Glu Leu Asp
            180                 185                 190

Ile Phe Ala Asn Ser Ser Leu Lys Lys Leu Glu Leu Ser Ser Asn Gln
        195                 200                 205

Ile Lys Glu Phe Ser Pro Gly Cys Phe His Ala Ile Gly Arg Leu Phe
    210                 215                 220

Gly Leu Phe Leu Asn Asn Val Gln Leu Gly Pro Ser Leu Thr Glu Lys
225                 230                 235                 240

Leu Cys Leu Glu Leu Ala Asn Thr Ser Ile Arg Asn Leu Ser Leu Ser
                245                 250                 255

Asn Ser Gln Leu Ser Thr Thr Ser Asn Thr Thr Phe Leu Gly Leu Lys
            260                 265                 270

Trp Thr Asn Leu Thr Met Leu Asp Leu Ser Tyr Asn Asn Leu Asn Val
        275                 280                 285

Val Gly Asn Asp Ser Phe Ala Trp Leu Pro Gln Leu Glu Tyr Phe Phe
    290                 295                 300

Leu Glu Tyr Asn Asn Ile Gln His Leu Phe Ser His Ser Leu His Gly
305                 310                 315                 320

Leu Phe Asn Val Arg Tyr Leu Asn Leu Lys Arg Ser Phe Thr Lys Gln
                325                 330                 335

Ser Ile Ser Leu Ala Ser Leu Pro Lys Ile Asp Asp Phe Ser Phe Gln
            340                 345                 350

Trp Leu Lys Cys Leu Glu His Leu Asn Met Glu Asp Asn Asp Ile Pro
        355                 360                 365

Gly Ile Lys Ser Asn Met Phe Thr Gly Leu Ile Asn Leu Lys Tyr Leu
    370                 375                 380

Ser Leu Ser Asn Ser Phe Thr Ser Leu Arg Thr Leu Thr Asn Glu Thr
385                 390                 395                 400

Phe Val Ser Leu Ala His Ser Pro Leu His Ile Leu Asn Leu Thr Lys
                405                 410                 415

Asn Lys Ile Ser Lys Ile Glu Ser Asp Ala Phe Ser Trp Leu Gly His
            420                 425                 430

Leu Glu Val Leu Asp Leu Gly Leu Asn Glu Ile Gly Gln Glu Leu Thr
        435                 440                 445

-continued

```
Gly Gln Glu Trp Arg Gly Leu Glu Asn Ile Phe Glu Ile Tyr Leu Ser
        450                 455                 460

Tyr Asn Lys Tyr Leu Gln Leu Thr Arg Asn Ser Phe Ala Leu Val Pro
465                 470                 475                 480

Ser Leu Gln Arg Leu Met Leu Arg Arg Val Ala Leu Lys Asn Val Asp
                485                 490                 495

Ser Ser Pro Ser Pro Phe Gln Pro Leu Arg Asn Leu Thr Ile Leu Asp
            500                 505                 510

Leu Ser Asn Asn Ile Ala Asn Ile Asn Asp Asp Met Leu Glu Gly
            515                 520                 525

Leu Glu Lys Leu Glu Ile Leu Asp Leu Gln His Asn Asn Leu Ala Arg
530                 535                 540

Leu Trp Lys His Ala Asn Pro Gly Gly Pro Ile Tyr Phe Leu Lys Gly
545                 550                 555                 560

Leu Ser His Leu His Ile Leu Asn Leu Glu Ser Asn Gly Phe Asn Glu
                565                 570                 575

Ile Pro Val Glu Val Phe Lys Asp Leu Phe Glu Leu Lys Ile Ile Asp
                580                 585                 590

Leu Gly Leu Asn Asn Leu Asn Thr Leu Pro Ala Ser Val Phe Asn Asn
        595                 600                 605

Gln Val Ser Leu Lys Ser Leu Asn Leu Gln Lys Asn Leu Ile Thr Ser
    610                 615                 620

Val Glu Lys Lys Val Phe Gly Pro Ala Phe Arg Asn Leu Thr Glu Leu
625                 630                 635                 640

Asp Met Arg Phe Asn Pro Phe Asp Cys Thr Cys Glu Ser Ile Ala Trp
                645                 650                 655

Phe Val Asn Trp Ile Asn Glu Thr His Thr Asn Ile Pro Glu Leu Ser
                660                 665                 670

Ser His Tyr Leu Cys Asn Thr Pro Pro His Tyr His Gly Phe Pro Val
        675                 680                 685

Arg Leu Phe Asp Thr Ser Ser Cys Lys Asp Ser Ala Pro Phe Glu Leu
    690                 695                 700

Phe Phe Met Ile Asn Thr Ser Ile Leu Leu Ile Phe Ile Phe Ile Val
705                 710                 715                 720

Leu Leu Ile His Phe Glu Gly Trp Arg Ile Ser Phe Tyr Trp Asn Val
                725                 730                 735

Ser Val His Arg Val Leu Gly Phe Lys Glu Ile Asp Arg Gln Thr Glu
            740                 745                 750

Gln Phe Glu Tyr Ala Ala Tyr Ile Ile His Ala Tyr Lys Asp Lys Asp
        755                 760                 765

Trp Val Trp Glu His Phe Ser Ser Met Glu Lys Glu Asp Gln Ser Leu
    770                 775                 780

Lys Phe Cys Leu Glu Glu Arg Asp Phe Glu Ala Gly Val Phe Glu Leu
785                 790                 795                 800

Glu Ala Ile Val Asn Ser Ile Lys Arg Ser Arg Lys Ile Ile Phe Val
                805                 810                 815

Ile Thr His His Leu Leu Lys Asp Pro Leu Cys Lys Arg Phe Lys Val
            820                 825                 830

His His Ala Val Gln Gln Ala Ile Glu Gln Asn Leu Asp Ser Ile Ile
        835                 840                 845

Leu Val Phe Leu Glu Glu Ile Pro Asp Tyr Lys Leu Asn His Ala Leu
    850                 855                 860
```

```
Cys Leu Arg Arg Gly Met Phe Lys Ser His Cys Ile Leu Asn Trp Pro
865                 870                 875                 880

Val Gln Lys Glu Arg Ile Gly Ala Phe Arg His Lys Leu Gln Val Ala
            885                 890                 895

Leu Gly Ser Lys Asn Ser Val His
            900

<210> SEQ ID NO 6
<211> LENGTH: 839
<212> TYPE: PRT
<213> ORGANISM: Homo sapiens

<400> SEQUENCE: 6

Met Met Ser Ala Ser Arg Leu Ala Gly Thr Leu Ile Pro Ala Met Ala
1               5                   10                  15

Phe Leu Ser Cys Val Arg Pro Glu Ser Trp Glu Pro Cys Val Glu Val
                20                  25                  30

Val Pro Asn Ile Thr Tyr Gln Cys Met Glu Leu Asn Phe Tyr Lys Ile
            35                  40                  45

Pro Asp Asn Leu Pro Phe Ser Thr Lys Asn Leu Asp Leu Ser Phe Asn
50                  55                  60

Pro Leu Arg His Leu Gly Ser Tyr Ser Phe Phe Ser Phe Pro Glu Leu
65                  70                  75                  80

Gln Val Leu Asp Leu Ser Arg Cys Glu Ile Gln Thr Ile Glu Asp Gly
                85                  90                  95

Ala Tyr Gln Ser Leu Ser His Leu Ser Thr Leu Ile Leu Thr Gly Asn
            100                 105                 110

Pro Ile Gln Ser Leu Ala Leu Gly Ala Phe Ser Gly Leu Ser Ser Leu
        115                 120                 125

Gln Lys Leu Val Ala Val Glu Thr Asn Leu Ala Ser Leu Glu Asn Phe
130                 135                 140

Pro Ile Gly His Leu Lys Thr Leu Lys Glu Leu Asn Val Ala His Asn
145                 150                 155                 160

Leu Ile Gln Ser Phe Lys Leu Pro Glu Tyr Phe Ser Asn Leu Thr Asn
                165                 170                 175

Leu Glu His Leu Asp Leu Ser Ser Asn Lys Ile Gln Ser Ile Tyr Cys
            180                 185                 190

Thr Asp Leu Arg Val Leu His Gln Met Pro Leu Leu Asn Leu Ser Leu
        195                 200                 205

Asp Leu Ser Leu Asn Pro Met Asn Phe Ile Gln Pro Gly Ala Phe Lys
210                 215                 220

Glu Ile Arg Leu His Lys Leu Thr Leu Arg Asn Asn Phe Asp Ser Leu
225                 230                 235                 240

Asn Val Met Lys Thr Cys Ile Gln Gly Leu Ala Gly Leu Glu Val His
                245                 250                 255

Arg Leu Val Leu Gly Glu Phe Arg Asn Glu Gly Asn Leu Glu Lys Phe
            260                 265                 270

Asp Lys Ser Ala Leu Glu Gly Leu Cys Asn Leu Thr Ile Glu Glu Phe
        275                 280                 285

Arg Leu Ala Tyr Leu Asp Tyr Tyr Leu Asp Asp Ile Ile Asp Leu Phe
290                 295                 300

Asn Cys Leu Thr Asn Val Ser Ser Phe Ser Leu Val Ser Val Thr Ile
305                 310                 315                 320

Glu Arg Val Lys Asp Phe Ser Tyr Asn Phe Gly Trp Gln His Leu Glu
                325                 330                 335
```

-continued

```
Leu Val Asn Cys Lys Phe Gly Gln Phe Pro Thr Leu Lys Leu Lys Ser
            340                 345                 350

Leu Lys Arg Leu Thr Phe Thr Ser Asn Lys Gly Asn Ala Phe Ser
            355                 360                 365

Glu Val Asp Leu Pro Ser Leu Glu Phe Leu Asp Leu Ser Arg Asn Gly
            370                 375                 380

Leu Ser Phe Lys Gly Cys Cys Ser Gln Ser Asp Phe Gly Thr Thr Ser
385                 390                 395                 400

Leu Lys Tyr Leu Asp Leu Ser Phe Asn Gly Val Ile Thr Met Ser Ser
                405                 410                 415

Asn Phe Leu Gly Leu Glu Gln Leu Glu His Leu Asp Phe Gln His Ser
            420                 425                 430

Asn Leu Lys Gln Met Ser Glu Phe Ser Val Phe Leu Ser Leu Arg Asn
            435                 440                 445

Leu Ile Tyr Leu Asp Ile Ser His Thr His Thr Arg Val Ala Phe Asn
    450                 455                 460

Gly Ile Phe Asn Gly Leu Ser Ser Leu Glu Val Leu Lys Met Ala Gly
465                 470                 475                 480

Asn Ser Phe Gln Glu Asn Phe Leu Pro Asp Ile Phe Thr Glu Leu Arg
            485                 490                 495

Asn Leu Thr Phe Leu Asp Leu Ser Gln Cys Gln Leu Glu Gln Leu Ser
            500                 505                 510

Pro Thr Ala Phe Asn Ser Leu Ser Ser Leu Gln Val Leu Asn Met Ser
            515                 520                 525

His Asn Asn Phe Phe Ser Leu Asp Thr Phe Pro Tyr Lys Cys Leu Asn
            530                 535                 540

Ser Leu Gln Val Leu Asp Tyr Ser Leu Asn His Ile Met Thr Ser Lys
545                 550                 555                 560

Lys Gln Glu Leu Gln His Phe Pro Ser Ser Leu Ala Phe Leu Asn Leu
                565                 570                 575

Thr Gln Asn Asp Phe Ala Cys Thr Cys Glu His Gln Ser Phe Leu Gln
            580                 585                 590

Trp Ile Lys Asp Gln Arg Gln Leu Leu Val Glu Val Glu Arg Met Glu
            595                 600                 605

Cys Ala Thr Pro Ser Asp Lys Gln Gly Met Pro Val Leu Ser Leu Asn
            610                 615                 620

Ile Thr Cys Gln Met Asn Lys Thr Ile Ile Gly Val Ser Val Leu Ser
625                 630                 635                 640

Val Leu Val Val Ser Val Val Ala Val Leu Val Tyr Lys Phe Tyr Phe
                645                 650                 655

His Leu Met Leu Leu Ala Gly Cys Ile Lys Tyr Gly Arg Gly Glu Asn
            660                 665                 670

Ile Tyr Asp Ala Phe Val Ile Tyr Ser Ser Gln Asp Glu Asp Trp Val
            675                 680                 685

Arg Asn Glu Leu Val Lys Asn Leu Glu Glu Gly Val Pro Pro Phe Gln
            690                 695                 700

Leu Cys Leu His Tyr Arg Asp Phe Ile Pro Gly Val Ala Ile Ala Ala
705                 710                 715                 720

Asn Ile Ile His Glu Gly Phe His Lys Ser Arg Lys Val Ile Val Val
                725                 730                 735

Val Ser Gln His Phe Ile Gln Ser Arg Trp Cys Ile Phe Glu Tyr Glu
            740                 745                 750
```

```
Ile Ala Gln Thr Trp Gln Phe Leu Ser Ser Arg Ala Gly Ile Ile Phe
        755                 760                 765
Ile Val Leu Gln Lys Val Glu Lys Thr Leu Leu Arg Gln Gln Val Glu
        770                 775                 780
Leu Tyr Arg Leu Leu Ser Arg Asn Thr Tyr Leu Glu Trp Glu Asp Ser
785                 790                 795                 800
Val Leu Gly Arg His Ile Phe Trp Arg Leu Arg Lys Ala Leu Leu
                805                 810                 815
Asp Gly Lys Ser Trp Asn Pro Glu Gly Thr Val Gly Thr Gly Cys Asn
                820                 825                 830
Trp Gln Glu Ala Thr Ser Ile
        835

<210> SEQ ID NO 7
<211> LENGTH: 858
<212> TYPE: PRT
<213> ORGANISM: Homo sapiens

<400> SEQUENCE: 7

Met Gly Asp His Leu Asp Leu Leu Gly Val Val Leu Met Ala Gly
1               5                   10                  15
Pro Val Phe Gly Ile Pro Ser Cys Ser Phe Asp Gly Arg Ile Ala Phe
                20                  25                  30
Tyr Arg Phe Cys Asn Leu Thr Gln Val Pro Gln Val Leu Asn Thr Thr
        35                  40                  45
Glu Arg Leu Leu Leu Ser Phe Asn Tyr Ile Arg Thr Val Thr Ala Ser
    50                  55                  60
Ser Phe Pro Phe Leu Glu Gln Leu Gln Leu Leu Glu Leu Gly Ser Gln
65                  70                  75                  80
Tyr Thr Pro Leu Thr Ile Asp Lys Glu Ala Phe Arg Asn Leu Pro Asn
                85                  90                  95
Leu Arg Ile Leu Asp Leu Gly Ser Ser Lys Ile Tyr Phe Leu His Pro
            100                 105                 110
Asp Ala Phe Gln Gly Leu Phe His Leu Phe Glu Leu Arg Leu Tyr Phe
        115                 120                 125
Cys Gly Leu Ser Asp Ala Val Leu Lys Asp Gly Tyr Phe Arg Asn Leu
    130                 135                 140
Lys Ala Leu Thr Arg Leu Asp Leu Ser Lys Asn Gln Ile Arg Ser Leu
145                 150                 155                 160
Tyr Leu His Pro Ser Phe Gly Lys Leu Asn Ser Leu Lys Ser Ile Asp
                165                 170                 175
Phe Ser Ser Asn Gln Ile Phe Leu Val Cys Glu His Glu Leu Glu Pro
            180                 185                 190
Leu Gln Gly Lys Thr Leu Ser Phe Phe Ser Leu Ala Ala Asn Ser Leu
        195                 200                 205
Tyr Ser Arg Val Ser Val Asp Trp Gly Lys Cys Met Asn Pro Phe Arg
    210                 215                 220
Asn Met Val Leu Glu Ile Leu Asp Val Ser Gly Asn Gly Trp Thr Val
225                 230                 235                 240
Asp Ile Thr Gly Asn Phe Ser Asn Ala Ile Ser Lys Ser Gln Ala Phe
                245                 250                 255
Ser Leu Ile Leu Ala His His Ile Met Gly Ala Gly Phe Gly Phe His
            260                 265                 270
Asn Ile Lys Asp Pro Asp Gln Asn Thr Phe Ala Gly Leu Ala Arg Ser
        275                 280                 285
```

```
Ser Val Arg His Leu Asp Leu Ser His Gly Phe Val Phe Ser Leu Asn
    290                 295                 300
Ser Arg Val Phe Glu Thr Leu Lys Asp Leu Lys Val Leu Asn Leu Ala
305                 310                 315                 320
Tyr Asn Lys Ile Asn Lys Ile Ala Asp Glu Ala Phe Tyr Gly Leu Asp
                325                 330                 335
Asn Leu Gln Val Leu Asn Leu Ser Tyr Asn Leu Leu Gly Glu Leu Tyr
            340                 345                 350
Ser Ser Asn Phe Tyr Gly Leu Pro Lys Val Ala Tyr Ile Asp Leu Gln
        355                 360                 365
Lys Asn His Ile Ala Ile Gln Asp Gln Thr Phe Lys Phe Leu Glu
    370                 375                 380
Lys Leu Gln Thr Leu Asp Leu Arg Asp Asn Ala Leu Thr Thr Ile His
385                 390                 395                 400
Phe Ile Pro Ser Ile Pro Asp Ile Phe Leu Ser Gly Asn Lys Leu Val
                405                 410                 415
Thr Leu Pro Lys Ile Asn Leu Thr Ala Asn Leu Ile His Leu Ser Glu
            420                 425                 430
Asn Arg Leu Glu Asn Leu Asp Ile Leu Tyr Phe Leu Leu Arg Val Pro
        435                 440                 445
His Leu Gln Ile Leu Ile Leu Asn Gln Asn Arg Phe Ser Ser Cys Ser
    450                 455                 460
Gly Asp Gln Thr Pro Ser Glu Asn Pro Ser Leu Glu Gln Leu Phe Leu
465                 470                 475                 480
Gly Glu Asn Met Leu Gln Leu Ala Trp Glu Thr Glu Leu Cys Trp Asp
                485                 490                 495
Val Phe Glu Gly Leu Ser His Leu Gln Val Leu Tyr Leu Asn His Asn
            500                 505                 510
Tyr Leu Asn Ser Leu Pro Pro Gly Val Phe Ser His Leu Thr Ala Leu
        515                 520                 525
Arg Gly Leu Ser Leu Asn Ser Asn Arg Leu Thr Val Leu Ser His Asn
    530                 535                 540
Asp Leu Pro Ala Asn Leu Glu Ile Leu Asp Ile Ser Arg Asn Gln Leu
545                 550                 555                 560
Leu Ala Pro Asn Pro Asp Val Phe Val Ser Leu Ser Val Leu Asp Ile
                565                 570                 575
Thr His Asn Lys Phe Ile Cys Glu Cys Glu Leu Ser Thr Phe Ile Asn
            580                 585                 590
Trp Leu Asn His Thr Asn Val Thr Ile Ala Gly Pro Pro Ala Asp Ile
        595                 600                 605
Tyr Cys Val Tyr Pro Asp Ser Phe Ser Gly Val Ser Leu Phe Ser Leu
    610                 615                 620
Ser Thr Glu Gly Cys Asp Glu Glu Val Leu Lys Ser Leu Lys Phe
625                 630                 635                 640
Ser Leu Phe Ile Val Cys Thr Val Thr Leu Thr Phe Leu Met Thr
                645                 650                 655
Ile Leu Thr Val Thr Lys Phe Arg Gly Phe Cys Phe Ile Cys Tyr Lys
            660                 665                 670
Thr Ala Gln Arg Leu Val Phe Lys Asp His Pro Gln Gly Thr Glu Pro
        675                 680                 685
Asp Met Tyr Lys Tyr Asp Ala Tyr Leu Cys Phe Ser Ser Lys Asp Phe
    690                 695                 700
```

```
Thr Trp Val Gln Asn Ala Leu Leu Lys His Leu Asp Thr Gln Tyr Ser
705                 710                 715                 720

Asp Gln Asn Arg Phe Asn Leu Cys Phe Glu Glu Arg Asp Phe Val Pro
            725                 730                 735

Gly Glu Asn Arg Ile Ala Asn Ile Gln Asp Ala Ile Trp Asn Ser Arg
            740                 745                 750

Lys Ile Val Cys Leu Val Ser Arg His Phe Leu Arg Asp Gly Trp Cys
            755                 760                 765

Leu Glu Ala Phe Ser Tyr Ala Gln Gly Arg Cys Leu Ser Asp Leu Asn
770                 775                 780

Ser Ala Leu Ile Met Val Val Gly Ser Leu Ser Gln Tyr Gln Leu
785                 790                 795                 800

Met Lys His Gln Ser Ile Arg Gly Phe Val Gln Lys Gln Gln Tyr Leu
                805                 810                 815

Arg Trp Pro Glu Asp Phe Gln Asp Val Gly Trp Phe Leu His Lys Leu
            820                 825                 830

Ser Gln Gln Ile Leu Lys Lys Glu Lys Glu Lys Lys Asp Asn Asn
            835                 840                 845

Ile Pro Leu Gln Thr Val Ala Thr Ile Ser
850                 855

<210> SEQ ID NO 8
<211> LENGTH: 796
<212> TYPE: PRT
<213> ORGANISM: Homo sapiens

<400> SEQUENCE: 8

Met Thr Lys Asp Lys Glu Pro Ile Val Lys Ser Phe His Phe Val Cys
1               5                   10                  15

Leu Met Ile Ile Ile Val Gly Thr Arg Ile Gln Phe Ser Asp Gly Asn
                20                  25                  30

Glu Phe Ala Val Asp Lys Ser Lys Arg Gly Leu Ile His Val Pro Lys
        35                  40                  45

Asp Leu Pro Leu Lys Thr Lys Val Leu Asp Met Ser Gln Asn Tyr Ile
    50                  55                  60

Ala Glu Leu Gln Val Ser Asp Met Ser Phe Leu Ser Glu Leu Thr Val
65                  70                  75                  80

Leu Arg Leu Ser His Asn Arg Ile Gln Leu Leu Asp Leu Ser Val Phe
                85                  90                  95

Lys Phe Asn Gln Asp Leu Glu Tyr Leu Asp Leu Ser His Asn Gln Leu
            100                 105                 110

Gln Lys Ile Ser Cys His Pro Ile Val Ser Phe Arg His Leu Asp Leu
        115                 120                 125

Ser Phe Asn Asp Phe Lys Ala Leu Pro Ile Cys Lys Glu Phe Gly Asn
    130                 135                 140

Leu Ser Gln Leu Asn Phe Leu Gly Leu Ser Ala Met Lys Leu Gln Lys
145                 150                 155                 160

Leu Asp Leu Leu Pro Ile Ala His Leu His Leu Ser Tyr Ile Leu Leu
                165                 170                 175

Asp Leu Arg Asn Tyr Tyr Ile Lys Glu Asn Glu Thr Glu Ser Leu Gln
            180                 185                 190

Ile Leu Asn Ala Lys Thr Leu His Leu Val Phe His Pro Thr Ser Leu
        195                 200                 205

Phe Ala Ile Gln Val Asn Ile Ser Val Asn Thr Leu Gly Cys Leu Gln
    210                 215                 220
```

-continued

```
Leu Thr Asn Ile Lys Leu Asn Asp Asp Asn Cys Gln Val Phe Ile Lys
225                 230                 235                 240

Phe Leu Ser Glu Leu Thr Arg Gly Ser Thr Leu Leu Asn Phe Thr Leu
            245                 250                 255

Asn His Ile Glu Thr Thr Trp Lys Cys Leu Val Arg Val Phe Gln Phe
        260                 265                 270

Leu Trp Pro Lys Pro Val Glu Tyr Leu Asn Ile Tyr Asn Leu Thr Ile
    275                 280                 285

Ile Glu Ser Ile Arg Glu Asp Phe Thr Tyr Ser Lys Thr Thr Leu
290                 295                 300

Lys Ala Leu Thr Ile Glu His Ile Thr Asn Gln Val Phe Leu Phe Ser
305                 310                 315                 320

Gln Thr Ala Leu Tyr Thr Val Phe Ser Glu Met Asn Ile Met Met Leu
            325                 330                 335

Thr Ile Ser Asp Thr Pro Phe Ile His Met Leu Cys Pro His Ala Pro
        340                 345                 350

Ser Thr Phe Lys Phe Leu Asn Phe Thr Gln Asn Val Phe Thr Asp Ser
    355                 360                 365

Ile Phe Glu Lys Cys Ser Thr Leu Val Lys Leu Glu Thr Leu Ile Leu
370                 375                 380

Gln Lys Asn Gly Leu Lys Asp Leu Phe Lys Val Gly Leu Met Thr Lys
385                 390                 395                 400

Asp Met Pro Ser Leu Glu Ile Leu Asp Val Ser Trp Asn Ser Leu Glu
            405                 410                 415

Ser Gly Arg His Lys Glu Asn Cys Thr Trp Val Glu Ser Ile Val Val
        420                 425                 430

Leu Asn Leu Ser Ser Asn Met Leu Thr Asp Ser Val Phe Arg Cys Leu
    435                 440                 445

Pro Pro Arg Ile Lys Val Leu Asp Leu His Ser Asn Lys Ile Lys Ser
450                 455                 460

Val Pro Lys Gln Val Val Lys Leu Glu Ala Leu Gln Glu Leu Asn Val
465                 470                 475                 480

Ala Phe Asn Ser Leu Thr Asp Leu Pro Gly Cys Gly Ser Phe Ser Ser
            485                 490                 495

Leu Ser Val Leu Ile Ile Asp His Asn Ser Val Ser His Pro Ser Ala
        500                 505                 510

Asp Phe Phe Gln Ser Cys Gln Lys Met Arg Ser Ile Lys Ala Gly Asp
    515                 520                 525

Asn Pro Phe Gln Cys Thr Cys Glu Leu Arg Glu Phe Val Lys Asn Ile
530                 535                 540

Asp Gln Val Ser Ser Glu Val Leu Glu Gly Trp Pro Asp Ser Tyr Lys
545                 550                 555                 560

Cys Asp Tyr Pro Glu Ser Tyr Arg Gly Ser Pro Leu Lys Asp Phe His
            565                 570                 575

Met Ser Glu Leu Ser Cys Asn Ile Thr Leu Leu Ile Val Thr Ile Gly
        580                 585                 590

Ala Thr Met Leu Val Leu Ala Val Thr Val Thr Ser Leu Cys Ile Tyr
    595                 600                 605

Leu Asp Leu Pro Trp Tyr Leu Arg Met Val Cys Gln Trp Thr Gln Thr
610                 615                 620

Arg Arg Arg Ala Arg Asn Ile Pro Leu Glu Glu Leu Gln Arg Asn Leu
625                 630                 635                 640
```

Gln Phe His Ala Phe Ile Ser Tyr Ser Glu His Asp Ser Ala Trp Val
                    645                 650                 655

Lys Ser Glu Leu Val Pro Tyr Leu Glu Lys Glu Asp Ile Gln Ile Cys
            660                 665                 670

Leu His Glu Arg Asn Phe Val Pro Gly Lys Ser Ile Val Glu Asn Ile
        675                 680                 685

Ile Asn Cys Ile Glu Lys Ser Tyr Lys Ser Phe Val Leu Ser Pro
690                 695                 700

Asn Phe Val Gln Ser Glu Trp Cys His Tyr Glu Leu Tyr Phe Ala His
705                 710                 715                 720

His Asn Leu Phe His Glu Gly Ser Asn Leu Ile Leu Ile Leu Leu
                725                 730                 735

Glu Pro Ile Pro Gln Asn Ser Ile Pro Asn Lys Tyr His Lys Leu Lys
            740                 745                 750

Ala Leu Met Thr Gln Arg Thr Tyr Leu Gln Trp Pro Lys Glu Lys Ser
        755                 760                 765

Lys Arg Gly Leu Phe Trp Ala Asn Ile Arg Ala Ala Phe Asn Met Lys
    770                 775                 780

Leu Thr Leu Val Thr Glu Asn Asn Asp Val Lys Ser
785                 790                 795

<210> SEQ ID NO 9
<211> LENGTH: 1049
<212> TYPE: PRT
<213> ORGANISM: Homo sapiens

<400> SEQUENCE: 9

Met Val Phe Pro Met Trp Thr Leu Lys Arg Gln Ile Leu Ile Leu Phe
1               5                   10                  15

Asn Ile Ile Leu Ile Ser Lys Leu Leu Gly Ala Arg Trp Phe Pro Lys
            20                  25                  30

Thr Leu Pro Cys Asp Val Thr Leu Asp Val Pro Lys Asn His Val Ile
        35                  40                  45

Val Asp Cys Thr Asp Lys His Leu Thr Glu Ile Pro Gly Gly Ile Pro
    50                  55                  60

Thr Asn Thr Thr Asn Leu Thr Leu Thr Ile Asn His Ile Pro Asp Ile
65                  70                  75                  80

Ser Pro Ala Ser Phe His Arg Leu Asp His Leu Val Glu Ile Asp Phe
                85                  90                  95

Arg Cys Asn Cys Val Pro Ile Pro Leu Gly Ser Lys Asn Asn Met Cys
            100                 105                 110

Ile Lys Arg Leu Gln Ile Lys Pro Arg Ser Phe Ser Gly Leu Thr Tyr
        115                 120                 125

Leu Lys Ser Leu Tyr Leu Asp Gly Asn Gln Leu Leu Glu Ile Pro Gln
    130                 135                 140

Gly Leu Pro Pro Ser Leu Gln Leu Leu Ser Leu Glu Ala Asn Asn Ile
145                 150                 155                 160

Phe Ser Ile Arg Lys Glu Asn Leu Thr Glu Leu Ala Asn Ile Glu Ile
                165                 170                 175

Leu Tyr Leu Gly Gln Asn Cys Tyr Tyr Arg Asn Pro Cys Tyr Val Ser
            180                 185                 190

Tyr Ser Ile Glu Lys Asp Ala Phe Leu Asn Leu Thr Lys Leu Lys Val
        195                 200                 205

Leu Ser Leu Lys Asp Asn Asn Val Thr Ala Val Pro Thr Val Leu Pro
    210                 215                 220

-continued

Ser Thr Leu Thr Glu Leu Tyr Leu Tyr Asn Asn Met Ile Ala Lys Ile
225                 230                 235                 240

Gln Glu Asp Asp Phe Asn Asn Leu Asn Gln Leu Gln Ile Leu Asp Leu
            245                 250                 255

Ser Gly Asn Cys Pro Arg Cys Tyr Asn Ala Pro Phe Pro Cys Ala Pro
                260                 265                 270

Cys Lys Asn Asn Ser Pro Leu Gln Ile Pro Val Asn Ala Phe Asp Ala
        275                 280                 285

Leu Thr Glu Leu Lys Val Leu Arg Leu His Ser Asn Ser Leu Gln His
    290                 295                 300

Val Pro Pro Arg Trp Phe Lys Asn Ile Asn Lys Leu Gln Glu Leu Asp
305                 310                 315                 320

Leu Ser Gln Asn Phe Leu Ala Lys Glu Ile Gly Asp Ala Lys Phe Leu
                325                 330                 335

His Phe Leu Pro Ser Leu Ile Gln Leu Asp Leu Ser Phe Asn Phe Glu
            340                 345                 350

Leu Gln Val Tyr Arg Ala Ser Met Asn Leu Ser Gln Ala Phe Ser Ser
        355                 360                 365

Leu Lys Ser Leu Lys Ile Leu Arg Ile Arg Gly Tyr Val Phe Lys Glu
370                 375                 380

Leu Lys Ser Phe Asn Leu Ser Pro Leu His Asn Leu Gln Asn Leu Glu
385                 390                 395                 400

Val Leu Asp Leu Gly Thr Asn Phe Ile Lys Ile Ala Asn Leu Ser Met
                405                 410                 415

Phe Lys Gln Phe Lys Arg Leu Lys Val Ile Asp Leu Ser Val Asn Lys
            420                 425                 430

Ile Ser Pro Ser Gly Asp Ser Ser Glu Val Gly Phe Cys Ser Asn Ala
        435                 440                 445

Arg Thr Ser Val Glu Ser Tyr Glu Pro Gln Val Leu Glu Gln Leu His
    450                 455                 460

Tyr Phe Arg Tyr Asp Lys Tyr Ala Arg Ser Cys Arg Phe Lys Asn Lys
465                 470                 475                 480

Glu Ala Ser Phe Met Ser Val Asn Glu Ser Cys Tyr Lys Tyr Gly Gln
                485                 490                 495

Thr Leu Asp Leu Ser Lys Asn Ser Ile Phe Phe Val Lys Ser Ser Asp
            500                 505                 510

Phe Gln His Leu Ser Phe Leu Lys Cys Leu Asn Leu Ser Gly Asn Leu
        515                 520                 525

Ile Ser Gln Thr Leu Asn Gly Ser Glu Phe Gln Pro Leu Ala Glu Leu
    530                 535                 540

Arg Tyr Leu Asp Phe Ser Asn Asn Arg Leu Asp Leu Leu His Ser Thr
545                 550                 555                 560

Ala Phe Glu Glu Leu His Lys Leu Glu Val Leu Asp Ile Ser Ser Asn
                565                 570                 575

Ser His Tyr Phe Gln Ser Glu Gly Ile Thr His Met Leu Asn Phe Thr
            580                 585                 590

Lys Asn Leu Lys Val Leu Gln Lys Leu Met Met Asn Asp Asn Asp Ile
        595                 600                 605

Ser Ser Ser Thr Ser Arg Thr Met Glu Ser Glu Ser Leu Arg Thr Leu
    610                 615                 620

Glu Phe Arg Gly Asn His Leu Asp Val Leu Trp Arg Glu Gly Asp Asn
625                 630                 635                 640

-continued

```
Arg Tyr Leu Gln Leu Phe Lys Asn Leu Leu Lys Leu Glu Glu Leu Asp
            645                 650                 655

Ile Ser Lys Asn Ser Leu Ser Phe Leu Pro Ser Gly Val Phe Asp Gly
        660                 665                 670

Met Pro Pro Asn Leu Lys Asn Leu Ser Leu Ala Lys Asn Gly Leu Lys
        675                 680                 685

Ser Phe Ser Trp Lys Lys Leu Gln Cys Leu Lys Asn Leu Glu Thr Leu
690                 695                 700

Asp Leu Ser His Asn Gln Leu Thr Thr Val Pro Glu Arg Leu Ser Asn
705                 710                 715                 720

Cys Ser Arg Ser His Lys Asn Leu Ile Leu Lys Asn Asn Gln Ile Arg
                725                 730                 735

Ser Pro Thr Lys Tyr Phe Leu Gln Asp Ala Phe Gln Leu Arg Tyr Leu
            740                 745                 750

Asp Leu Ser Ser Asn Lys Ile Gln Met Ile Gln Lys Thr Ser Phe Pro
        755                 760                 765

Glu Asn Val Leu Asn Asn Leu Lys Met Leu Leu Leu His His Asn Arg
        770                 775                 780

Phe Leu Cys Thr Cys Asp Ala Val Trp Phe Val Trp Trp Val Asn His
785                 790                 795                 800

Thr Glu Val Thr Ile Pro Tyr Leu Ala Thr Asp Val Thr Cys Val Gly
                805                 810                 815

Pro Gly Ala His Lys Gly Gln Ser Val Ile Ser Leu Asp Leu Tyr Thr
            820                 825                 830

Cys Glu Leu Asp Leu Thr Asn Leu Ile Leu Phe Ser Leu Ser Ile Ser
        835                 840                 845

Val Ser Leu Phe Leu Met Val Met Met Thr Ala Ser His Leu Tyr Phe
850                 855                 860

Trp Asp Val Trp Tyr Ile Tyr His Phe Cys Lys Ala Lys Ile Lys Gly
865                 870                 875                 880

Tyr Gln Arg Leu Ile Ser Pro Asp Cys Cys Tyr Asp Ala Phe Ile Val
                885                 890                 895

Tyr Asp Thr Lys Asp Pro Ala Val Thr Glu Trp Val Leu Ala Glu Leu
            900                 905                 910

Val Ala Lys Leu Glu Asp Pro Arg Glu Lys His Phe Asn Leu Cys Leu
        915                 920                 925

Glu Glu Arg Asp Trp Leu Pro Gly Gln Pro Val Leu Glu Asn Leu Ser
        930                 935                 940

Gln Ser Ile Gln Leu Ser Lys Lys Thr Val Phe Val Met Thr Asp Lys
945                 950                 955                 960

Tyr Ala Lys Thr Glu Asn Phe Lys Ile Ala Phe Tyr Leu Ser His Gln
                965                 970                 975

Arg Leu Met Asp Glu Lys Val Asp Val Ile Ile Leu Ile Phe Leu Glu
            980                 985                 990

Lys Pro Phe Gln Lys Ser Lys Phe Leu Gln Leu Arg Lys Arg Leu Cys
        995                 1000                1005

Gly Ser Ser Val Leu Glu Trp Pro Thr Asn Pro Gln Ala His Pro
    1010                1015                1020

Tyr Phe Trp Gln Cys Leu Lys Asn Ala Leu Ala Thr Asp Asn His
    1025                1030                1035

Val Ala Tyr Ser Gln Val Phe Lys Glu Thr Val
    1040                1045
```

<210> SEQ ID NO 10
<211> LENGTH: 1059
<212> TYPE: PRT
<213> ORGANISM: Homo sapiens

<400> SEQUENCE: 10

Met Lys Glu Ser Ser Leu Gln Asn Ser Ser Cys Ser Leu Gly Lys Glu
1               5                   10                  15

Thr Lys Lys Glu Asn Met Phe Leu Gln Ser Ser Met Leu Thr Cys Ile
            20                  25                  30

Phe Leu Leu Ile Ser Gly Ser Cys Glu Leu Cys Ala Glu Glu Asn Phe
        35                  40                  45

Ser Arg Ser Tyr Pro Cys Asp Glu Lys Lys Gln Asn Asp Ser Val Ile
    50                  55                  60

Ala Glu Cys Ser Asn Arg Arg Leu Gln Glu Val Pro Gln Thr Val Gly
65                  70                  75                  80

Lys Tyr Val Thr Glu Leu Asp Leu Ser Asp Asn Phe Ile Thr His Ile
                85                  90                  95

Thr Asn Glu Ser Phe Gln Gly Leu Gln Asn Leu Thr Lys Ile Asn Leu
            100                 105                 110

Asn His Asn Pro Asn Val Gln His Gln Asn Gly Asn Pro Gly Ile Gln
        115                 120                 125

Ser Asn Gly Leu Asn Ile Thr Asp Gly Ala Phe Leu Asn Leu Lys Asn
    130                 135                 140

Leu Arg Glu Leu Leu Leu Glu Asp Asn Gln Leu Pro Gln Ile Pro Ser
145                 150                 155                 160

Gly Leu Pro Glu Ser Leu Thr Glu Leu Ser Leu Ile Gln Asn Asn Ile
                165                 170                 175

Tyr Asn Ile Thr Lys Glu Gly Ile Ser Arg Leu Ile Asn Leu Lys Asn
            180                 185                 190

Leu Tyr Leu Ala Trp Asn Cys Tyr Phe Asn Lys Val Cys Glu Lys Thr
        195                 200                 205

Asn Ile Glu Asp Gly Val Phe Glu Thr Leu Thr Asn Leu Glu Leu Leu
    210                 215                 220

Ser Leu Ser Phe Asn Ser Leu Ser His Val Ser Pro Lys Leu Pro Ser
225                 230                 235                 240

Ser Leu Arg Lys Leu Phe Leu Ser Asn Thr Gln Ile Lys Tyr Ile Ser
                245                 250                 255

Glu Glu Asp Phe Lys Gly Leu Ile Asn Leu Thr Leu Leu Asp Leu Ser
            260                 265                 270

Gly Asn Cys Pro Arg Cys Phe Asn Ala Pro Phe Pro Cys Val Pro Cys
        275                 280                 285

Asp Gly Gly Ala Ser Ile Asn Ile Asp Arg Phe Ala Phe Gln Asn Leu
    290                 295                 300

Thr Gln Leu Arg Tyr Leu Asn Leu Ser Ser Thr Ser Leu Arg Lys Ile
305                 310                 315                 320

Asn Ala Ala Trp Phe Lys Asn Met Pro His Leu Lys Val Leu Asp Leu
                325                 330                 335

Glu Phe Asn Tyr Leu Val Gly Glu Ile Ala Ser Gly Ala Phe Leu Thr
            340                 345                 350

Met Leu Pro Arg Leu Glu Ile Leu Asp Leu Ser Phe Asn Tyr Ile Lys
        355                 360                 365

Gly Ser Tyr Pro Gln His Ile Asn Ile Ser Arg Asn Phe Ser Lys Pro
    370                 375                 380

```
Leu Ser Leu Arg Ala Leu His Leu Arg Gly Tyr Val Phe Gln Glu Leu
385                 390                 395                 400

Arg Glu Asp Asp Phe Gln Pro Leu Met Gln Leu Pro Asn Leu Ser Thr
            405                 410                 415

Ile Asn Leu Gly Ile Asn Phe Ile Lys Gln Ile Asp Phe Lys Leu Phe
                420                 425                 430

Gln Asn Phe Ser Asn Leu Glu Ile Ile Tyr Leu Ser Glu Asn Arg Ile
        435                 440                 445

Ser Pro Leu Val Lys Asp Thr Arg Gln Ser Tyr Ala Asn Ser Ser Ser
    450                 455                 460

Phe Gln Arg His Ile Arg Lys Arg Arg Ser Thr Asp Phe Glu Phe Asp
465                 470                 475                 480

Pro His Ser Asn Phe Tyr His Phe Thr Arg Pro Leu Ile Lys Pro Gln
                485                 490                 495

Cys Ala Ala Tyr Gly Lys Ala Leu Asp Leu Ser Leu Asn Ser Ile Phe
                500                 505                 510

Phe Ile Gly Pro Asn Gln Phe Glu Asn Leu Pro Asp Ile Ala Cys Leu
            515                 520                 525

Asn Leu Ser Ala Asn Ser Asn Ala Gln Val Leu Ser Gly Thr Glu Phe
    530                 535                 540

Ser Ala Ile Pro His Val Lys Tyr Leu Asp Leu Thr Asn Asn Arg Leu
545                 550                 555                 560

Asp Phe Asp Asn Ala Ser Ala Leu Thr Glu Leu Ser Asp Leu Glu Val
                565                 570                 575

Leu Asp Leu Ser Tyr Asn Ser His Tyr Phe Arg Ile Ala Gly Val Thr
            580                 585                 590

His His Leu Glu Phe Ile Gln Asn Phe Thr Asn Leu Lys Val Leu Asn
        595                 600                 605

Leu Ser His Asn Asn Ile Tyr Thr Leu Thr Asp Lys Tyr Asn Leu Glu
    610                 615                 620

Ser Lys Ser Leu Val Glu Leu Val Phe Ser Gly Asn Arg Leu Asp Ile
625                 630                 635                 640

Leu Trp Asn Asp Asp Asp Asn Arg Tyr Ile Ser Ile Phe Lys Gly Leu
                645                 650                 655

Lys Asn Leu Thr Arg Leu Asp Leu Ser Leu Asn Arg Leu Lys His Ile
                660                 665                 670

Pro Asn Glu Ala Phe Leu Asn Leu Pro Ala Ser Leu Thr Glu Leu His
            675                 680                 685

Ile Asn Asp Asn Met Leu Lys Phe Phe Asn Trp Thr Leu Leu Gln Gln
        690                 695                 700

Phe Pro Arg Leu Glu Leu Leu Asp Leu Arg Gly Asn Lys Leu Leu Phe
705                 710                 715                 720

Leu Thr Asp Ser Leu Ser Asp Phe Thr Ser Ser Leu Arg Thr Leu Leu
                725                 730                 735

Leu Ser His Asn Arg Ile Ser His Leu Pro Ser Gly Phe Leu Ser Glu
        740                 745                 750

Val Ser Ser Leu Lys His Leu Asp Leu Ser Ser Asn Leu Leu Lys Thr
    755                 760                 765

Ile Asn Lys Ser Ala Leu Glu Thr Lys Thr Thr Lys Leu Ser Met
770                 775                 780

Leu Glu Leu His Gly Asn Pro Phe Glu Cys Thr Cys Asp Ile Gly Asp
785                 790                 795                 800
```

-continued

```
Phe Arg Arg Trp Met Asp Glu His Leu Asn Val Lys Ile Pro Arg Leu
                805                 810                 815

Val Asp Val Ile Cys Ala Ser Pro Gly Asp Gln Arg Gly Lys Ser Ile
            820                 825                 830

Val Ser Leu Glu Leu Thr Thr Cys Val Ser Asp Val Thr Ala Val Ile
            835                 840                 845

Leu Phe Phe Phe Thr Phe Phe Ile Thr Thr Met Val Met Leu Ala Ala
850                 855                 860

Leu Ala His His Leu Phe Tyr Trp Asp Val Trp Phe Ile Tyr Asn Val
865                 870                 875                 880

Cys Leu Ala Lys Ile Lys Gly Tyr Arg Ser Leu Ser Thr Ser Gln Thr
                885                 890                 895

Phe Tyr Asp Ala Tyr Ile Ser Tyr Asp Thr Lys Asp Ala Ser Val Thr
            900                 905                 910

Asp Trp Val Ile Asn Glu Leu Arg Tyr His Leu Glu Glu Ser Arg Asp
            915                 920                 925

Lys Asn Val Leu Leu Cys Leu Glu Glu Arg Asp Trp Asp Pro Gly Leu
            930                 935                 940

Ala Ile Ile Asp Asn Leu Met Gln Ser Ile Asn Gln Ser Lys Lys Thr
945                 950                 955                 960

Val Phe Val Leu Thr Lys Lys Tyr Ala Lys Ser Trp Asn Phe Lys Thr
                965                 970                 975

Ala Phe Tyr Leu Ala Leu Gln Arg Leu Met Asp Glu Asn Met Asp Val
            980                 985                 990

Ile Ile Phe Ile Leu Leu Glu Pro Val Leu Gln His Ser Gln Tyr Leu
            995                 1000                1005

Arg Leu Arg Gln Arg Ile Cys Lys Ser Ser Ile Leu Gln Trp Pro
        1010                1015                1020

Asp Asn Pro Lys Ala Glu Gly Leu Phe Trp Gln Thr Leu Arg Asn
        1025                1030                1035

Val Val Leu Thr Glu Asn Asp Ser Arg Tyr Asn Asn Met Tyr Val
        1040                1045                1050

Asp Ser Ile Lys Gln Tyr
        1055

<210> SEQ ID NO 11
<211> LENGTH: 1032
<212> TYPE: PRT
<213> ORGANISM: Homo sapiens

<400> SEQUENCE: 11

Met Gly Phe Cys Arg Ser Ala Leu His Pro Leu Ser Leu Leu Val Gln
1               5                   10                  15

Ala Ile Met Leu Ala Met Thr Leu Ala Leu Gly Thr Leu Pro Ala Phe
            20                  25                  30

Leu Pro Cys Glu Leu Gln Pro His Gly Leu Val Asn Cys Asn Trp Leu
            35                  40                  45

Phe Leu Lys Ser Val Pro His Phe Ser Met Ala Ala Pro Arg Gly Asn
        50                  55                  60

Val Thr Ser Leu Ser Leu Ser Ser Asn Arg Ile His His Leu His Asp
65                  70                  75                  80

Ser Asp Phe Ala His Leu Pro Ser Leu Arg His Leu Asn Leu Lys Trp
                85                  90                  95

Asn Cys Pro Pro Val Gly Leu Ser Pro Met His Phe Pro Cys His Met
            100                 105                 110
```

```
Thr Ile Glu Pro Ser Thr Phe Leu Ala Val Pro Thr Leu Glu Glu Leu
        115                 120                 125

Asn Leu Ser Tyr Asn Asn Ile Met Thr Val Pro Ala Leu Pro Lys Ser
130                 135                 140

Leu Ile Ser Leu Ser Leu Ser His Thr Asn Ile Leu Met Leu Asp Ser
145                 150                 155                 160

Ala Ser Leu Ala Gly Leu His Ala Leu Arg Phe Leu Phe Met Asp Gly
                165                 170                 175

Asn Cys Tyr Tyr Lys Asn Pro Cys Arg Gln Ala Leu Glu Val Ala Pro
                180                 185                 190

Gly Ala Leu Leu Gly Leu Gly Asn Leu Thr His Leu Ser Leu Lys Tyr
            195                 200                 205

Asn Asn Leu Thr Val Val Pro Arg Asn Leu Pro Ser Ser Leu Glu Tyr
        210                 215                 220

Leu Leu Leu Ser Tyr Asn Arg Ile Val Lys Leu Ala Pro Glu Asp Leu
225                 230                 235                 240

Ala Asn Leu Thr Ala Leu Arg Val Leu Asp Val Gly Gly Asn Cys Arg
                245                 250                 255

Arg Cys Asp His Ala Pro Asn Pro Cys Met Glu Cys Pro Arg His Phe
                260                 265                 270

Pro Gln Leu His Pro Asp Thr Phe Ser His Leu Ser Arg Leu Glu Gly
            275                 280                 285

Leu Val Leu Lys Asp Ser Ser Leu Ser Trp Leu Asn Ala Ser Trp Phe
        290                 295                 300

Arg Gly Leu Gly Asn Leu Arg Val Leu Asp Leu Ser Glu Asn Phe Leu
305                 310                 315                 320

Tyr Lys Cys Ile Thr Lys Thr Lys Ala Phe Gln Gly Leu Thr Gln Leu
                325                 330                 335

Arg Lys Leu Asn Leu Ser Phe Asn Tyr Gln Lys Arg Val Ser Phe Ala
            340                 345                 350

His Leu Ser Leu Ala Pro Ser Phe Gly Ser Leu Val Ala Leu Lys Glu
        355                 360                 365

Leu Asp Met His Gly Ile Phe Phe Arg Ser Leu Asp Glu Thr Thr Leu
        370                 375                 380

Arg Pro Leu Ala Arg Leu Pro Met Leu Gln Thr Leu Arg Leu Gln Met
385                 390                 395                 400

Asn Phe Ile Asn Gln Ala Gln Leu Gly Ile Phe Arg Ala Phe Pro Gly
                405                 410                 415

Leu Arg Tyr Val Asp Leu Ser Asp Asn Arg Ile Ser Gly Ala Ser Glu
                420                 425                 430

Leu Thr Ala Thr Met Gly Glu Ala Asp Gly Gly Glu Lys Val Trp Leu
            435                 440                 445

Gln Pro Gly Asp Leu Ala Pro Ala Pro Val Asp Thr Pro Ser Ser Glu
        450                 455                 460

Asp Phe Arg Pro Asn Cys Ser Thr Leu Asn Phe Thr Leu Asp Leu Ser
465                 470                 475                 480

Arg Asn Asn Leu Val Thr Val Gln Pro Glu Met Phe Ala Gln Leu Ser
                485                 490                 495

His Leu Gln Cys Leu Arg Leu Ser His Asn Cys Ile Ser Gln Ala Val
                500                 505                 510

Asn Gly Ser Gln Phe Leu Pro Leu Thr Gly Leu Gln Val Leu Asp Leu
            515                 520                 525
```

```
Ser Arg Asn Lys Leu Asp Leu Tyr His Glu His Ser Phe Thr Glu Leu
    530                 535                 540

Pro Arg Leu Glu Ala Leu Asp Leu Ser Tyr Asn Ser Gln Pro Phe Gly
545                 550                 555                 560

Met Gln Gly Val Gly His Asn Phe Ser Phe Val Ala His Leu Arg Thr
                565                 570                 575

Leu Arg His Leu Ser Leu Ala His Asn Asn Ile His Ser Gln Val Ser
            580                 585                 590

Gln Gln Leu Cys Ser Thr Ser Leu Arg Ala Leu Asp Phe Ser Gly Asn
        595                 600                 605

Ala Leu Gly His Met Trp Ala Glu Gly Asp Leu Tyr Leu His Phe Phe
    610                 615                 620

Gln Gly Leu Ser Gly Leu Ile Trp Leu Asp Leu Ser Gln Asn Arg Leu
625                 630                 635                 640

His Thr Leu Leu Pro Gln Thr Leu Arg Asn Leu Pro Lys Ser Leu Gln
                645                 650                 655

Val Leu Arg Leu Arg Asp Asn Tyr Leu Ala Phe Phe Lys Trp Trp Ser
            660                 665                 670

Leu His Phe Leu Pro Lys Leu Glu Val Leu Asp Leu Ala Gly Asn Arg
        675                 680                 685

Leu Lys Ala Leu Thr Asn Gly Ser Leu Pro Ala Gly Thr Arg Leu Arg
    690                 695                 700

Arg Leu Asp Val Ser Cys Asn Ser Ile Ser Phe Val Ala Pro Gly Phe
705                 710                 715                 720

Phe Ser Lys Ala Lys Glu Leu Arg Glu Leu Asn Leu Ser Ala Asn Ala
                725                 730                 735

Leu Lys Thr Val Asp His Ser Trp Phe Gly Pro Leu Ala Ser Ala Leu
            740                 745                 750

Gln Ile Leu Asp Val Ser Ala Asn Pro Leu His Cys Ala Cys Gly Ala
        755                 760                 765

Ala Phe Met Asp Phe Leu Leu Glu Val Gln Ala Ala Val Pro Gly Leu
    770                 775                 780

Pro Ser Arg Val Lys Cys Gly Ser Pro Gly Gln Leu Gln Gly Leu Ser
785                 790                 795                 800

Ile Phe Ala Gln Asp Leu Arg Leu Cys Leu Asp Glu Ala Leu Ser Trp
                805                 810                 815

Asp Cys Phe Ala Leu Ser Leu Leu Ala Val Ala Leu Gly Leu Gly Val
            820                 825                 830

Pro Met Leu His His Leu Cys Gly Trp Asp Leu Trp Tyr Cys Phe His
    835                 840                 845

Leu Cys Leu Ala Trp Leu Pro Trp Arg Gly Arg Gln Ser Gly Arg Asp
850                 855                 860

Glu Asp Ala Leu Pro Tyr Asp Ala Phe Val Val Phe Asp Lys Thr Gln
865                 870                 875                 880

Ser Ala Val Ala Asp Trp Val Tyr Asn Glu Leu Arg Gly Gln Leu Glu
                885                 890                 895

Glu Cys Arg Gly Arg Trp Ala Leu Arg Leu Cys Leu Glu Glu Arg Asp
            900                 905                 910

Trp Leu Pro Gly Lys Thr Leu Phe Glu Asn Leu Trp Ala Ser Val Tyr
        915                 920                 925

Gly Ser Arg Lys Thr Leu Phe Val Leu Ala His Thr Asp Arg Val Ser
    930                 935                 940
```

Gly Leu Leu Arg Ala Ser Phe Leu Leu Ala Gln Gln Arg Leu Leu Glu
945                 950                 955                 960

Asp Arg Lys Asp Val Val Leu Val Ile Leu Ser Pro Asp Gly Arg
            965                 970                 975

Arg Ser Arg Tyr Val Arg Leu Arg Gln Arg Leu Cys Arg Gln Ser Val
            980                 985                 990

Leu Leu Trp Pro His Gln Pro Ser Gly Gln Arg Ser Phe Trp Ala Gln
        995                 1000                1005

Leu Gly Met Ala Leu Thr Arg Asp Asn His His Phe Tyr Asn Arg
    1010                1015                1020

Asn Phe Cys Gln Gly Pro Thr Ala Glu
    1025                1030

<210> SEQ ID NO 12
<211> LENGTH: 811
<212> TYPE: PRT
<213> ORGANISM: Homo sapiens

<400> SEQUENCE: 12

Met Arg Leu Ile Arg Asn Ile Tyr Ile Phe Cys Ser Ile Val Met Thr
1               5                   10                  15

Ala Glu Gly Asp Ala Pro Glu Leu Pro Glu Arg Glu Leu Met Thr
            20                  25                  30

Asn Cys Ser Asn Met Ser Leu Arg Lys Val Pro Ala Asp Leu Thr Pro
        35                  40                  45

Ala Thr Thr Thr Leu Asp Leu Ser Tyr Asn Leu Leu Phe Gln Leu Gln
    50                  55                  60

Ser Ser Asp Phe His Ser Val Ser Lys Leu Arg Val Leu Ile Leu Cys
65                  70                  75                  80

His Asn Arg Ile Gln Gln Leu Asp Leu Lys Thr Phe Glu Phe Asn Lys
                85                  90                  95

Glu Leu Arg Tyr Leu Asp Leu Ser Asn Asn Arg Leu Lys Ser Val Thr
            100                 105                 110

Trp Tyr Leu Leu Ala Gly Leu Arg Tyr Leu Asp Leu Ser Phe Asn Asp
        115                 120                 125

Phe Asp Thr Met Pro Ile Cys Glu Glu Ala Gly Asn Met Ser His Leu
130                 135                 140

Glu Ile Leu Gly Leu Ser Gly Ala Lys Ile Gln Lys Ser Asp Phe Gln
145                 150                 155                 160

Lys Ile Ala His Leu His Leu Asn Thr Val Phe Leu Gly Phe Arg Thr
                165                 170                 175

Leu Pro His Tyr Glu Glu Gly Ser Leu Pro Ile Leu Asn Thr Thr Lys
            180                 185                 190

Leu His Ile Val Leu Pro Met Asp Thr Asn Phe Trp Val Leu Leu Arg
        195                 200                 205

Asp Gly Ile Lys Thr Ser Lys Ile Leu Glu Met Thr Asn Ile Asp Gly
210                 215                 220

Lys Ser Gln Phe Val Ser Tyr Glu Met Gln Arg Asn Leu Ser Leu Glu
225                 230                 235                 240

Asn Ala Lys Thr Ser Val Leu Leu Leu Asn Lys Val Asp Leu Leu Trp
                245                 250                 255

Asp Asp Leu Phe Leu Ile Leu Gln Phe Val Trp His Thr Ser Val Glu
            260                 265                 270

His Phe Gln Ile Arg Asn Val Thr Phe Gly Gly Lys Ala Tyr Leu Asp
        275                 280                 285

-continued

```
His Asn Ser Phe Asp Tyr Ser Asn Thr Val Met Arg Thr Ile Lys Leu
    290                 295                 300

Glu His Val His Phe Arg Val Phe Tyr Ile Gln Gln Asp Lys Ile Tyr
305                 310                 315                 320

Leu Leu Leu Thr Lys Met Asp Ile Glu Asn Leu Thr Ile Ser Asn Ala
                325                 330                 335

Gln Met Pro His Met Leu Phe Pro Asn Tyr Pro Thr Lys Phe Gln Tyr
                340                 345                 350

Leu Asn Phe Ala Asn Asn Ile Leu Thr Asp Glu Leu Phe Lys Arg Thr
                355                 360                 365

Ile Gln Leu Pro His Leu Lys Thr Leu Ile Leu Asn Gly Asn Lys Leu
    370                 375                 380

Glu Thr Leu Ser Leu Val Ser Cys Phe Ala Asn Asn Thr Pro Leu Glu
385                 390                 395                 400

His Leu Asp Leu Ser Gln Asn Leu Leu Gln His Lys Asn Asp Glu Asn
                405                 410                 415

Cys Ser Trp Pro Glu Thr Val Val Asn Met Asn Leu Ser Tyr Asn Lys
                420                 425                 430

Leu Ser Asp Ser Val Phe Arg Cys Leu Pro Lys Ser Ile Gln Ile Leu
            435                 440                 445

Asp Leu Asn Asn Asn Gln Ile Gln Thr Val Pro Lys Glu Thr Ile His
450                 455                 460

Leu Met Ala Leu Arg Glu Leu Asn Ile Ala Phe Asn Phe Leu Thr Asp
465                 470                 475                 480

Leu Pro Gly Cys Ser His Phe Ser Arg Leu Ser Val Leu Asn Ile Glu
                485                 490                 495

Met Asn Phe Ile Leu Ser Pro Ser Leu Asp Phe Val Gln Ser Cys Gln
                500                 505                 510

Glu Val Lys Thr Leu Asn Ala Gly Arg Asn Pro Phe Arg Cys Thr Cys
            515                 520                 525

Glu Leu Lys Asn Phe Ile Gln Leu Glu Thr Tyr Ser Glu Val Met Met
530                 535                 540

Val Gly Trp Ser Asp Ser Tyr Thr Cys Glu Tyr Pro Leu Asn Leu Arg
545                 550                 555                 560

Gly Ile Arg Leu Lys Asp Val His Leu His Glu Leu Ser Cys Asn Thr
                565                 570                 575

Ala Leu Leu Ile Val Thr Ile Val Ile Met Leu Val Leu Gly Leu
                580                 585                 590

Ala Val Ala Phe Cys Cys Leu His Phe Asp Leu Pro Trp Tyr Leu Arg
            595                 600                 605

Met Leu Gly Gln Cys Thr Gln Thr Trp His Arg Val Arg Lys Thr Thr
    610                 615                 620

Gln Glu Gln Leu Lys Arg Asn Val Arg Phe His Ala Phe Ile Ser Tyr
625                 630                 635                 640

Ser Glu His Asp Ser Leu Trp Val Lys Asn Glu Leu Ile Pro Asn Leu
                645                 650                 655

Glu Lys Glu Asp Gly Ser Ile Leu Ile Cys Leu Tyr Glu Ser Tyr Phe
                660                 665                 670

Asp Pro Gly Lys Ser Ile Ser Glu Asn Ile Val Ser Phe Ile Glu Lys
            675                 680                 685

Ser Tyr Lys Ser Ile Phe Val Leu Ser Pro Asn Phe Val Gln Asn Glu
    690                 695                 700
```

```
Trp Cys His Tyr Glu Phe Tyr Phe Ala His His Asn Leu Phe His Glu
705                 710                 715                 720

Asn Ser Asp His Ile Ile Leu Ile Leu Leu Glu Pro Ile Pro Phe Tyr
                725                 730                 735

Cys Ile Pro Thr Arg Tyr His Lys Leu Lys Ala Leu Leu Glu Lys Lys
            740                 745                 750

Ala Tyr Leu Glu Trp Pro Lys Asp Arg Arg Lys Cys Gly Leu Phe Trp
        755                 760                 765

Ala Asn Leu Arg Ala Ala Ile Asn Val Asn Val Leu Ala Thr Arg Glu
    770                 775                 780

Met Tyr Glu Leu Gln Thr Phe Thr Glu Leu Asn Glu Glu Ser Arg Gly
785                 790                 795                 800

Ser Thr Ile Ser Leu Met Arg Thr Asp Cys Leu
                805                 810

<210> SEQ ID NO 13
<211> LENGTH: 926
<212> TYPE: PRT
<213> ORGANISM: Mus musculus

<400> SEQUENCE: 13

Met Pro Arg Met Glu Arg His Gln Phe Cys Ser Val Leu Leu Ile Leu
1               5                   10                  15

Ile Leu Leu Thr Leu Val Ser Leu Thr Leu Thr Gly Trp Ala Trp Thr
                20                  25                  30

Ile Pro Asp Cys Ile Ile Ala Asp Ser Leu Leu Phe Pro Asn Leu Ser
                35                  40                  45

Tyr Tyr Ile Pro Phe Cys Thr Ser Ala Pro Gly Leu His Leu Leu Ala
        50                  55                  60

Ser Cys Ser Asn Val Lys Asn Leu Asn Gln Thr Leu Lys Arg Val Pro
65                  70                  75                  80

Arg Asn Thr Glu Val Leu Cys Leu Gln Gly Met Val Pro Thr Leu Pro
                85                  90                  95

Ala Lys Ala Phe Ile Arg Phe His Ser Leu Gln Leu Leu Arg Leu Gln
            100                 105                 110

Leu Ser Thr Thr Ser Val Thr Ser Arg Thr Phe Gln Gly Leu Asp Gln
        115                 120                 125

Leu Gln Tyr Leu Phe Phe Asp His His Ala Pro Cys Cys Leu Ser Leu
    130                 135                 140

Phe Leu Ser Pro Asn Cys Phe Glu Ser Leu Arg Ser Leu Ser Ser Leu
145                 150                 155                 160

Ser Phe Gln Gly Tyr Cys Leu Thr Tyr Ser Gln Ser Ile Tyr Leu Pro
                165                 170                 175

Thr Ser Leu Arg His Leu Thr Leu Arg Asn Ser Cys Leu Thr Lys Phe
            180                 185                 190

Gln Asp Leu Gln Arg Leu Phe Pro Asp Leu Leu Leu Ser Thr Ser Ser
        195                 200                 205

Thr Pro Asn Thr Lys Pro Gly Ala Pro Phe Leu Glu Met Leu Asp Leu
    210                 215                 220

Ser Tyr Asn Leu Gln Leu Lys Gln Ala Gly Val Arg Asp Leu Tyr Gly
225                 230                 235                 240

Leu Thr Leu His Ser Leu Ile Leu Asp Gly Thr Pro Leu Arg Ala Leu
                245                 250                 255

Asp Leu Thr Asp Ser Gly Leu Leu His Leu His Phe Leu Ser Leu Val
            260                 265                 270
```

```
Gly Thr Gly Ile Glu Lys Val Pro Ala Ser Leu Thr Gly Tyr Ser Glu
            275                 280                 285
Leu Arg Ala Leu Asp Leu Gly Lys Asn Gln Ile Gln Asn Ile Leu Glu
    290                 295                 300
Asn Gly Glu Ile Pro Gly Tyr Lys Ala Leu Glu Phe Leu Ser Leu His
305                 310                 315                 320
Asp Asn His Leu Gln Thr Leu Pro Thr Arg Phe Leu His Thr Leu Pro
                325                 330                 335
Gln Leu Gln Lys Leu Asn Leu Ser Met Asn Lys Leu Gly Pro Ile Leu
            340                 345                 350
Glu Leu Pro Glu Gly Leu Phe Ser Thr Asn Leu Lys Val Leu Asp Leu
        355                 360                 365
Ser His Asn Gln Leu Cys Asp Val Pro His Gly Ala Phe Ser Leu Leu
370                 375                 380
Ser Gln Leu Gln Glu Leu Trp Leu Ser Gly Asn Asn Ile Ser Ser Leu
385                 390                 395                 400
Ser Asn Glu Ser Leu Gln Gly Leu Arg Gln Leu Arg Thr Leu Asp Leu
                405                 410                 415
Ser Trp Asn Gln Ile Lys Val Leu Lys Pro Gly Trp Leu Ser His Leu
            420                 425                 430
Pro Ala Leu Thr Thr Leu Asn Leu Leu Gly Thr Tyr Leu Glu Asn Ile
        435                 440                 445
Leu Gly Ile Gln Leu Gln Gly Pro Lys Met Leu Arg His Leu Gln Leu
    450                 455                 460
Gly Ser Tyr Pro Met Leu Asp Ile Tyr Pro Trp Pro Thr Leu
465                 470                 475                 480
Leu Ser Leu Glu Ile Gln Ala Glu Ser Cys Ile Gln Phe Met Ile His
                485                 490                 495
Ser Gly Gln Pro Phe Leu Phe Leu Glu Asn Leu Thr Leu Glu Thr Ser
            500                 505                 510
Ile Leu Leu Leu Lys Pro Asp Asn Ile Thr Ile His Phe Pro Ser Leu
        515                 520                 525
Arg Arg Leu Thr Leu Arg Gly Tyr Ser Phe Ile Phe Ser Thr Ser Gln
    530                 535                 540
Leu Gln Arg Phe Phe Pro Gln Gln Leu Pro Leu Leu Glu His Phe Phe
545                 550                 555                 560
Ile Trp Cys Glu Asn Ser Tyr Ala Val Asp Leu Tyr Leu Phe Gly Met
                565                 570                 575
Pro Arg Leu Arg Val Leu Glu Leu Gly Tyr Leu Asn Phe Phe Tyr Glu
            580                 585                 590
Ser Ser Thr Met Lys Leu Glu Met Leu Leu Lys Glu Val Pro Gln Leu
        595                 600                 605
Gln Val Leu Ala Leu Ser His Leu Asn Leu Arg Asn Leu Ser Val Ser
    610                 615                 620
Ser Phe Lys Ser Leu Gln Asp Leu Lys Leu Leu Phe Asn Ser Glu
625                 630                 635                 640
Arg Ala Leu Glu Met Asn Ser Asn Leu Gln Glu Phe Ile Pro Gln Met
                645                 650                 655
Pro Gln Tyr Val Tyr Phe Ser Asp Val Thr Phe Thr Cys Gln Cys Glu
            660                 665                 670
Ala Ser Trp Leu Glu Ser Trp Ala Thr Arg Ala Pro Asn Thr Phe Val
        675                 680                 685
```

Tyr Gly Leu Glu Lys Ser Ile Cys Ile Ala Asn Ala Ser Asp Tyr Ser
        690                 695                 700

Lys Thr Leu Leu Phe Ser Phe Leu Ala Thr Asn Cys Pro His Gly Thr
705                 710                 715                 720

Glu Phe Trp Gly Phe Leu Thr Ser Phe Ile Leu Leu Leu Leu Leu Ile
                725                 730                 735

Ile Leu Pro Leu Ile Ser Cys Pro Lys Trp Ser Trp Leu His His Leu
            740                 745                 750

Trp Thr Leu Phe His Thr Cys Trp Trp Lys Leu Cys Gly His Arg Leu
        755                 760                 765

Arg Gly Gln Phe Asn Tyr Asp Val Phe Ile Ser Tyr Cys Glu Glu Asp
770                 775                 780

Gln Ala Trp Val Leu Glu Leu Val Pro Val Leu Glu Lys Ala Pro
785                 790                 795                 800

Pro Glu Gly Glu Gly Leu Arg Leu Cys Leu Pro Ala Arg Asp Phe Gly
                805                 810                 815

Ile Gly Asn Asp Arg Met Glu Ser Met Ile Ala Ser Met Gly Lys Ser
            820                 825                 830

Arg Ala Thr Leu Cys Val Leu Thr Gly Gln Ala Leu Ala Ser Pro Trp
        835                 840                 845

Cys Asn Leu Glu Leu Arg Leu Ala Thr Tyr His Leu Val Ala Arg Pro
850                 855                 860

Gly Thr Thr His Leu Leu Leu Phe Leu Glu Pro Leu Asp Arg Gln
865                 870                 875                 880

Arg Leu His Ser Tyr His Arg Leu Ser Arg Trp Leu Gln Lys Glu Asp
                885                 890                 895

Tyr Phe Asp Leu Ser Gln Gly Lys Val Glu Trp Asn Ser Phe Cys Glu
            900                 905                 910

Gln Leu Lys Arg Arg Leu Ser Lys Ala Gly Gln Glu Arg Asp
        915                 920                 925

<210> SEQ ID NO 14
<211> LENGTH: 906
<212> TYPE: PRT
<213> ORGANISM: Mus musculus

<400> SEQUENCE: 14

Met Gly Arg Tyr Trp Leu Leu Pro Gly Leu Leu Leu Ser Leu Pro Leu
1               5                   10                  15

Val Thr Gly Trp Ser Thr Ser Asn Cys Leu Val Thr Glu Gly Ser Arg
            20                  25                  30

Leu Pro Leu Val Ser Arg Tyr Phe Thr Phe Cys Arg His Ser Lys Leu
        35                  40                  45

Ser Phe Leu Ala Ala Cys Leu Ser Val Ser Asn Leu Thr Gln Thr Leu
    50                  55                  60

Glu Val Val Pro Arg Thr Val Glu Gly Leu Cys Leu Gly Gly Thr Val
65                  70                  75                  80

Ser Thr Leu Leu Pro Asp Ala Phe Ser Ala Phe Pro Gly Leu Lys Val
                85                  90                  95

Leu Ala Leu Ser Leu His Leu Thr Gln Leu Leu Pro Gly Ala Leu Arg
            100                 105                 110

Gly Leu Gly Gln Leu Gln Ser Leu Ser Phe Phe Asp Ser Pro Leu Arg
        115                 120                 125

Arg Ser Leu Phe Leu Pro Pro Asp Ala Phe Ser Asp Leu Ile Ser Leu
    130                 135                 140

-continued

```
Gln Arg Leu His Ile Ser Gly Pro Cys Leu Asp Lys Lys Ala Gly Ile
145                 150                 155                 160

Arg Leu Pro Pro Gly Leu Gln Trp Leu Gly Val Thr Leu Ser Cys Ile
                165                 170                 175

Gln Asp Val Gly Glu Leu Ala Gly Met Phe Pro Asp Leu Val Gln Gly
            180                 185                 190

Ser Ser Ser Arg Val Ser Trp Thr Leu Gln Lys Leu Asp Leu Ser Ser
        195                 200                 205

Asn Trp Lys Leu Lys Met Ala Ser Pro Gly Ser Leu Gln Gly Leu Gln
210                 215                 220

Val Glu Ile Leu Asp Leu Thr Arg Thr Pro Leu Asp Ala Val Trp Leu
225                 230                 235                 240

Lys Gly Leu Gly Leu Gln Lys Leu Asp Val Leu Tyr Ala Gln Thr Ala
                245                 250                 255

Thr Ala Glu Leu Ala Ala Glu Ala Val Ala His Phe Glu Leu Gln Gly
            260                 265                 270

Leu Ile Val Lys Glu Ser Lys Ile Gly Ser Ile Ser Gln Glu Ala Leu
        275                 280                 285

Ala Ser Cys His Ser Leu Lys Thr Leu Gly Leu Ser Ser Thr Gly Leu
290                 295                 300

Thr Lys Leu Pro Pro Gly Phe Leu Thr Ala Met Pro Arg Leu Gln Arg
305                 310                 315                 320

Leu Glu Leu Ser Gly Asn Gln Leu Gln Ser Ala Val Leu Cys Met Asn
                325                 330                 335

Glu Thr Gly Asp Val Ser Gly Leu Thr Thr Leu Asp Leu Ser Gly Asn
            340                 345                 350

Arg Leu Arg Ile Leu Pro Pro Ala Ala Phe Ser Cys Leu Pro His Leu
        355                 360                 365

Arg Glu Leu Leu Leu Arg Tyr Asn Gln Leu Leu Ser Leu Glu Gly Tyr
370                 375                 380

Leu Phe Gln Glu Leu Gln Gln Leu Glu Thr Leu Lys Leu Asp Gly Asn
385                 390                 395                 400

Pro Leu Leu His Leu Gly Lys Asn Trp Leu Ala Ala Leu Pro Ala Leu
                405                 410                 415

Thr Thr Leu Ser Leu Leu Asp Thr Gln Ile Arg Met Ser Pro Glu Pro
            420                 425                 430

Gly Phe Trp Gly Ala Lys Asn Leu His Thr Leu Ser Leu Lys Leu Pro
        435                 440                 445

Ala Leu Pro Ala Pro Ala Val Leu Phe Leu Pro Met Tyr Leu Thr Ser
450                 455                 460

Leu Glu Leu His Ile Ala Ser Gly Thr Thr Glu His Trp Thr Leu Ser
465                 470                 475                 480

Pro Ala Ile Phe Pro Ser Leu Glu Thr Leu Thr Ile Ser Gly Gly Gly
                485                 490                 495

Leu Lys Leu Lys Leu Gly Ser Gln Asn Ala Ser Gly Val Phe Pro Ala
            500                 505                 510

Leu Gln Lys Leu Ser Leu Leu Lys Asn Ser Leu Asp Ala Phe Cys Ser
        515                 520                 525

Gln Gly Thr Ser Asn Leu Phe Leu Trp Gln Leu Pro Lys Leu Gln Ser
530                 535                 540

Leu Arg Val Trp Gly Ala Gly Asn Ser Ser Arg Pro Cys Leu Ile Thr
545                 550                 555                 560
```

Gly Leu Pro Ser Leu Arg Glu Leu Lys Leu Ala Ser Leu Gln Ser Ile
565 570 575

Thr Gln Pro Arg Ser Val Gln Leu Glu Glu Leu Val Gly Asp Leu Pro
580 585 590

Gln Leu Gln Ala Leu Val Leu Ser Ser Thr Gly Leu Lys Ser Leu Ser
595 600 605

Ala Ala Ala Phe Gln Arg Leu His Ser Leu Gln Val Leu Val Leu Glu
610 615 620

Tyr Glu Lys Asp Leu Met Leu Gln Asp Ser Leu Arg Glu Tyr Ser Pro
625 630 635 640

Gln Met Pro His Tyr Ile Tyr Ile Leu Glu Ser Asn Leu Ala Cys His
645 650 655

Cys Ala Asn Ala Trp Met Glu Pro Trp Val Lys Arg Ser Thr Lys Thr
660 665 670

Tyr Ile Tyr Ile Arg Asp Asn Arg Leu Cys Pro Gly Gln Asp Arg Leu
675 680 685

Ser Ala Arg Gly Ser Leu Pro Ser Phe Leu Trp Asp His Cys Pro Gln
690 695 700

Thr Leu Glu Leu Lys Leu Phe Leu Ala Ser Ser Ala Leu Val Phe Met
705 710 715 720

Leu Ile Ala Leu Pro Leu Leu Gln Glu Ala Arg Asn Ser Trp Ile Pro
725 730 735

Tyr Leu Gln Ala Leu Phe Arg Val Trp Leu Gln Gly Leu Arg Gly Lys
740 745 750

Gly Asp Lys Gly Lys Arg Phe Leu Phe Asp Val Phe Val Ser His Cys
755 760 765

Arg Gln Asp Gln Gly Trp Val Ile Glu Glu Leu Leu Pro Ala Leu Glu
770 775 780

Gly Phe Leu Pro Ala Gly Leu Gly Leu Arg Leu Cys Leu Pro Glu Arg
785 790 795 800

Asp Phe Glu Pro Gly Lys Asp Val Val Asp Asn Val Val Asp Ser Met
805 810 815

Leu Ser Ser Arg Thr Thr Leu Cys Val Leu Ser Gly Gln Ala Leu Cys
820 825 830

Asn Pro Arg Cys Arg Leu Glu Leu Arg Leu Ala Thr Ser Leu Leu Leu
835 840 845

Ala Ala Pro Ser Pro Val Leu Leu Val Phe Leu Glu Pro Ile
850 855 860

Ser Arg His Gln Leu Pro Gly Tyr His Arg Leu Ala Arg Leu Leu Arg
865 870 875 880

Arg Gly Asp Tyr Cys Leu Trp Pro Glu Glu Glu Arg Lys Ser Gly
885 890 895

Phe Trp Thr Trp Leu Arg Ser Arg Leu Gly
900 905

<210> SEQ ID NO 15
<211> LENGTH: 991
<212> TYPE: PRT
<213> ORGANISM: Mus musculus

<400> SEQUENCE: 15

Met Ser Gly Leu Tyr Arg Ile Leu Val Gln Leu Glu Gln Ser Pro Tyr
1 5 10 15

Val Lys Thr Val Pro Leu Asn Met Arg Arg Asp Phe Phe Leu Val
20 25 30

Val Thr Trp Met Pro Lys Thr Val Lys Met Asn Gly Ser Ser Phe Val
            35                  40                  45

Pro Ser Leu Gln Leu Leu Met Leu Val Gly Phe Ser Leu Pro Pro
    50                  55                  60

Val Ala Glu Thr Tyr Gly Phe Asn Lys Cys Thr Gln Tyr Glu Phe Asp
65                  70                  75                  80

Ile His His Val Leu Cys Ile Arg Lys Ile Thr Asn Leu Thr Glu
                85                  90                  95

Ala Ile Ser Asp Ile Pro Arg Tyr Thr Thr His Leu Asn Leu Thr His
                100                 105                 110

Asn Glu Ile Gln Val Leu Pro Pro Trp Ser Phe Thr Asn Leu Ser Ala
                115                 120                 125

Leu Val Asp Leu Arg Leu Glu Trp Asn Ser Ile Trp Lys Ile Asp Glu
    130                 135                 140

Gly Ala Phe Arg Gly Leu Glu Asn Leu Thr Leu Leu Asn Leu Val Glu
145                 150                 155                 160

Asn Lys Ile Gln Ser Val Asn Asn Ser Phe Glu Gly Leu Ser Ser Leu
                165                 170                 175

Lys Thr Leu Leu Leu Ser His Asn Gln Ile Thr His Ile His Lys Asp
            180                 185                 190

Ala Phe Thr Pro Leu Ile Lys Leu Lys Tyr Leu Ser Leu Ser Arg Asn
            195                 200                 205

Asn Ile Ser Asp Phe Ser Gly Ile Leu Glu Ala Val Gln His Leu Pro
    210                 215                 220

Cys Leu Glu Arg Leu Asp Leu Thr Asn Asn Ser Ile Met Tyr Leu Asp
225                 230                 235                 240

His Ser Pro Arg Ser Leu Val Ser Leu Thr His Leu Ser Phe Glu Gly
                245                 250                 255

Asn Lys Leu Arg Glu Leu Asn Phe Ser Ala Leu Ser Leu Pro Asn Leu
                260                 265                 270

Thr Asn Leu Ser Ala Ser Arg Asn Gly Asn Lys Val Ile Gln Asn Val
    275                 280                 285

Tyr Leu Lys Thr Leu Pro Gln Leu Lys Ser Leu Asn Leu Ser Gly Thr
    290                 295                 300

Val Ile Lys Leu Glu Asn Leu Ser Ala Lys His Leu Gln Asn Leu Arg
305                 310                 315                 320

Ala Met Asp Leu Ser Asn Trp Glu Leu Arg His Gly His Leu Asp Met
                325                 330                 335

Lys Thr Val Cys His Leu Leu Gly Asn Leu Pro Lys Leu Glu Thr Leu
                340                 345                 350

Val Phe Gln Lys Asn Val Thr Asn Ala Glu Gly Ile Lys Gln Leu Ala
            355                 360                 365

Lys Cys Thr Arg Leu Leu Phe Leu Asp Leu Gly Gln Asn Ser Asp Leu
            370                 375                 380

Ile Tyr Leu Asn Asp Ser Glu Phe Asn Ala Leu Pro Ser Leu Gln Lys
385                 390                 395                 400

Leu Asn Leu Asn Lys Cys Gln Leu Ser Phe Ile Asn Asn Arg Thr Trp
                405                 410                 415

Ser Ser Leu Gln Asn Leu Thr Ser Leu Asp Leu Ser His Asn Lys Phe
                420                 425                 430

Lys Ser Phe Pro Asp Phe Ala Phe Ser Pro Leu Lys His Leu Glu Phe
            435                 440                 445

```
Leu Ser Leu Ser Arg Asn Pro Ile Thr Glu Leu Asn Asn Leu Ala Phe
450                 455                 460

Ser Gly Leu Phe Ala Leu Lys Glu Leu Asn Leu Ala Ala Cys Trp Ile
465                 470                 475                 480

Val Thr Ile Asp Arg Tyr Ser Phe Thr Gln Phe Pro Asn Leu Glu Val
                485                 490                 495

Leu Asp Leu Gly Asp Asn Asn Ile Arg Thr Leu Asn His Gly Thr Phe
                500                 505                 510

Arg Pro Leu Lys Lys Leu Gln Ser Leu Ile Leu Ser His Asn Cys Leu
                515                 520                 525

Lys Ile Leu Glu Pro Asn Ser Phe Ser Gly Leu Thr Asn Leu Arg Ser
530                 535                 540

Leu Asp Leu Met Tyr Asn Ser Leu Ser Tyr Phe His Glu His Leu Phe
545                 550                 555                 560

Ser Gly Leu Glu Lys Leu Leu Ile Leu Lys Leu Gly Phe Asn Lys Ile
                565                 570                 575

Thr Tyr Glu Thr Thr Arg Thr Leu Gln Tyr Pro Pro Phe Ile Lys Leu
                580                 585                 590

Lys Ser Leu Lys Gln Leu Asn Leu Glu Gly Gln Arg His Gly Ile Gln
                595                 600                 605

Val Val Pro Ser Asn Phe Phe Gln Gly Leu Gly Ser Leu Gln Glu Leu
                610                 615                 620

Leu Leu Gly Lys Asn Pro Ser Val Phe Leu Asp His His Gln Phe Asp
625                 630                 635                 640

Pro Leu Ile Asn Leu Thr Lys Leu Asp Ile Ser Gly Thr Lys Asp Gly
                645                 650                 655

Asp Arg Ser Leu Tyr Leu Asn Ala Ser Leu Phe Gln Asn Leu Lys Arg
                660                 665                 670

Leu Lys Ile Leu Arg Leu Glu Asn Asn Asn Leu Glu Ser Leu Val Pro
                675                 680                 685

Asp Met Phe Ser Ser Leu Gln Ser Leu Gln Val Phe Ser Leu Arg Phe
                690                 695                 700

Asn Asn Leu Lys Val Ile Asn Gln Ser His Leu Lys Asn Leu Lys Ser
705                 710                 715                 720

Leu Met Phe Phe Asp Val Tyr Gly Asn Lys Leu Gln Cys Thr Cys Asp
                725                 730                 735

Asn Leu Trp Phe Lys Asn Trp Ser Met Asn Thr Glu Glu Val His Ile
                740                 745                 750

Pro Phe Leu Arg Ser Tyr Pro Cys Gln Gln Pro Gly Ser Gln Ser Leu
                755                 760                 765

Leu Ile Asp Phe Asp Asp Ala Met Cys Asn Phe Asp Leu Gly Lys Val
                770                 775                 780

Tyr Phe Leu Cys Ser Phe Ser Met Val Leu Ser Thr Met Val Phe Ser
785                 790                 795                 800

Trp Phe Ser Thr Lys Met Ile Ala Ser Leu Trp Tyr Gly Leu Tyr Ile
                805                 810                 815

Cys Arg Ala Trp Tyr Leu Thr Lys Trp His Lys Thr Glu Lys Lys Phe
                820                 825                 830

Leu Tyr Asp Ala Phe Val Ser Phe Ser Ala Thr Asp Glu Ala Trp Val
                835                 840                 845

Tyr Lys Glu Leu Val Pro Ala Leu Glu Gln Gly Ser Gln Thr Thr Phe
850                 855                 860
```

```
Lys Leu Cys Leu His Gln Arg Asp Phe Glu Pro Gly Ile Asp Ile Phe
865                 870                 875                 880

Glu Asn Ile Gln Asn Ala Ile Asn Thr Ser Arg Lys Thr Leu Cys Val
            885                 890                 895

Val Ser Asn His Tyr Leu His Ser Glu Trp Cys Arg Leu Glu Val Gln
        900                 905                 910

Leu Ala Ser Met Lys Met Phe Tyr Glu His Lys Asp Val Ile Ile Leu
    915                 920                 925

Ile Phe Leu Glu Glu Ile Pro Asn Tyr Lys Leu Ser Ser Tyr His Arg
930                 935                 940

Leu Arg Lys Leu Ile Asn Lys Gln Thr Phe Ile Thr Trp Pro Asp Ser
945                 950                 955                 960

Val His Gln Gln Pro Leu Phe Trp Ala Arg Ile Arg Asn Ala Leu Gly
            965                 970                 975

Lys Glu Thr Val Glu Lys Glu Asn Thr His Leu Ile Val Val Glu
        980                 985                 990

<210> SEQ ID NO 16
<211> LENGTH: 634
<212> TYPE: PRT
<213> ORGANISM: Homo sapiens

<400> SEQUENCE: 16

Met Pro Leu Leu Leu Leu Pro Leu Leu Trp Ala Gly Ala Leu Ala
1               5                   10                  15

Glu Ser Trp Glu Pro Cys Val Glu Val Val Pro Asn Ile Thr Tyr Gln
            20                  25                  30

Cys Met Glu Leu Asn Phe Tyr Lys Ile Pro Asp Asn Leu Pro Phe Ser
        35                  40                  45

Thr Lys Asn Leu Asp Leu Ser Phe Asn Pro Leu Arg His Leu Gly Ser
    50                  55                  60

Tyr Ser Phe Phe Ser Phe Pro Glu Leu Gln Val Leu Asp Leu Ser Arg
65                  70                  75                  80

Cys Glu Ile Gln Thr Ile Glu Asp Gly Ala Tyr Gln Ser Leu Ser His
            85                  90                  95

Leu Ser Thr Leu Ile Leu Thr Gly Asn Pro Ile Gln Ser Leu Ala Leu
        100                 105                 110

Gly Ala Phe Ser Gly Leu Ser Ser Leu Gln Lys Leu Val Ala Val Glu
    115                 120                 125

Thr Asn Leu Ala Ser Leu Glu Asn Phe Pro Ile Gly His Leu Lys Thr
130                 135                 140

Leu Lys Glu Leu Asn Val Ala His Asn Leu Ile Gln Ser Phe Lys Leu
145                 150                 155                 160

Pro Glu Tyr Phe Ser Asn Leu Thr Asn Leu Glu His Leu Asp Leu Ser
            165                 170                 175

Ser Asn Lys Ile Gln Ser Ile Tyr Cys Thr Asp Leu Arg Val Leu His
        180                 185                 190

Gln Met Pro Leu Leu Asn Leu Ser Leu Asp Leu Ser Leu Asn Pro Met
    195                 200                 205

Asn Phe Ile Gln Pro Gly Ala Phe Lys Glu Ile Arg Leu His Lys Leu
210                 215                 220

Thr Leu Arg Asn Asn Phe Asp Ser Leu Asn Val Met Lys Thr Cys Ile
225                 230                 235                 240

Gln Gly Leu Ala Gly Leu Glu Val His Arg Leu Val Leu Gly Glu Phe
            245                 250                 255
```

Arg Asn Glu Gly Asn Leu Glu Lys Phe Asp Lys Ser Ala Leu Glu Gly
                260                 265                 270

Leu Cys Asn Leu Thr Ile Glu Phe Arg Leu Ala Tyr Leu Asp Tyr
        275                 280                 285

Tyr Leu Asp Asp Ile Ile Asp Leu Phe Asn Cys Leu Thr Asn Val Ser
        290                 295                 300

Ser Phe Ser Leu Val Ser Val Thr Ile Glu Arg Val Lys Asp Phe Ser
305                 310                 315                 320

Tyr Asn Phe Gly Trp Gln His Leu Glu Leu Val Asn Cys Lys Phe Gly
                325                 330                 335

Gln Phe Pro Thr Leu Lys Leu Lys Ser Leu Lys Arg Leu Thr Phe Thr
            340                 345                 350

Ser Asn Lys Gly Gly Asn Ala Phe Ser Glu Val Asp Leu Pro Ser Leu
            355                 360                 365

Glu Phe Leu Asp Leu Ser Arg Asn Gly Leu Ser Phe Lys Gly Cys Cys
        370                 375                 380

Ser Gln Ser Asp Phe Gly Thr Thr Ser Leu Lys Tyr Leu Asp Leu Ser
385                 390                 395                 400

Phe Asn Gly Val Ile Thr Met Ser Ser Asn Phe Leu Gly Leu Glu Gln
                405                 410                 415

Leu Glu His Leu Asp Phe Gln His Ser Asn Leu Lys Gln Met Ser Glu
            420                 425                 430

Phe Ser Val Phe Leu Ser Leu Arg Asn Leu Ile Tyr Leu Asp Ile Ser
        435                 440                 445

His Thr His Thr Arg Val Ala Phe Asn Gly Ile Phe Asn Gly Leu Ser
            450                 455                 460

Ser Leu Glu Val Leu Lys Met Ala Gly Asn Ser Phe Gln Glu Asn Phe
465                 470                 475                 480

Leu Pro Asp Ile Phe Thr Glu Leu Arg Asn Leu Thr Phe Leu Asp Leu
                485                 490                 495

Ser Gln Cys Gln Leu Glu Gln Leu Ser Pro Thr Ala Phe Asn Ser Leu
            500                 505                 510

Ser Ser Leu Gln Val Leu Asn Met Ser His Asn Asn Phe Phe Ser Leu
        515                 520                 525

Asp Thr Phe Pro Tyr Lys Cys Leu Asn Ser Leu Gln Val Leu Asp Tyr
        530                 535                 540

Ser Leu Asn His Ile Met Thr Ser Lys Lys Gln Glu Leu Gln His Phe
545                 550                 555                 560

Pro Ser Ser Leu Ala Phe Leu Asn Leu Thr Gln Asn Asp Phe Ala Cys
                565                 570                 575

Thr Cys Glu His Gln Ser Phe Leu Gln Trp Ile Lys Asp Gln Arg Gln
            580                 585                 590

Leu Leu Val Glu Val Glu Arg Met Glu Cys Ala Thr Pro Ser Asp Lys
        595                 600                 605

Gln Gly Met Pro Val Leu Ser Leu Asn Ile Thr Cys Gln Met Asn Lys
        610                 615                 620

His His His His His His His His
625                 630

<210> SEQ ID NO 17
<211> LENGTH: 170
<212> TYPE: PRT
<213> ORGANISM: Homo sapiens -continued

<400> SEQUENCE: 17

Met Pro Leu Leu Leu Leu Pro Leu Leu Trp Ala Gly Ala Leu Ala
1               5                   10                  15

Glu Ala Gln Lys Gln Tyr Trp Val Cys Asn Ser Ser Asp Ala Ser Ile
            20                  25                  30

Ser Tyr Thr Tyr Cys Asp Lys Met Gln Tyr Pro Ile Ser Ile Asn Val
        35                  40                  45

Asn Pro Cys Ile Glu Leu Lys Gly Ser Lys Gly Leu Leu His Ile Phe
    50                  55                  60

Tyr Ile Pro Arg Arg Asp Leu Lys Gln Leu Tyr Phe Asn Leu Tyr Ile
65                  70                  75                  80

Thr Val Asn Thr Met Asn Leu Pro Lys Arg Lys Glu Val Ile Cys Arg
                85                  90                  95

Gly Ser Asp Asp Asp Tyr Ser Phe Cys Arg Ala Leu Lys Gly Glu Thr
            100                 105                 110

Val Asn Thr Thr Ile Ser Phe Ser Phe Lys Gly Ile Lys Phe Ser Lys
        115                 120                 125

Gly Lys Tyr Lys Cys Val Val Glu Ala Ile Ser Gly Ser Pro Glu Glu
    130                 135                 140

Met Leu Phe Cys Leu Glu Phe Val Ile Leu His Gln Pro Asn Ser Asn
145                 150                 155                 160

His His His His His His His His His
                165                 170

<210> SEQ ID NO 18
<211> LENGTH: 110
<212> TYPE: PRT
<213> ORGANISM: Mus musculus

<400> SEQUENCE: 18

Ala Ser Leu Ala Val Ser Leu Gly Gln Arg Ala Thr Ile Ser Cys Arg
1               5                   10                  15

Ala Ser Glu Ser Val Asp Ile Tyr Gly Ile Ser Phe Met Asn Trp Phe
            20                  25                  30

Gln Leu Lys Pro Gly Gln Pro Pro Lys Leu Leu Ile Tyr Ala Ala Ser
        35                  40                  45

Lys Gln Gly Ser Gly Val Pro Ala Arg Phe Ser Gly Ser Gly Ser Gly
    50                  55                  60

Thr Asp Phe Ser Leu Asn Ile His Ser Met Glu Glu Asp Asp Thr Ala
65                  70                  75                  80

Met Tyr Phe Cys Gln Gln Ser Lys Glu Val Pro Arg Thr Phe Gly Gly
                85                  90                  95

Gly Thr Lys Leu Glu Ile Lys Arg Ala Asp Ala Ala Pro Thr
            100                 105                 110

<210> SEQ ID NO 19
<211> LENGTH: 360
<212> TYPE: PRT
<213> ORGANISM: Mus musculus

<400> SEQUENCE: 19

Gly Cys Thr Thr Cys Thr Thr Thr Gly Gly Cys Thr Gly Thr Gly Thr
1               5                   10                  15

Cys Thr Cys Thr Ala Gly Gly Gly Cys Ala Gly Gly Gly Cys
            20                  25                  30

```
Cys Ala Cys Cys Ala Thr Cys Thr Cys Cys Thr Gly Cys Ala Gly Ala
             35                  40                  45

Gly Cys Cys Ala Gly Cys Gly Ala Ala Ala Gly Thr Gly Thr Thr Gly
         50                  55                  60

Ala Cys Ala Thr Thr Thr Ala Thr Gly Gly Cys Ala Thr Thr Ala Gly
 65                  70                  75                  80

Thr Thr Thr Thr Ala Thr Gly Ala Ala Cys Thr Gly Gly Thr Thr Cys
                 85                  90                  95

Cys Ala Ala Cys Thr Gly Ala Ala Cys Cys Ala Gly Gly Ala Cys
            100                 105                 110

Ala Gly Cys Cys Ala Cys Cys Ala Ala Cys Thr Cys Cys Thr
         115                 120                 125

Cys Ala Thr Cys Thr Ala Thr Gly Cys Thr Gly Cys Ala Thr Cys Cys
            130                 135                 140

Ala Ala Gly Cys Ala Ala Gly Gly Ala Thr Cys Cys Gly Gly Gly Gly
145                 150                 155                 160

Thr Cys Cys Cys Thr Gly Cys Cys Ala Gly Gly Thr Thr Thr Ala Gly
                165                 170                 175

Thr Gly Gly Cys Ala Gly Thr Gly Gly Gly Thr Cys Thr Gly Gly Gly
            180                 185                 190

Ala Cys Ala Gly Ala Cys Thr Thr Cys Ala Cys Cys Cys Thr Cys Ala
        195                 200                 205

Ala Cys Ala Thr Cys Cys Ala Thr Cys Cys Thr Ala Thr Gly Gly Ala
        210                 215                 220

Gly Gly Ala Gly Gly Ala Thr Gly Ala Thr Ala Cys Thr Gly Cys Ala
225                 230                 235                 240

Ala Thr Gly Thr Ala Thr Thr Thr Cys Thr Gly Thr Cys Ala Gly Cys
                245                 250                 255

Ala Ala Ala Gly Thr Ala Ala Gly Gly Ala Gly Thr Thr Thr Cys Cys
            260                 265                 270

Thr Cys Gly Gly Ala Cys Gly Thr Thr Cys Gly Gly Thr Gly Gly Ala
        275                 280                 285

Gly Gly Cys Ala Cys Cys Ala Ala Gly Cys Thr Gly Gly Ala Ala Ala
        290                 295                 300

Thr Cys Ala Ala Ala Cys Gly Gly Gly Cys Thr Gly Ala Thr Gly Cys
305                 310                 315                 320

Thr Gly Cys Ala Cys Cys Ala Ala Cys Thr Gly Thr Ala Thr Cys Cys
                325                 330                 335

Ala Thr Cys Thr Thr Cys Cys Ala Cys Cys Ala Thr Cys Cys Ala
        340                 345                 350

Gly Thr Gly Ala Gly Cys Ala Gly
        355                 360

<210> SEQ ID NO 20
<211> LENGTH: 120
<212> TYPE: PRT
<213> ORGANISM: Mus musculus

<400> SEQUENCE: 20

Pro Glu Leu Val Lys Ser Gly Ala Ser Val Lys Ile Ser Cys Lys Ala
1               5                   10                  15

Ser Gly Tyr Ser Phe Thr Asp Tyr Asn Ile Asn Trp Val Lys Gln Ser
            20                  25                  30

Asn Gly Lys Ser Leu Glu Trp Ile Gly Leu Ile Asn Pro Asn Tyr Gly
        35                  40                  45
```

```
Thr Thr Phe Tyr Asn Gln Lys Phe Lys Gly Lys Ala Thr Leu Thr Val
             50                  55                  60

Asp Gln Ser Ser Ser Thr Ala Tyr Met Gln Leu Asn Ser Leu Thr Ser
 65                  70                  75                  80

Glu Asp Ser Ala Val Tyr Tyr Cys Ala Arg Glu Thr Leu Leu Leu Arg
                 85                  90                  95

Tyr Phe Asp Tyr Trp Gly Gln Gly Thr Thr Leu Thr Val Ser Ser Ala
            100                 105                 110

Lys Thr Thr Pro Pro Ser Val Tyr
            115                 120

<210> SEQ ID NO 21
<211> LENGTH: 390
<212> TYPE: PRT
<213> ORGANISM: Mus musculus

<400> SEQUENCE: 21

Cys Cys Thr Gly Ala Gly Cys Thr Gly Gly Thr Gly Ala Ala Gly Thr
 1               5                  10                  15

Cys Thr Gly Gly Cys Gly Cys Thr Thr Cys Ala Gly Thr Gly Ala Ala
            20                  25                  30

Gly Ala Thr Ala Thr Cys Cys Thr Gly Cys Ala Ala Gly Gly Cys Thr
            35                  40                  45

Thr Cys Thr Gly Gly Thr Thr Ala Cys Thr Cys Ala Thr Thr Cys Ala
         50                  55                  60

Cys Thr Gly Ala Cys Thr Ala Cys Ala Ala Cys Ala Thr Ala Ala Ala
 65                  70                  75                  80

Cys Thr Gly Gly Gly Thr Gly Ala Ala Gly Cys Ala Gly Ala Gly Cys
                 85                  90                  95

Ala Ala Thr Gly Gly Ala Ala Ala Gly Ala Gly Cys Cys Thr Thr Gly
                100                 105                 110

Ala Gly Thr Gly Gly Ala Thr Thr Gly Gly Ala Cys Thr Ala Ala Thr
            115                 120                 125

Thr Ala Ala Thr Cys Cys Thr Ala Ala Cys Thr Ala Thr Gly Gly Thr
            130                 135                 140

Ala Cys Thr Ala Cys Thr Thr Cys Thr Ala Cys Ala Ala Thr Cys
145                 150                 155                 160

Ala Gly Ala Ala Gly Thr Thr Cys Ala Ala Gly Gly Gly Cys Ala Ala
                165                 170                 175

Gly Gly Cys Cys Ala Cys Ala Thr Thr Gly Ala Cys Thr Gly Thr Ala
            180                 185                 190

Gly Ala Cys Cys Ala Ala Thr Cys Thr Thr Cys Cys Ala Gly Cys Ala
            195                 200                 205

Cys Ala Gly Cys Cys Thr Ala Cys Ala Thr Gly Cys Ala Gly Cys Thr
            210                 215                 220

Cys Ala Ala Cys Ala Gly Cys Cys Thr Gly Ala Cys Ala Thr Cys Thr
225                 230                 235                 240

Gly Ala Gly Gly Ala Cys Thr Cys Thr Gly Cys Ala Gly Thr Cys Thr
                245                 250                 255

Ala Thr Thr Ala Cys Thr Gly Thr Gly Cys Ala Ala Gly Ala Gly Ala
            260                 265                 270

Gly Ala Cys Thr Thr Ala Thr Thr Ala Cys Thr Ala Cys Gly Gly
            275                 280                 285
```

-continued

```
Thr Ala Cys Thr Thr Thr Gly Ala Cys Thr Ala Cys Thr Gly Gly Gly
    290                 295                 300
Gly Cys Cys Ala Ala Gly Gly Cys Ala Cys Cys Ala Cys Thr Cys Thr
305                 310                 315                 320
Cys Ala Cys Ala Gly Thr Cys Thr Cys Cys Thr Cys Ala Gly Cys Cys
                325                 330                 335
Ala Ala Ala Ala Cys Gly Ala Cys Ala Cys Cys Cys Cys Cys Ala Thr
                340                 345                 350
Cys Thr Gly Thr Cys Thr Ala Thr Cys Cys Ala Cys Thr Gly Gly Cys
        355                 360                 365
Cys Cys Cys Thr Gly Gly Ala Thr Cys Thr Gly Cys Thr Gly Cys Cys
370                 375                 380
Cys Ala Ala Ala Cys Thr
385                 390
```

US 8,841,421 B2

S100A9 INTERACTION SCREENING METHOD

CROSS-REFERENCE TO RELATED APPLICATIONS

This is a United States of America National Stage Filing of Patent Cooperation Treaty (PCT) International Application No. PCT/EP2008/003303, International Filing Date Apr. 24, 2008, Publication No. WO/2008/131908, Publication Date Nov. 6, 2008, this application claims priority to the above-referenced PCT application (i.e., PCT International Application No. PCT/EP2008/003303), and the above-referenced PCT application (i.e., PCT International Application No. PCT/EP2008/003303) is incorporated herein by referenced in its entirety. Additionally, this application claims priority to, and incorporates herein by reference in their entireties, the following four applications, which the above-referenced PCT application (i.e., PCT International Application No. PCT/EP2008/003303) claims priority to: European Patent Application 07251762.6, filed Apr. 26, 2007; U.S. Provisional Application 60/914,180, filed Apr. 26, 2007; U.S. Provisional Application 61/021,961, filed Jan. 18, 2008; and Great Britain patent application number 0801084.5, filed Jan. 21, 2008.

FIELD OF THE INVENTION

The present invention relates to novel binding interactions and to identifying a compound for use in therapy in a mammal, including in a human. In particular the compound may be for use in cancer therapy or in therapy of an autoimmune disease or inflammatory condition. Methods are provided for identifying novel S100A9 ligands, and agents that interact with S100A9 are also disclosed. The present invention also provides such ligands and agents including an antibody.

BACKGROUND OF THE INVENTION

S100A9, also known as calgranulin B and myeloid related protein-14 (MRP-14), is a calcium- and zinc-binding protein that belongs to the S 100 protein family. S100A9 is highly expressed by the myeloid cell lineage and is found in the extracellular milieu during inflammatory conditions. S100A9 forms heterodimers with S100A8, another member of the S100 family. However, S100A9 may also form monomers which executes specific functions. Human S100A9 has a molecular mass of about 13 kDa and is composed of 114 amino acid residues.

The S100A8/A9 protein can bind to endothelium through the interaction of S100A9 with heparan sulphate proteoglycans or of the S100A8/A9 complex with carboxylated N-glycans exclusively expressed by endothelial cells after inflammatory activation. Another receptor that binds different S 100 proteins is the receptor for advanced glycation end products (RAGE). Direct binding to RAGE has so far been demonstrated for S100A12, S100B, S100A1, and S100P. The receptor for advanced glycation end products (RAGE) is a member of the immunoglobulin superfamily of cell surface molecules. RAGE consists of an extracellular domain, a single transmembrane spanning domain, and a highly charged cytosolic tail. RAGE signaling contributes to the activation of central cellular pathways which involve p38 or p44/42 MAP kinases, Cdc42/Rac, and NF-κB signaling components, thereby influencing features like cell survival, cell motility, and inflammatory response.

Binding of ligands to the RAGE receptor initiates cellular signals that activate NF-κB, which results in transcription of proinflammatory factors. The mammalian TOLL-like receptors (TLR) are receptors that recognize molecular patterns of pathogens. After the engagement of a pathogenic pattern ligand to TLR, recruitment of adaptor proteins, the transcription factor NF-κB is activated by the receptor-driven signaling cascade. It has been proposed that RAGE and TLR's use similar mechanisms which results in inflammatory reactions.

SUMMARY OF THE INVENTION

The inventors have characterized novel binding interactions of S100A9, i.e. a binding interaction with RAGE and a binding interaction with TLR4. They have also characterized the inhibition of these interactions by a compound which is effective in therapy, and thus developed screening methods to allow identification of compounds for therapy. The inventors have further shown that it is preferable for screening methods using S100A9 to be carried out in the presence of calcium and zinc ions.

Accordingly, the invention provides a method of identifying a compound for use in therapy which modulates the interaction of S100A9 with a ligand comprising:
(i) determining whether a candidate compound is capable of modulating the interaction of S100A9 with RAGE or the interaction of S100A9 with a TLR (Toll like receptor), or
(ii) determining whether a candidate compound is capable of binding to S100A9 in a manner which disrupts binding of S100A9 with RAGE or the binding of S100A9 with a TLR,
to thereby identify whether the compound may be used in therapy, wherein optionally the method is carried out in the presence of calcium and zinc ions.

The invention also provides an antibody that inhibits the interactions that have been characterized.

DESCRIPTION OF THE DRAWINGS

FIG. 6 shows displacement of S100A9 binding to RAGE by soluble heparan sulfate and heparin. Sensorgrams for binding of 200 nM S100A9 to immobilized RAGE in the absence or presence of 7.81-1000 ng/mL heparan sulfate or 3.91-500 ng/mL heparin are shown in (A) and (B). Inhibition curves and log-logit plots are shown in (C) and (D) for heparan sulfate (♦) and heparin (■), respectively. $IC_{50}$ values for heparan sulfate and heparin were calculated to 25.7 and 40.4 ng/mL calculated after linear regression (equations are inserted). The value for heparin corresponds to ~$8 \times 10^{-9}$M using the average molecular weight reported (4,000-6,000 Da). The molecular weight for heparan sulfate is not known. The binding of heparan sulfate and heparin to the RAGE surface is negligible (data not shown).

FIG. 15 shows displacement of S100A9 binding to human TLR4/MD-2 by compound A.

FIG. 16 shows binding of S100A9, S100A8 and the complex S100A8/A9 to immobilized anti-S100A9 mAb 43/8 demonstrated by Biacore™ binding assay. Panel A shows sensorgrams from top to bottom representing human S100A9, complex S100A8/A9 and S100A8. Panel B shows sensorgrams from top to bottom representing murine S100A9, complex S100A8/A9 and S100A8. The S100 proteins were injected at 100 nM concentration (based on the homo- or hetero-dimeric molecular weight) for 3 min at a flow rate of 30 µl/min in sample buffer (HBS-P buffer containing 1 mM $Ca^{2+}$ and 20 µM $Zn^{2+}$) (1; association phase) followed by injection of running buffer (same as sample buffer) at (2; dissociation phase). Panel C shows that binding of human S100A9 to immobilized anti-S100A9 mAb 43/8 is dependent on $Zn^{2+}$ and $Ca^{2+}$. Sensorgrams from top to bottom represent injection of 400, 200 and 100 nM S100A9 for 2 min at 30 µl/min in the presence or absence of 1 mM $Ca^{2+}$ and 20 µM $Zn^{2+}$ in HBS-P and after injection of sample buffer without S100A9 (NSB). Responses at late association phase were plotted versus concentration of S100A9. Data was fit to a one-site hyperbola model in GraphPad Prism yielding a more than 10-fold higher maximum response in the presence of calcium and zinc (4.9 and 0.46× $10^3$ RU, respectively).

FIG. 17 shows that anti-S100A9 mAb 43/8 binds specifically human S100A9 among the S100 proteins.

FIG. 18 shows that S100A9-antibody mAb 43/8 blocks binding of hS100A9 to RAGE, hS100A9 to TLR4/MD-2, and hS100A9 to Compound A. Responses at late association phase, obtained after injection of 100 nM S100A9, pre-incubated for at least 1 h at room temperature ±12.5-500 nM anti-S100A9 mAb 43/8, over immobilized RAGE (A), TLR4/MD-2 (B) or Compound A (C), were plotted versus concentration of anti-S100A9 mAb 43/8. Binding data were transformed to a log-logit plot for calculation of $IC_{50}$ value. Fifty % inhibition of S100A9 binding was obtained at an antibody concentration of 3.4, 2.7 and $12 \times 10^{-8}$ M for RAGE (♦; $r^2$ 0.98), TLR4/MD-2 (■; $r^2$ 0.91) and Compound A (▲; $r^2$ 0.96), respectively.

FIG. 19 shows that anti-S100A9 mAb 43/8 recognizes an epitope different to that of the 1C10 anti-human S100A9 antibody. At least a ten-fold difference in inhibition of the anti-S100A9 antibody to the 1C 10 anti-S100A9 antibody was demonstrated. The assay was performed by coating human anti-S100A9 mAb 43/8 on a CM5 chip at high density (3000 RU) using standard amine coupling chemistry. Human S100A9 (100 nM) was pre-incubated for at least one hour with the anti-S100A9 mAb 43/8 or 1C10 at concentrations of the antibody ranging from 0 to 400 nM. S100A9, with or without antibody, was injected for 3 min at a flow rate of 30 μl/min in sample buffer (HBS-P buffer containing 1 mM $Ca^{2+}$ and 20 μM $Zn^{2+}$) (1; association phase) followed by injection of sample buffer (2; dissociation phase).

FIG. 20 shows FACS analysis of Peripheral Blood Mononuclear Cells, PBMCs, stained with the anti-S100A9 mAb 43/8, the 27E10 anti-S100A8/A9 antibody, or an isotype control antibody. Human Peripheral Blood Mononuclear Cells (PBMCs) were incubated with the anti-S100A9 mAb 43/8 antibody, the anti S100A8/A9 antibody 27E10 or an isotype control antibody for 30 min at 4° C. Cell-associated fluorescence signals were measured by using a FACScan flow cytofluorometer. The anti-S100A9 mAb 43/8 could be seen to interact with the surface of human monocytes but with lower efficiency than the 27E10 anti-body. The isotype control antibody did not give any staining over back-ground.

FIG. 21 show TNFα production in peripheral Blood Mononuclear Cells after stimulation with beads coated with the anti-S100A9 mAb 43/8. Freshly prepared monocytes from human peripheral blood was incubated with 10 μg/ml anti-S100A9 mAb 43/8 for 24 hours. As a control, cells were incubated with medium alone (negative control), 10 μg/ml of an isotype matched antibody (negative control) or 0.5 μg/ml lipopolysaccharide (LPS) as a positive control.

FIG. 22 show NFκB reporter gene activity in human prostate cell line LNCaP cells after stimulation with the anti-S100A9 mAb 43/8. The anti-S100A9 mAb 43/8 induced expression of an NFκB reporter gene transfected (pLR446) into the LNCaP cells. Triplicate cell cultures with $10 \times 10^4$ cells (96 well plate) were incubated for 4h at 37° C. in 100 μl RPMI culture medium supplemented with 10% FCS and 10 μM $Zn^{2+}$, before the luminescence was measured (Steadylite HTS; Perkin Elmer). PMA (1.5 ng/ml) was used as a positive control and as a negative isotype control mouse IgG1 was used.

DESCRIPTION OF THE SEQUENCES MENTIONED HEREIN

Figure 1A:
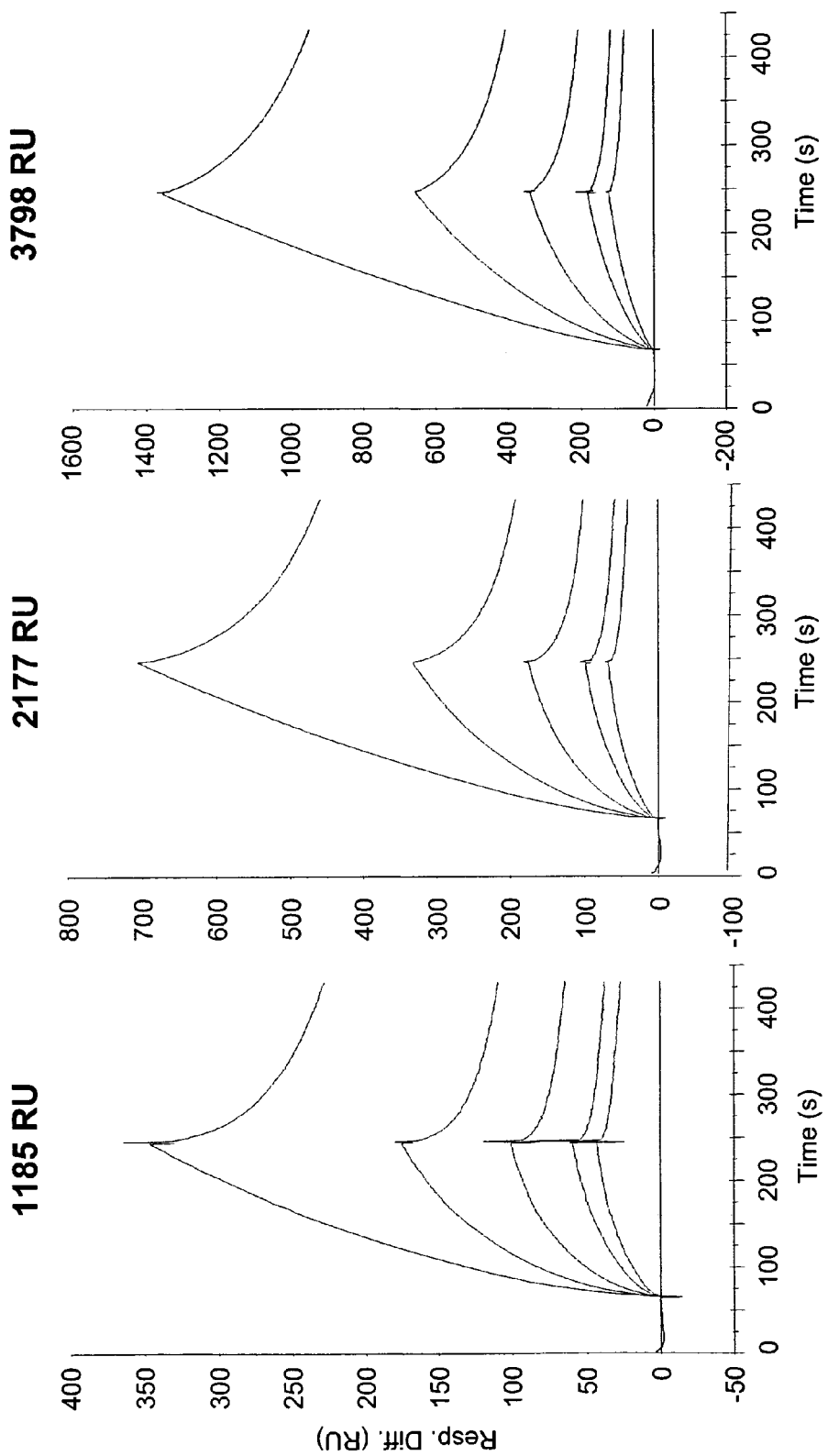
FIG. 1 shows binding of 25-400 nM S100A9 to RAGE immobilized by random amine coupling at three densities (approx. 1200, 2200 and 3800 RU in flow cell 2, 3 and 4 respectively). In (A), sensorgrams from bottom to top represent 25, 50, 100, 200 and 400 nM S100A9 after subtraction of the signal in the reference flow cell. Injection time was 3 min at a flow rate of 30 µL/min and regeneration was performed with a 15 µl pulse of 10 mM glycine-HCl, pH 2.0, for 30 s. In (B), responses at late association phase are plotted vs. concentration of S100A9. HBS-P containing 1 mM $CaCl_2$ and 10 µM $ZnCl_2$ (Robinson et al. (2002) J. Biol. Chem. 1277, 3658-65) was used as running and sample buffer.

SEQ ID NO: 1 shows the sequence of S100A9, SEQ ID NO: 2 shows the sequence of RAGE and SEQ ID NO's 3 to 15 show the sequences of TLR's 1 to 13. SEQ ID NO: 16 shows the rhTLR4 sequence. SEQ ID NO: 17 shows the rhMD-2 sequence. SEQ ID NO's 18 to 21 show the amino acid and DNA sequences for the variable portions of the 43/8 antibody.

DETAILED DESCRIPTION OF THE INVENTION

The invention relates to a method for identifying compounds for use in therapy, in particular compound for use in cancer therapy or immunotherapy. The compounds may be for use in therapy of autoimmune disease or an inflammatory condition. Typically the compounds may be used to treat an individual that has, or is at risk of having, a condition that can be prevented or treated by modulation of the immune system. The condition may be an autoimmune disease, such as type I diabetes, systemic lupus erythematosus, rheumatoid arthritis or multiple sclerosis. In one embodiment the condition is cancer. The individual to be treated in the therapy is typically a mammal, and preferably a human. Further the inventors have carried out the binding assays in conditions under which only S100A9 binds ligand strongly, and other S100 proteins do not, and thus preferred methods of the invention are based on binding assays carried out under such conditions.

The method of the invention identifies therapeutic compounds based on their ability to modulate the interaction between S100A9 and a ligand of S100A9, or on their ability to bind S100A9 in a manner which would disrupt binding of S100A9 with a ligand. The ligand is typically RAGE or a TLR (Toll like receptor). The TLR is preferably TLR4, but may be any TLR which binds S100A9, such as TLR1, TLR2, TLR3, TLR5, TLR6, TLR7, TLR8, TLR9, TLR10, TLR11, TLR12 or TLR13.

The method may be based on any suitable assay. The assay may measure or detect any of the physical properties mentioned herein, and a compound may be selected based on any such physical property. As can be seen in the Examples the inventors have characterized the properties of a therapeutically effective compound (termed compound A in the Examples), and thus the assay may determine whether a candidate compound has a relevant physical property which is the same or similar to the compound A.

Typically the method comprises determining whether a candidate compound is able to affect the binding of S100A9 and a ligand. The candidate compound may bind to S100A9 and cause a change in the conformation of S100A9, for example by inhibiting the binding of calcium or zinc to S100A9. Thus the assay may comprise providing a candidate compound to S100A9 and the ligand and determining whether the binding of S100A9 to the ligand has been affected. The assay may comprise allowing the candidate compound to bind S100A9 and then determining whether the binding would affect the binding of S100A9 to RAGE or a TLR, for example by testing whether the candidate compound binds S100A9 at the same site as RAGE or a TLR.

In a preferred embodiment the method comprises identifying a compound that modulates the interaction of S100A9 and a ligand. The term "modulate" as used herein refers to both upregulating (i.e. activation or stimulation, e.g. by agonizing or potentiating) and downregulation (i.e. inhibition or suppression, e.g. by antagonizing, decreasing or inhibiting) of an activity. The compound may be used to modulate the immune response in vivo.

In the method S100A9 and/or the ligand and/or the compound are preferably used in isolated form or substantially isolated form. Typically they are not present in or on the surface of cells and/or other proteins are not present. Typically less than 10, such as less than 5 or less than 3 other types of protein are present. Preferably calcium and zinc ions are present. In one embodiment 0.1 to 5 mM calcium ions, such as 0.5 to 2 mM calcium ions or about 1mM calcium ions and/or 1 to 100 uM zinc ions, such as 5 to 50 uM zinc ions or about 10 uM zinc ions are present.

In the method S100A9 or the ligand may be immobilized to a solid surface, and preferably the ligand is immobilized. Immobilisation may be achieved by any suitable means, for example by amine coupling. The solid surface may be one which is arranged so that changes in its surface characteristics are detected by surface plasma resonance. The immobilized molecule should still be capable of binding to S100A9 (where a ligand is immobilized) or the ligand (where S100A9 is immobilized).

In the method the binding of S100A9 and ligand is typically measured over a certain time period, for example over 10 to 12000 or 20 to 6000 or 60 to 500 seconds, which may allow the kinetics of the binding to be observed, and thus allow compounds to be selected based on the kinetics of binding. In addition the method may comprise measurement of the effects of different amounts/concentrations of the compound, thus allowing selection of compounds which have a dose-dependent effect.

The method of the invention preferably measures and/or selects a compound based on one or more of the following characteristics:
whether there is a 1:1 binding between the compound and S100A9 or ligand, for example by analysis of the effect of different concentrations of the compound,
the IC50 of the compound, and preferably whether the IC50 is from 1 nM to 200 uM, for example from 10 nM to 150 um, 0.5 uM to 100 uM or 20 to 70 uM,
the effect of the compound on the on-rate and/or off-rate of S100A9 and ligand, or
the level of decrease of binding of S100A9 and ligand,
whether the compound binds to S100A9 or ligand under physiological (in vivo) conditions,
whether the binding is specific,
whether the binding is reversible or irreversible, or
whether the compound causes a change in the structure of S100A9 or ligand.

In one embodiment at least 100, such as at least 1000, or at least 10,000 candidate compounds are tested. At least 1, 10, 50, 100 or more or all of the compounds that are tested preferably have one or more of the following characteristics:
they are not proteins or nucleic acids,
they are not lipids,
they are not toxic to mammals or humans,
they are soluble in water,
their structure is characterized or uncharacterized,
they are from a library of compounds which may, for example, have been synthesized together,
they are small organic molecules (typically containing carbon, hydrogen and generally also oxygen), and preferably having a relative molecular weight of at least 100, and less than 1000, such as a relative molecular weight of less than 600.

In a preferred embodiment the candidate compounds comprise a suitable structural element such as a 1,3-diketo functional group or a carboxylic acid functional group.

In one embodiment of the method less than 5%, for example less than 10% or less than 15% of the compounds which are tested are selected.

Forms/Variants of S100A9 or Ligand that may be used in the Method

Any suitable form of S100A9 or ligand may be used in the method. Thus they may used in the form of homologues and/or fragments of naturally occurring forms. The term "homologues and/or fragments" includes fragments of homologues of the relevant molecule. Homologues and/or fragments of any of the specific sequences disclosed herein may be used or of any naturally occurring isoform (for example of any mammalian species). Preferably a homologue and/or fragment of a human S100A9 or ligand is used. The homologue and/or fragment are termed "variant" in the discussion below.

The variant may be capable of complementing one or more activities of the naturally occurring molecule. Preferably the variant is capable of binding to S100A9 (if it is a variant of the ligand) or to the ligand (if it is a variant of S100A9). The variant polypeptide may comprise sequence which is homologous to all or part of S100A9 or the ligand. Thus the variant may be a fusion protein. The variant thus generally comprises at least the binding site of S100A9 or the ligand.

In a preferred embodiment the variant comprises the extracellular domain of the ligand. In the case where the variant is a variant of RAGE preferably at least 1, 2 or 3 of the immunoglobulin domains (or homologues of the domains) of RAGE are present in the variant. A preferred RAGE variant is described in the Examples and comprises amino acids 1 to 344 of human RAGE fused to the Fc region of human IgG1. In the case where the variant is a variant of S100A9 preferably at least the N-terminus helix 4 and linker region (or homologues of helix 4 and/or the linker region) are present in the variant and/or preferably at least the two histidine amino acids of helix 4 are present in the variant (which are important in binding zinc) and/or preferably the five histidines in the C terminus which are important in zinc coordination/binding are present in the variant and/or preferably the variant is capable of binding zinc.

In one embodiment the form of S100A9 or ligand which is used binds an antibody that binds the naturally occurring form. In the case of RAGE the form which is used may bind to MAB 11451 that is available from R & D Systems.

The variant is typically at least 100 amino acids long, such as at least 200 amino acids long, up to, for example, 2000 amino acid in length.

The forms of S100A9 and/or ligand may be modified, e.g. post-translationally modified. For example, they may be glycosylated or comprise modified amino acid residues. The ligand is preferably glycosylated, for example in a glycosylated form which is obtainable by expression in a mammalian (preferably human) cell.

In general use of other S100 naturally occurring proteins apart from S100A9 is not included in the method of the invention.

Any suitable monomer/dimer/multimer form of S100A9 or ligand may be used. S100A9 may be used in monomer, dimer or multimer form. It is preferably used in dimer form (i.e. comprising two S100A9 proteins). The ligand may be used in monomer or dimer form. RAGE is preferably used in dimer form (comprising two RAGE proteins).

Expressed S100A9 proteins or ligands (including fragments and homologues) can be recovered and purified from recombinant cell cultures by methods including ammonium sulfate or ethanol precipitation, acid extraction, anion or cation exchange chromatography, size-exclusion chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

Any polypeptides mentioned herein may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be post-translationally modified and in particular they may be glycosylated or may be non-glycosylated.

Homologues

Homologues of sequences are referred to herein. Such homologues typically have at least 20% homology, preferably at least 30%, 40%, 50%, 60%, 70%, 80%, 90%, 95%, 97% or at least 99% homology, for example over a region of at least 15, 20, 30, 100 more contiguous amino acids or over the length of the entire molecule. In a preferred embodiment at least 30% homology is present over the entire length of the molecule and/or at least 50% homology is present over at least 30 amino acids. The homology may be calculated on the basis of amino acid identity (sometimes referred to as "hard homology").

For example the UWGCG Package provides the BESTFIT program which can be used to calculate homology (for example used on its default settings) (Devereux et al (1984) *Nucleic Acids Research* 12, p387-395). The PILEUP and BLAST algorithms can be used to calculate homology or line up sequences (such as identifying equivalent or corresponding sequences (typically on their default settings), for example as described in Altschul S. F. (1993) J Mol Evol 36:290-300; Altschul, S, F et al (1990) J Mol Biol 215:403-10.

Software for performing BLAST analyses is publicly available through the National Center for Biotechnology Information. This algorithm involves first identifying high scoring sequence pair (HSPs) by identifying short words of length W in the query sequence that either match or satisfy some positive-valued threshold score T when aligned with a word of the same length in a database sequence. T is referred to as the neighborhood word score threshold (Altschul et al, supra). These initial neighborhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) Proc. Natl. Acad. Sci. USA 89: 10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) *Proc. Natl. Acad. Sci. USA* 90: 5873-5787. One measure of similarity provided by the BLAST algorithm is the smallest sum probability (P(N)), which provides an indication of the probability by which a match between two amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

The homologous sequence typically differs by less than 5, 10, 20 or 50 mutations (which may be substitutions, deletions or insertions of nucleotide or amino acids). These mutation may be measured across any of the regions mentioned above in relation to calculating homology. The substitutions are preferably conservative substitutions. These are defined according to the following Table. Amino acids in the same block in the second column and preferably in the same line in the third column may be substituted for each other:

| ALIPHATIC | Non-polar | G A P |
|---|---|---|
| | | I L V |
| | Polar - uncharged | C S T M |
| | | N Q |
| | Polar - charged | D E |
| | | K R |
| AROMATIC | | H F W Y |

Further Testing of the Identified Compound

A compound identified by the above method (which is non-cellular and not in vivo) may be further tested to determine whether it modulates the immune response, and preferably whether it decreases the immune response. Compounds may be selected if they are found to modulate the immune response. Any suitable cell based assay or animal model assay may be used. Preferably the assay will comprise monocytes which express S100A9, and will test whether the compound is able to modulate the growth or activity of such monocytes. The assay may determine whether the compound modulates S100A9 expression on the monocytes. The assay may determine whether the compound binds to a CD11b+CD14+ population of cells and/or whether the compound modulates (for example decreases) the level or activity of such cells.

Thus the compound may be contacted with a monocyte (such as a CD11b+CD14+ monocyte) to determine whether the compound modulates the growth or activity of the monocyte.

The assay may be in the form of a mixed lymphocyte reaction (MLR), for example one comprising monocytes which have been stimulated with TOLL.

The compound may be tested to determine whether it modulates (for example increases or decreases the numbers of) monocytes (for example dendritic cells) in an animal model and/or for therapeutic efficacy in an animal model. The animal model may be of any of the conditions mentioned herein, such as cancer, autoimmune disease or an inflammatory condition. The animal is preferably a rodent, such as a mouse or rat.

Thus the compound may be administered to an animal and a sample of containing monocytes may be taken from the animal to determine whether the compound causes a decrease in the number or activity of monocytes in the animal. In another embodiment the compound may be administered to an animal with a cancer or autoimmune disease, or an animal at risk of having cancer or an autoimmune disease, and whether or not the compound treats or prevents the autoimmune disease is determined.

The Antibody of the Invention

The Examples describe antibody 43/8 which is a specific modulator of S100A9 capable of inhibiting its interaction with TLR4 and RAGE. Antibody 43/8 was generated by immunizing S100A9 null mice with recombinant S100A9. The antibody recognizes a unique epitope on the S100A9 molecule. This epitope overlaps with the region of the molecule that can interact with TLR4 and RAGE. Furthermore, the interaction of 43/8 with S100A9 was dependent on the presence of $Ca^{2+}$ and $Zn^{2+}$ in the S100A9 protein. 43/8 antibody was capable of stimulating TNFα production in human monocytes. Furthermore, the antibody was able to induce expression of an NFκB reporter gene in a cell line expressing S100A9. Thus, an antibody with specificity to the same epitope as that of proinflammatory mediators (TLR4 and RAGE) is capable of binding membrane bound S100A9 and thereby transmitting a signal across the plasma membrane.

Samples of the hybridoma cell line 43/8 (designated "HYBRIDOMA S100A9 43/8"), which produces monoclonal antibody 43/8, were deposited under The Budapest Treaty of 1977 with the European Collection of Cell Cultures ("ECACC"), Porton Down, Salisbury, SP4 0JG, UK, on 13 Feb. 2013, and bear ECACC deposit reference number 13021301.

The invention accordingly provides an antibody that specifically binds to an epitope on S100A9, which includes any species of S100A9, such as human S100A9 (for example as defined by SEQ ID NO:1). The epitope is preferably one which is present in the region of S100A9 that binds to TLR4 and/or RAGE, so that for example one or more amino acids of the epitope bind to (or contact) TLR4 and/or RAGE during binding with these molecules. The epitope may be one which is not accessible to a labeling agent when S100A9 is bound to TLR4 and/or RAGE, for example an iodination agent (or at least one amino acid of the epitope is not accessible to a labeling agent when S100A9 is bound to TLR4 and/or RAGE).

The antibody may bind to an epitope which is bound by antibody 43/8 defined in the Examples. Antibody 43/8 is defined with reference to having variable chains shown by SEQ ID NO's 18 and 20. In one embodiment the antibody of the invention comprises variable chains that have sequence:
  (a) as shown in SEQ ID NO:18 and/or shown in SEQ ID NO:20, or
  (b) which is homologous to sequence shown in SEQ ID NO:18 and/or shown in SEQ ID NO:20, or
  (c) which is a fragment of (a) or (b).

The antibody is preferably capable of inhibiting the binding of S100A9 to TLR4 and/or RAGE, and thus typically the presence of the antibody will reduce the level of binding between S100A9 and TLR4 and/or RAGE if these molecules are contacted with S100A9. Such an inhibition may be in accordance with the data described in Examples and Figures.

The antibody may bind human and/or murine S100A8, A100A9 and/or S100A8/S100A9 complexes. Typically binding of antibody to S100A9 is dependent on the presence of zinc and/or calcium ions.

A preferred antibody is capable of binding to monocytes, such as human and/or murine monocytes. The antibody may be capable of stimulating such cells, for example to produce TNFα. Thus the antibody may be able to induce a transmembrane signal in such cells, for example one which leads to a pro-inflammatory response.

The antibody of the invention recognizes an epitope which is not recognized by known antibodies. In order to generate such an antibodies S100A9 was used to immunize a S100A9 null mouse. In one embodiment the antibody is obtainable by immunization of a mammal which lacks S100A9. Preferably such a mammal is a rodent, such as a mouse.

In one embodiment the antibody of the invention is identifiable by the screening method of the invention, and thus may have any of the characteristics mentioned above which are used as the basis for identifying therapeutic compounds.

The antibody of the invention is therapeutically useful, and may be administered to patients (preferably human patients) to prevent or treat conditions that can be treated or ameliorated by modulation of the immune system. Suitable conditions include any of the general or specific conditions mentioned herein (i.e. which can prevented or treated by compounds identified in the screening method described herein).

The antibodies of the invention are also useful in purification, isolation or screening methods involving immunoprecipitation techniques.

As mentioned above the antibodies recognise specific epitopes. An antibody, "specifically binds" to an epitope when it binds with preferential or high affinity to the epitope for which it is specific but does substantially bind not bind or binds with only low affinity to other antibody. In one embodiment the antibody does not bind to a variant epitope sequence which has less than 50% homology to the epitope recognised by the epitope. In one embodiment the antibody only binds human S100A9, and does not bind any other S100 proteins and/or does not bind S100A9 of other species. In a preferred embodiment the antibody binds to the S100A8/S100A9 complexes, but has minimal affinity to other molecules.

A variety of protocols for competitive binding or immunoradiometric assays to determine the specific binding capability of an antibody are well known in the art (see for example Maddox et al, J. Exp. Med. 158, 1211-1226, 1993). Such immunoassays typically involve the formation of complexes between the specific protein and its antibody and the measurement of complex formation.

For the purposes of this invention, the term "antibody", unless specified to the contrary, includes fragments which bind to the relevant epitope. Such fragments include Fv, F(ab') and F(ab')$_2$ fragments, as well as single chain antibodies. Furthermore, the antibodies and fragment thereof may be chimeric antibodies, CDR-grafted antibodies or humanised antibodies. The antibodies may be of any species, but are preferably human or mice antibodies. The antibody may be polyclonal, but is preferably monoclonal. The antibody is preferably an IgG antibody, but may be an IgM or IgE antibody.

Antibodies of the invention can be produced by any suitable method. Means for preparing and characterising antibodies are well known in the art, see for example Harlow and Lane (1988) "Antibodies: A Laboratory Manual", Cold Spring Harbor Laboratory Press, Cold Spring Harbor, N.Y. For example, an antibody may be produced by raising antibody in a host animal against the whole polypeptide or a fragment thereof, for example an antigenic epitope thereof, herein after the "immunogen". The fragment may be any of the fragments mentioned herein (typically at least 10 or at least 15 amino acids long).

A method for producing a polyclonal antibody comprises immunising a suitable host animal, for example an experimental animal, with the immunogen and isolating immunoglobulins from the animal's serum. The animal may therefore be inoculated with the immunogen, blood subsequently removed from the animal and the IgG fraction purified.

A method for producing a monoclonal antibody comprises immortalising cells which produce the desired antibody. Hybridoma cells may be produced by fusing spleen cells from an inoculated experimental animal with tumour cells (Kohler and Milstein (1975) *Nature* 256, 495-497).

An immortalized cell producing the desired antibody may be selected by a conventional procedure. The hybridomas may be grown in culture or injected intraperitoneally for formation of ascites fluid or into the blood stream of an allogenic host or immunocompromised host. Human antibody may be prepared by in vitro immunisation of human lymphocytes, followed by transformation of the lymphocytes with Epstein-Barr virus.

For the production of both monoclonal and polyclonal antibodies, the experimental animal is suitably a goat, rabbit, rat, mouse, guinea pig, chicken, sheep or horse. As mentioned above, such an animal preferably does not express S100A9. If desired, the immunogen may be administered as a conjugate in which the immunogen is coupled, for example via a side chain of one of the amino acid residues, to a suitable carrier. The carrier molecule is typically a physiologically acceptable carrier. The antibody obtained may be isolated and, if desired, purified.

The antibody of the invention may be present in a substantially isolated form. It may be mixed with carriers or diluents which will not interfere with its intended use and still be regarded as substantially isolated. It may also be in a substantially purified form, in which case it will generally comprise at least 90%, e.g. at least 95%, 98% or 99%, of the protein or dry mass of the preparation.

Administration

Compounds identified by the method of the invention or the antibody of the invention may be formulated into pharmaceutical composition. The pharmaceutical composition may be used in clinical treatment of diseases resulting from autoimmunity such as multiple sclerosis, insulin-dependent diabetes mellitus, systemic lupus erythematosus, rheumatoid arthritis, inflammatory bowel disease and psoriasis and, furthermore, diseases where pathologic inflammation plays a major role, such as asthma, atherosclerosis, stroke and Alzheimer's disease. More particularly, it may be used for the treatment of, for example, multiple sclerosis and its manifestations. The pharmaceutical composition may be used in the treatment of cancer.

The formulation will depend upon factors such as the nature of the substance and the condition to be treated. Any such substance may be administered in a variety of dosage forms. It may be administered orally (e.g. as tablets, troches, lozenges, aqueous or oily suspensions, dispersible powders or granules), parenterally, subcutaneously, intravenously, intramuscularly, intrasternally, transdermally or by infusion techniques. The substance may also be administered as suppositories. A physician will be able to determine the required route of administration for each particular patient.

Typically the substance is formulated for use with a pharmaceutically acceptable carrier or diluent. The pharmaceutical carrier or diluent may be, for example, an isotonic solution. For example, solid oral forms may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Such pharmaceutical preparations may be manufactured in known manner, for example, by means of mixing, granulating, tabletting, sugar-coating, or film coating processes.

Liquid dispersions for oral administration may be syrups, emulsions and suspensions. The syrups may contain as carriers, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol. The suspensions or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

Solutions for intravenous or infusions may contain as carrier, for example, sterile water or preferably they may be in the form of sterile, aqueous, isotonic saline solutions.

A therapeutically effective non-toxic amount of substance is administered, typically to a patient (preferably a human patient) in need thereof. The dose may be determined according to various parameters, especially according to the substance used; the age, weight and condition of the patient to be treated; the route of administration; and the required regimen. Again, a physician will be able to determine the required route of administration and dosage for any particular patient. A typical daily dose is from about 0.001 to 50 mg per kg, preferably from about 0.1 mg/kg to 10 mg/kg of body weight, according to the activity of the specific inhibitor, the age, weight and conditions of the subject to be treated, the type and severity of the disease and the frequency and route of administration. Preferably, daily dosage levels are from 0.5 mg to 2 g.

The following Examples illustrate the invention:

EXAMPLES

Proteomic Screen

When investigating compounds that bind S100A9 or RAGE in a proteomics screen, no compounds were identified which bound RAGE, whilst compounds which bound S100A9 were identified. Thus in order to identify compounds that modulate the interaction of S100A9 with a ligand such as RAGE, it is more efficient to look for compounds that bind to S100A9.

Notably, a distinguishing feature of S100A9 is its extended C-terminus, rendering it considerably larger than other S100 family members. Furthermore, S100A9 contains two EF-hands motifs (helix-loop-helix motif) flanked by conserved hydrophobic residues and separated by a hinge region. S100A9 shares this theme with the S100 protein family. The sequences of the hinge region and the C-terminal helix, H4, are the most variable among the S100 proteins. Binding of the S100A9 protein, and the S100A9 and S100A8 complex, to endothelial cells, requires the presence of calcium and zinc ions.

The Biacore Assay

The Surface Plasmon Resonance (SPR) technology, such as the BIAcore assay system, was chosen as a first step of the screening method. The assay format provides affinity and kinetic information on the interaction of a ligand and an immobilized receptor. Moreover, is the assay format particular useful in mimicking physiological conditions without labeling any of the interactants. Especially, where avidity and multivalent presentations are involved, and the monomeric interaction is weak, is the chosen assay format useful. Compounds may then be tested for their ability to modulate the ligand—receptor interaction in an inhibition assay where the ligand is co-injected with varying concentrations of compound to determine whether the compound inhibits this interaction in a dose-dependent manner. Finally, compounds may be compared as to their inhibitory potency.

The Immobilization of RAGE to a Chip

The RAGE receptor was immobilized onto a biosensor surface using random amine coupling chemistry to a CM5 chip in a Biacore assay system. The applied form of RAGE, is a recombinant human RAGE receptor, where the extracellular domain of RAGE, amino acid 1-344, is fused to the Fc region of human IgG$_1$. The chimeric protein was expressed in the mouse myleoma cell line, NSO, as a disulfide-linked homo-dimeric protein with a calculated molecular mass of 61 kDa. Human RAGE possesses two conserved glycosylation sites and heterogeneity in glycosylation results in subpopulations of RAGE, differing in N-carboxylated glycans displaying different ligand binding properties, (Srikrishna G, et al., J Immunol 175, 5412-5422, 2005). Due to extensive glycosylation of RAGE relative to that of the Fc domain and a higher mass of the latter, it was also assumed that chimeric RAGE/Fc will be coupled predominantly via the Fc domain and result in a semi-oriented coupling to the sensor chip. Thus, the chosen assay format allows the extracellular part of RAGE to be exposed to ligand binding, and reconstituting a biological model where anchored membrane receptor interacts with soluble ligands.

The biological activity of immobilized RAGE was tested by injecting a specific anti-human RAGE monoclonal antibody recognizing the extracellular domain of human RAGE, over the surface of the immobilized RAGE. FIG. 2, shows sensograms for binding of 12.5-200 nM anti-RAGE over immobilized RAGE. An apparent dissociation constant, $K_D$, in the nanamolar range was obtained.

The Novel Interaction S100A9 and RAGE

Figures 2A, 2B:
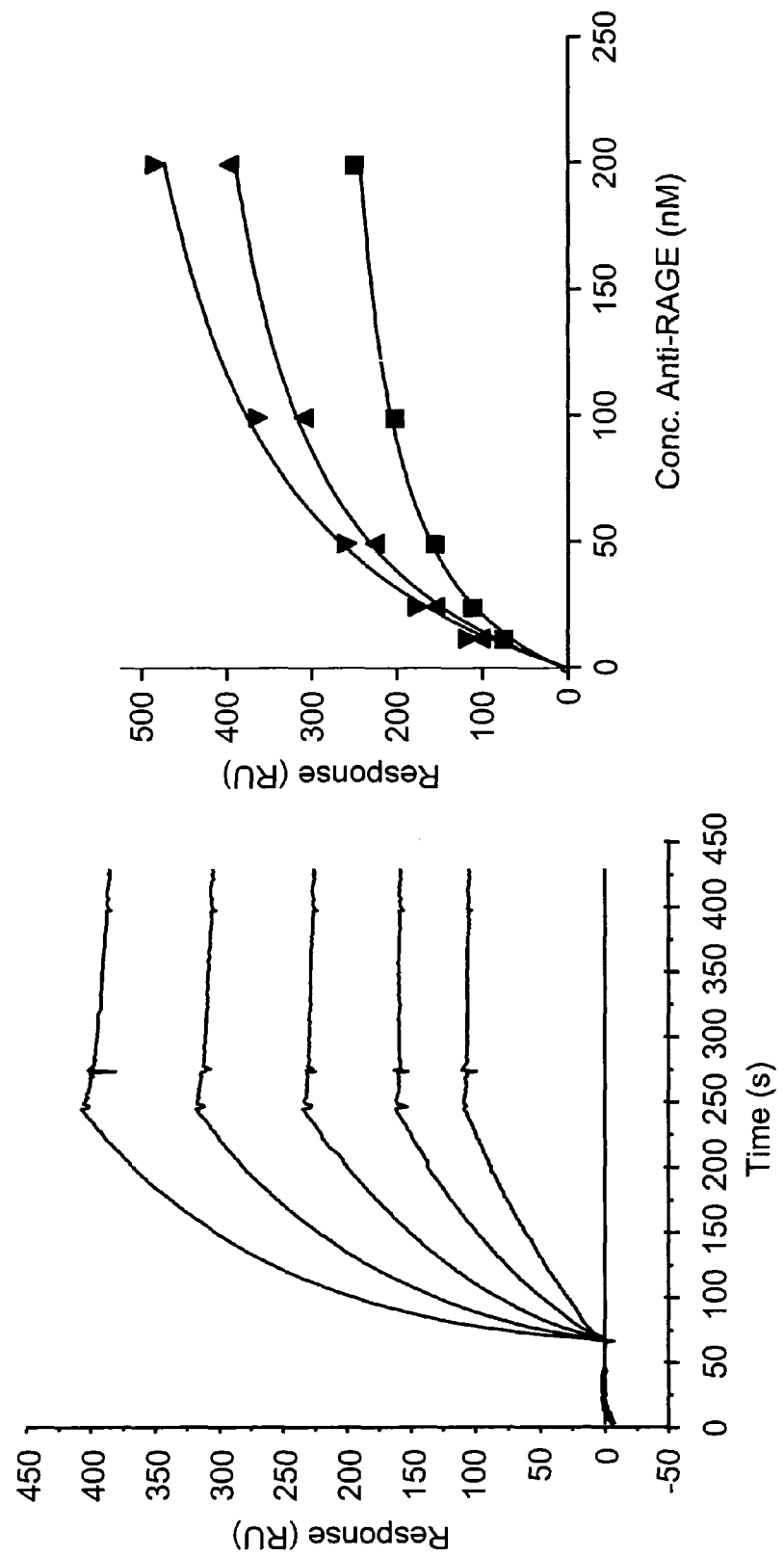
FIG. 2 shows a test of activity of immobilized RAGE by injection of a mouse monoclonal antibody recognizing the extra-cellular domain of human RAGE (MAB11451, R&D Systems). In (A), sensorgrams after injection of 12.5-200 nM anti-RAGE over immobilized RAGE (density 2177 RU) are shown and in (B) saturation curves for the three RAGE surfaces in FIG. 1 obtained after plotting antibody concentration vs response at late association phase (t~235 s). An apparent dissociation constant, $K_D$ of 4.3, 5.8 and $6.9 \times 10^{-8}$ M and maximum binding at 295, 502 and 635 RU were calculated for the respective RAGE surfaces after fit of data to a one-site hyperbola binding model ($R^2 > 0.99$).
Figure 3:
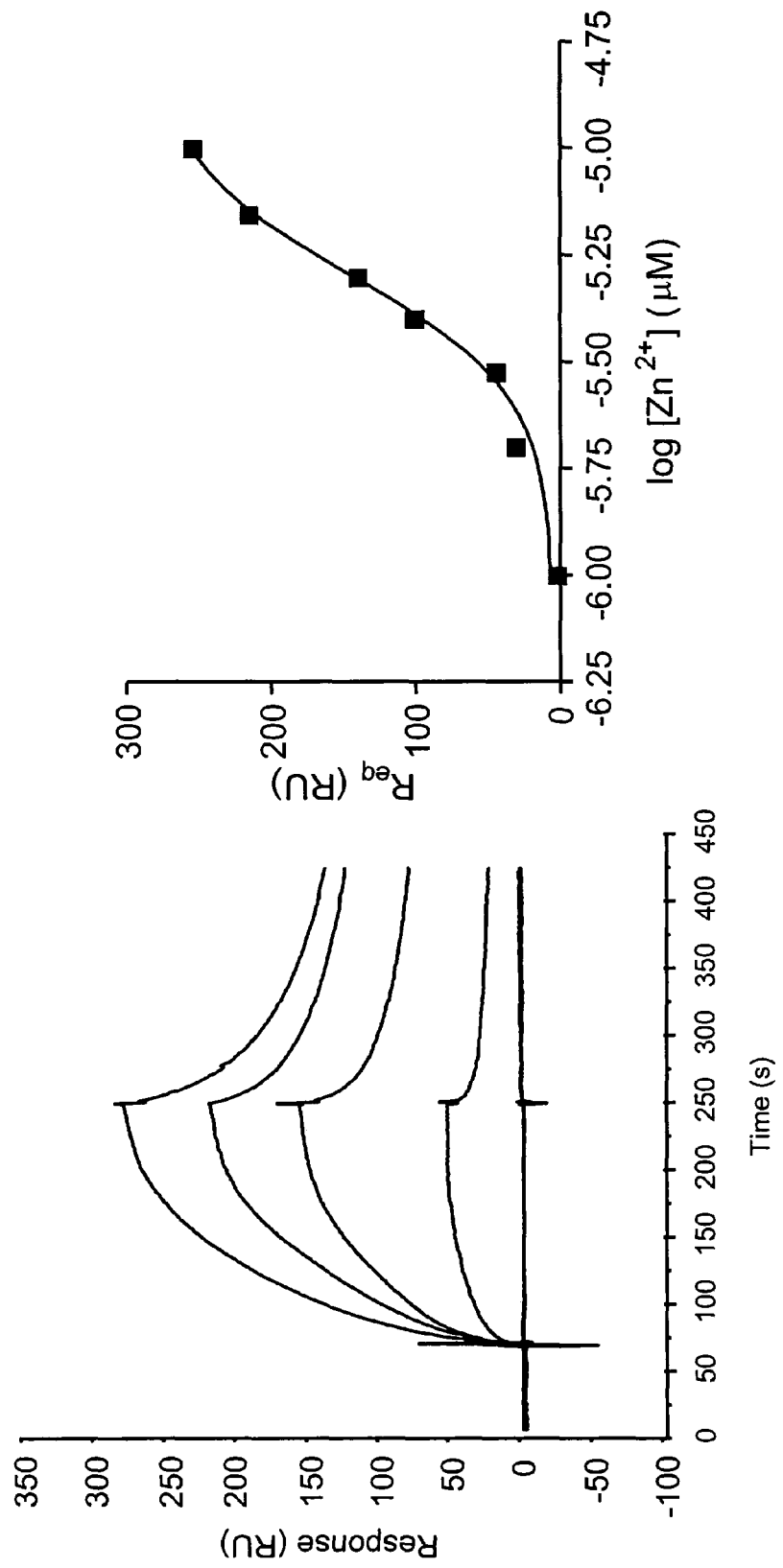
FIG. 3 shows titration of $Zn^{2+}$ for optimal binding of 100 nM S100A9 to RAGE. In the left panel, sensorgrams from bottom to top represent: 100 nM S100A9 in HBS-P buffer containing 250 µM $CaCl_2$ and 0 to 10 µM $ZnCl_2$. In the right panel, responses at late association phase, $R_{eq}$, obtained after fitting data to a 1:1 binding model, are plotted vs. the log concentration of $Zn^{2+}$. $EC_{50}$ was calculated to 5.0 µM $Zn^{2+}$ using a sigmoidal dose-response ($R^2$ 0.996) model with variable slope. Experimental conditions were as described in FIG. 1.
Figure 4:
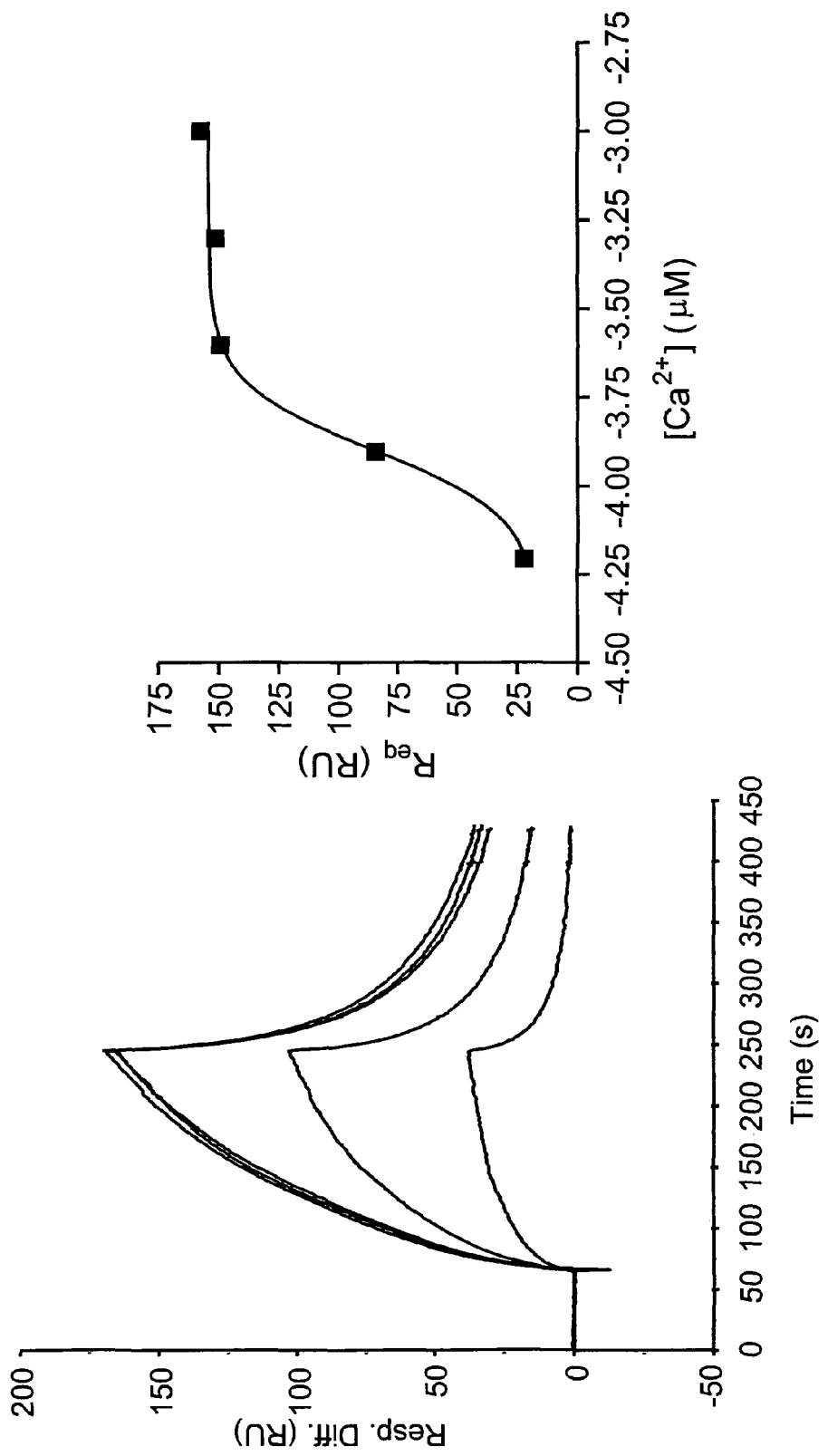
FIG. 4 shows titration of $Ca^{2+}$ for optimal binding of 100 nM S100A9 to RAGE. In the left panel, sensorgrams from bottom to top represent: 100 nM S100A9 in HBS-P buffer containing 10 µM $ZnCl_2$ and 62.5 to 1000 µM $CaCl_2$. In the right panel, responses at late association phase, $R_{eq}$, obtained after fitting data to a 1:1 binding model, are plotted vs. the log concentration of $Ca^{2+}$. $EC_{50}$ was calculated to 126 µM $Ca^{2+}$ using a sigmoidal dose-response ($R^2$ 0.999) model with variable slope. Experimental conditions were as described in FIG. 1.

Binding of S100A9 to RAGE was demonstrated after the immobilization of the rhRAGE-Fc by random amine coupling to a chip. In FIG. 2, sensorgrams from injection of 37.5-200 nM S100A9 over immobilized RAGE are shown. The responses are plotted versus concentration of S100A9, a sigmoidal dose-response curve is obtained although saturation is not reached within the concentration range used, FIG. 2B. The S100 proteins are calcium-binding proteins and some also require low concentrations of $Zn^{2+}$ to adapt a biologically active conformation. Titration of $Zn^{2+}$ for optimal binding of 100 nM S100A9 to RAGE was performed in presence of $Ca^{2+}$. The optimal zinc ion concentration was determined to 10 µM $Zn^{2+}$ in the presence of calcium, FIG. 3.

Figure 5:
FIG. 5 shows binding of 200 nM S100 proteins and annexin II (bovine $AnxII_2$: $S100A10_2$ tetrameric complex) to immobilized RAGE. Responses were obtained as $R_{eq}$ values after fit of data to a 1:1 binding model or as the signal at late association phase (t~235 s). Experimental conditions were as in FIG. 1. Signals were not corrected for mass contribution.

Under the experimental conditions used, S100A9 showed more than 10-fold higher binding to RAGE than the next group of RAGE binders (AnxII, S100A12, and S100A8/9), FIG. 5. In vivo, S100A9 usually forms hetero-dimeric complexes with S100A8.

Interestingly, the significantly lower binding of the S100A8/9 hetero-dimer to RAGE than for homo-dimeric S100A9 implicates that binding to RAGE occurs via S100A9 and that the binding site is partially blocked in the S100A8/9 hetero-dimer. The finding that weak or no binding was obtained with putative RAGE ligands like S100A1, S100A12, S100B and S100P indicates that S100A9, unique among the S100 members to interact strongly with glycosaminoglycans and carboxylated glycans, may interact with glycans on RAGE. The S100A9 protein binding to endothelial cells has been shown to involve glycosaminoglycans structures and may be blocked by heparin and heparin sulfate. Displacement of S100A9 binding to RAGE by soluble heparin or heparan sulfate was demonstrated for the immobilized RAGE to a chip, FIG. 6. The finding demonstrates the biological relevance of the disclosed interaction between S100A9 and RAGE.

The Compounds are Modulators of the S100A9 to RAGE Interaction

Figure 7:
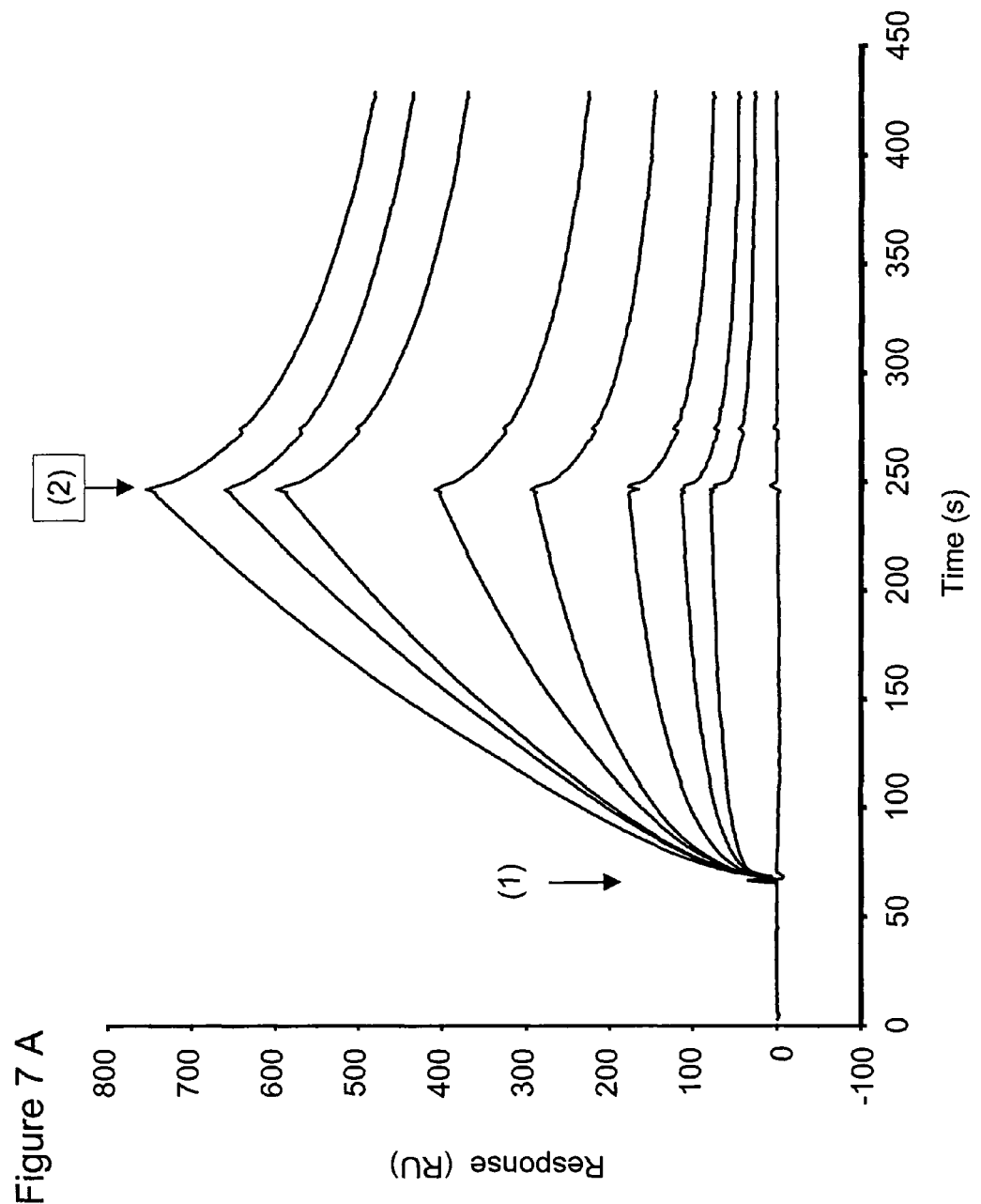
FIG. 7 shows displacement of S100A9 binding to immobilized RAGE by soluble compound A. In (A), sensorgrams after injection of S100A9, 200 nM, in the absence or presence of compound A as competitor. Sensorgrams from top to bottom represent: S100A9 without and with 15.625, 31.25, 62.5, 125, 250, 500 and 1000 µM compound A as competitor and from sample buffer without S100A9 and competitor. In (B), binding data is plotted as an inhibition curve (♦) and the response for S100A9 in the absence of competitor (dotted line). In (C), binding data is plotted after log-logit transformation. $IC_{50}$ values for compound A was calculated to 63 µM ($r^2$ 0.991). Arrows in (A) indicate start of the association phase (1), i.e. injection of S100A9±competitor, and dissociation phase (2), where running buffer is pumped over the surface. Injection time, flow rate and regeneration conditions were as in FIG. 1.

The binding of S100A9 to immobilized RAGE is modulated by compound A, FIG. 7. Dose-dependent inhibition is obtained with an IC$_{50}$ value of 63 µM for the compound A. Compound A is the first compound that has been identified that binds S100A9 (known compounds bind to the S100A9/S100A8 complex).

The TLR4 Immobilized on Chip

Figure 14:
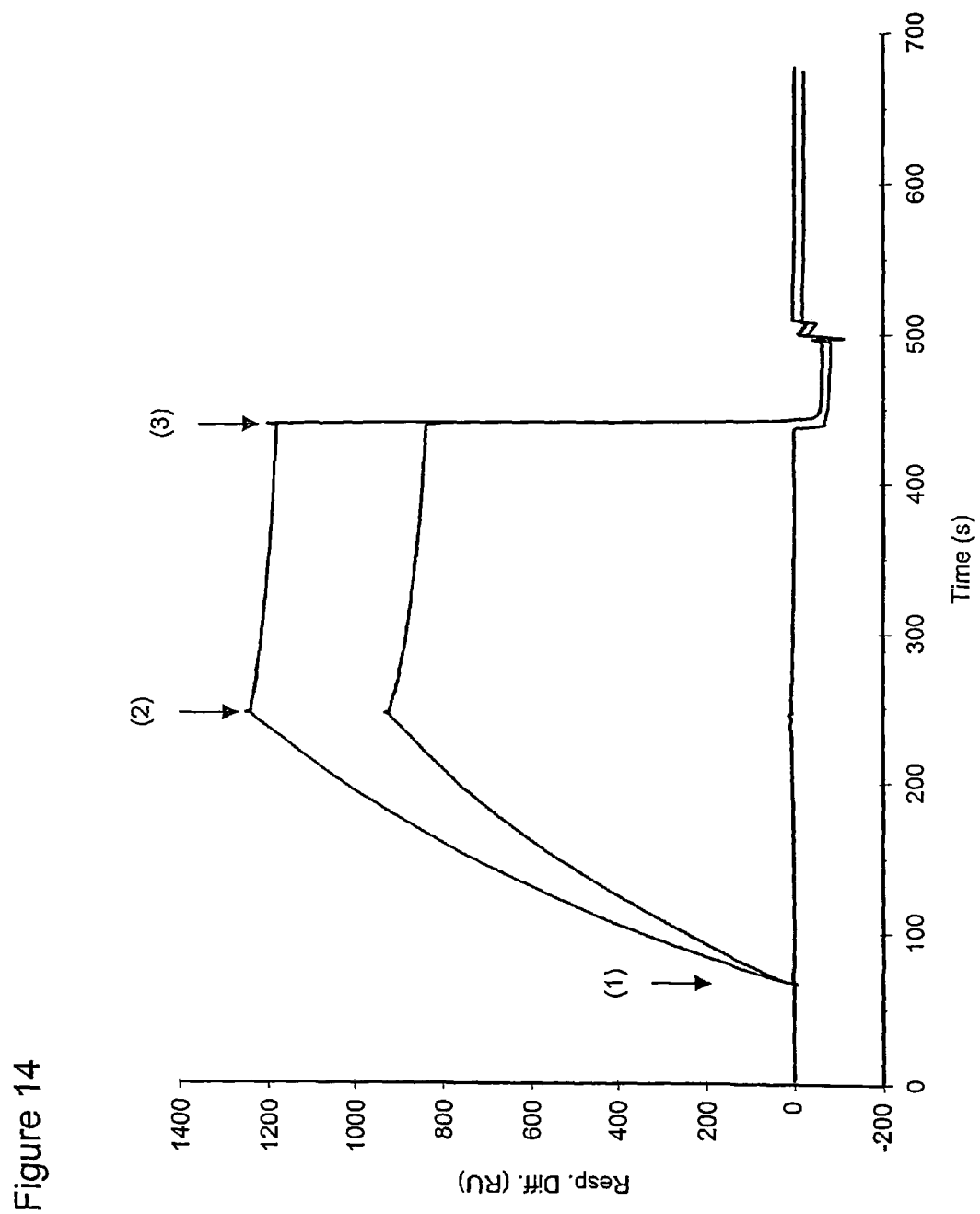
FIG. 14 shows binding of S100A9 to human TLR4/MD-2.

The TOLL-like receptor 4 was immobilized on the sensor chip. Binding to S100A9 was detected. FIG. 14 shows binding of S100A9 to amine-coupled human TLR4/MD-2. Sensorgrams from bottom to top represent injection of sample buffer in the absence of S100A9, 100 and 200 nM S100A9 after subtraction of the signal in the reference flow cell. Injection time was 3 min at a flow rate of 30 µL/min and regeneration was performed with a 30 µl pulse of 3 mM EDTA in HBS-P buffer (HBS-EP) for 60 s. Arrows indicate injection of sample (1; association phase), running buffer (2; dissociation phase) and regeneration solution (3). HBS-P containing 1 mM CaCl$_2$ and 10 µM ZnCl$_2$ (Robinson et al. 2002) was used as running and sample buffer. An apparent dissociation constant of $8.6 \times 10^{-8}$ M, on- and off-rates of $3.9 \times 10^4$ 1/Ms and $3.5 \times 10^{-4}$ 1/s, and maximal binding at $1.8 \times 10^3$ RU were calculated after fitting data to a 1:1 Langmuir binding model (Chi2 6.8).

Figure 1B:
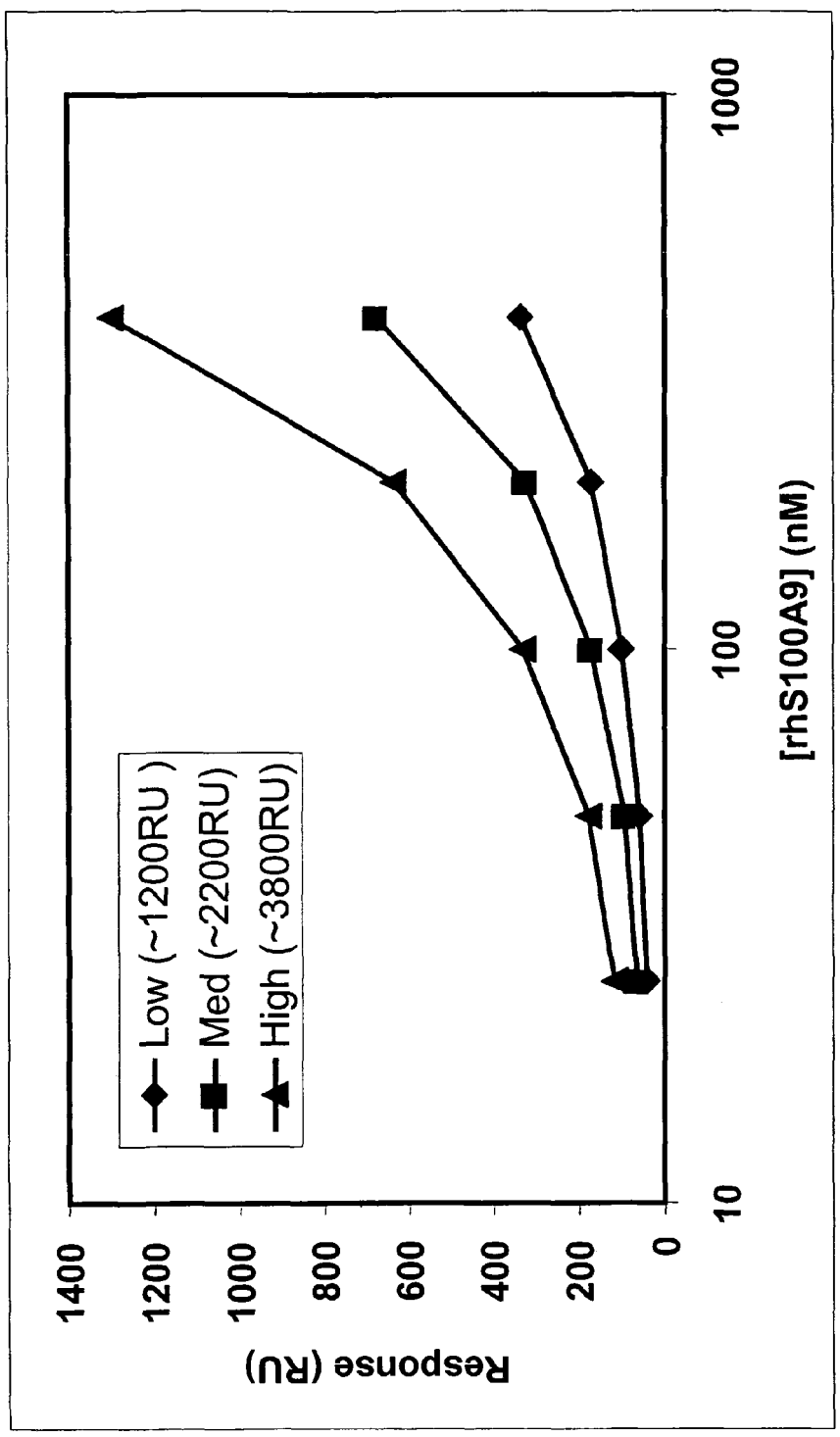

FIG. 15 shows displacement of S100A9 binding to immobilized human TLR4/MD-2 complex by soluble compound A. In (A), sensograms after injection of S100A9, 100 nM, in the absence or presence of compound A as competitor are shown. Sensograms from top to bottom represent: S100A9 without and with 7.8125, 15.625, 31.25, 62.5, 125, 250, 500 and 1000 µM compound A as competitor. In (B), binding data is plotted as an inhibition curve. IC$_{50}$ value for compound A was calculated to ~53 µM ($r^2$ 0.989). Arrows in (A) indicate start of the association phase (1), i.e. injection of S100A9±competitor, and dissociation phase (2), where running buffer is pumped over the surface. Injection time, flow rate and regeneration conditions were as in FIG. 1. HBS-P containing 1 mM CaCl$_2$ and 10 µM ZnCl$_2$ (Robinson et al. 2002) was used as running and sample buffer.

In vitro Assay—MLR

S100A9 Surface Expression of Human Monocytes

Figure 8:
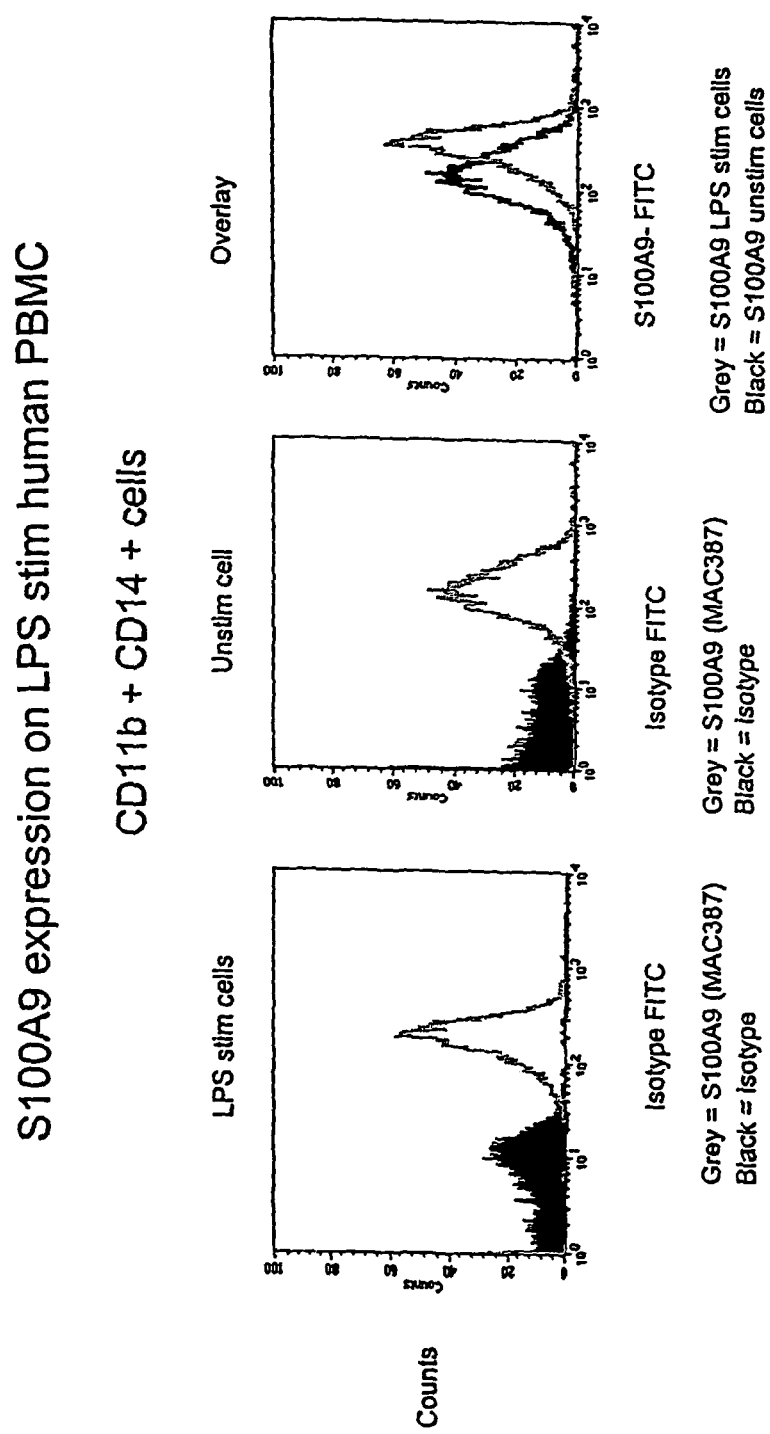
FIG. 8 concerns S100A9 expression on LPS stimulated human PBMC. Human monocytes express S100A9 on the cell surface and the expression is increased by TLR4 (LPS) stimulation. The cells were gated for $CD11b^+CD14^+$ cells. S100A9-specific staining of cells incubated either in medium alone (dark/blue) or together with LPS (lighter colour/green) are displayed.

The S100A9 molecule is present on the cell surface of only a minority of human PBMC. This can be illustrated by staining total human PBMC with a flourescien-labelled antibody specific for S100A9 followed by analysis in a FACS analyser. As shown in FIG. 8, only a small population of the cells bound the antibody while the majority of the cells had a flourescence equal to that seen after incubation with an isotype matched antibody with unknown specificity as a negative control. Furthermore, when the cells had been pre-incubated with a TLR4 ligand (LPS) for 24 hours the fraction of PBMCs that expressed S100A9 remained more or less constant while the staining intensity of the population was increased, indicating that each S100A9-binding cell expressed more molecules on the cell surface.

Figure 9:
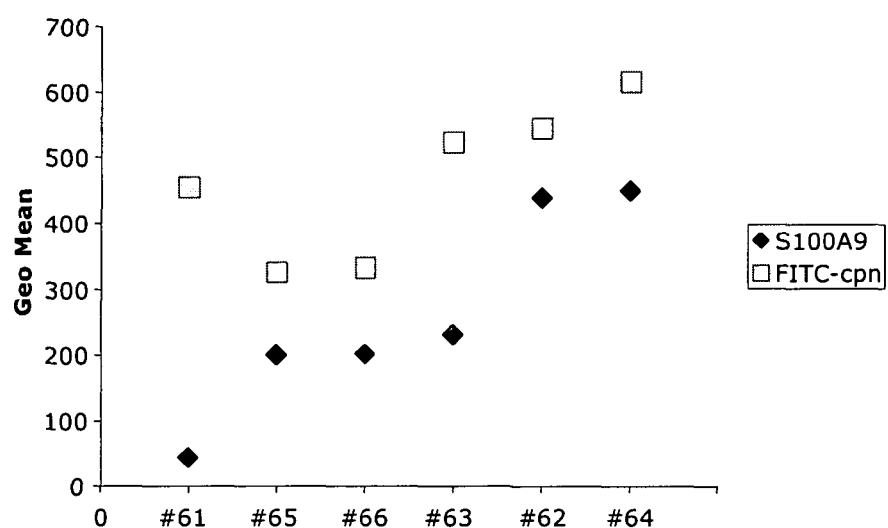
FIG. 9 shows that S100A9 expression is correlated to compound A binding on human blood monocytes. Correlation between S100A9 surface staining and binding of a fluorescent S100A9-binding compound to human blood monocytes PBL from 6 healthy volunteers were stained with fluorescence labelled S100-binding compound (diamonds) and fluorescent anti-S100A9 antibody (squares) and analysed by FACS after gating on the monocyte population.

Monocytes have been described as one of the S100A9 expressing cell types in human blood (Zwadlo et al. (1988) Clin. Exp. Immunol. 72, 510). Indeed, essentially all monocytes can be shown to express S100A9 on the cell surface by FACS analysis (FIG. 9) and also on this cell population the level of surface expression is increased after stimulation with a TLR ligand.

Figure 10:
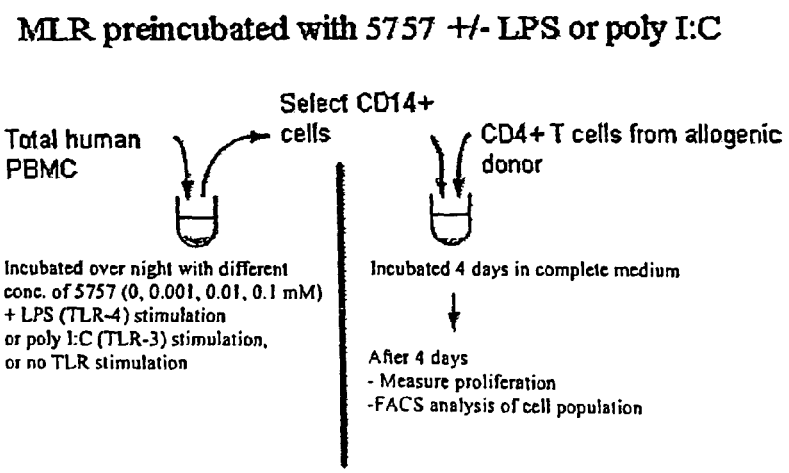
FIG. 10 concerns a MLR preincubated with compound A. The cartoon shows an in vitro activity assay for a S100A9-binding compound A. Human PBL were purified using standard procedures and incubated for 24 hour in medium alone or in the presence of a TLR3 ligand (poly dI:dC, 20 µg/ml) or a TLR4 ligand (LPS, 0.2 µg/ml). Compound A was added to the various cultures at the indicated concentrations. After 24 hours the monocytes were purified using anti-CD14-conjugated magnetic beads and used as stimulators in an MLR reaction. Four days after the initiation of the cultures the cell populations were analysed using FACS.

Knowing that TOLL stimulation increased the surface expression of S100A9 on human monocytes in vitro it was of interest to address whether blockade of S100A9 could have any functional consequence on human monocytes. To this end we designed an in vitro assay, FIG. 10.

Figure 11:
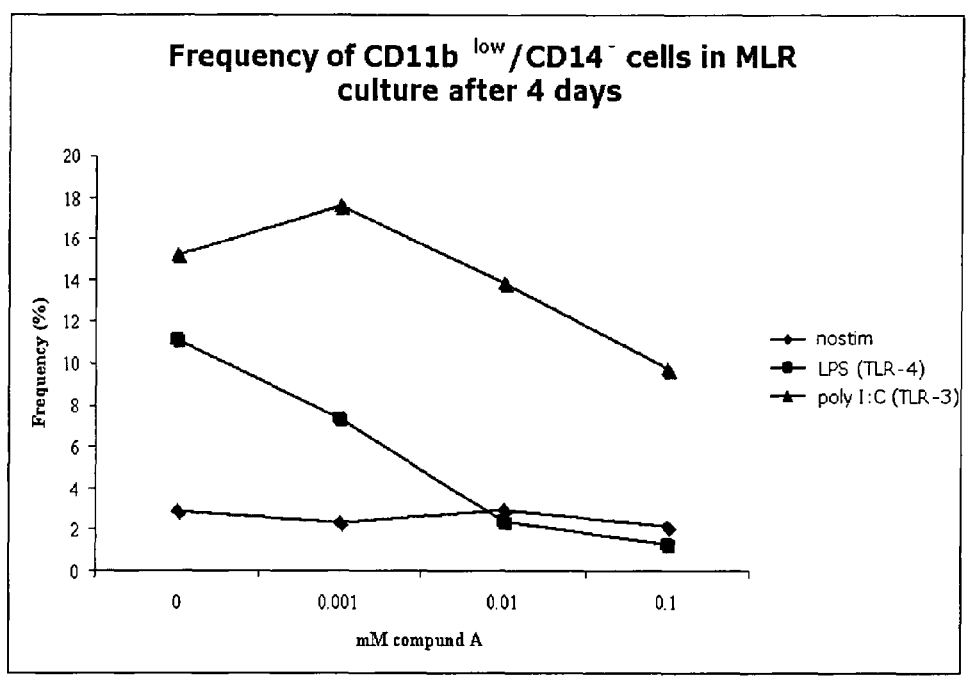
FIG. 11 concerns a TOLL-induced MLR cell population. A specific, TOLL-induced MLR cell population is selectively diminished by the addition of S100A9-binding compounds to the pre-cultures. The frequency of a defined $CD11^{blow}CD14^-$ cell population that emerges in MLR cultures only when TOLL stimulated $CD14^+$ cells have been used as stimulators is dose-dependently reduced when S100A9 binding compound has been added to the pre-cultures.

FIG. 11 shows an example of such analysis. We have noted that in the

MLR reactions using TOLL-stimulated monocytes as stimulators cells, a specific cell population could be detected after 4 days. This cell population was CD11b$^{low}$ and CD14$^-$ as determined by FACS analysis. If the stimulator cells were pre-incubated in medium only, this population did not appear (FIG. 11). Addition of a S100A9 binding compound to the preincubation cultures at the indicated concentrations reduced the percentage of CD11b$^{low}$CD14$^-$ cells in the MLR reaction in a dose-dependent fashion. This was true independently of whether the pre-incubation cultures had been stimulated with a TLR3 or a TLR4 ligand. Hence, this simple in vitro assay can be used to functionally assess S100A9 binding compounds influence on biological function in vitro.

The MLR assay is described in Bach & Hirschhorn (1964), Science 143, 813.

In vitro Assay for S100A9 binding Compounds Modulating TOLL-dependent Stimulation of Human PBMC Human PBMC were incubated over night in medium only or together with a TLR4 ligand (LPS) or a TLR3 ligand (polidI:dC). After this pre-incubation period, monocytes were purified based on their CD14 expression using magnetic beads coated with anti-CD14 antibodies. These CD14 cells were in turn used as stimulators in a Mixed Lymphocyte Reaction (MLR) with PBMC from an allogeneic donor. After 4 days the MLR reaction can be analysed using various methods.

Treatment with S100A9 Binding Compounds has Effects on Dendritic Cell Populations in Human blood.

Figure 12:
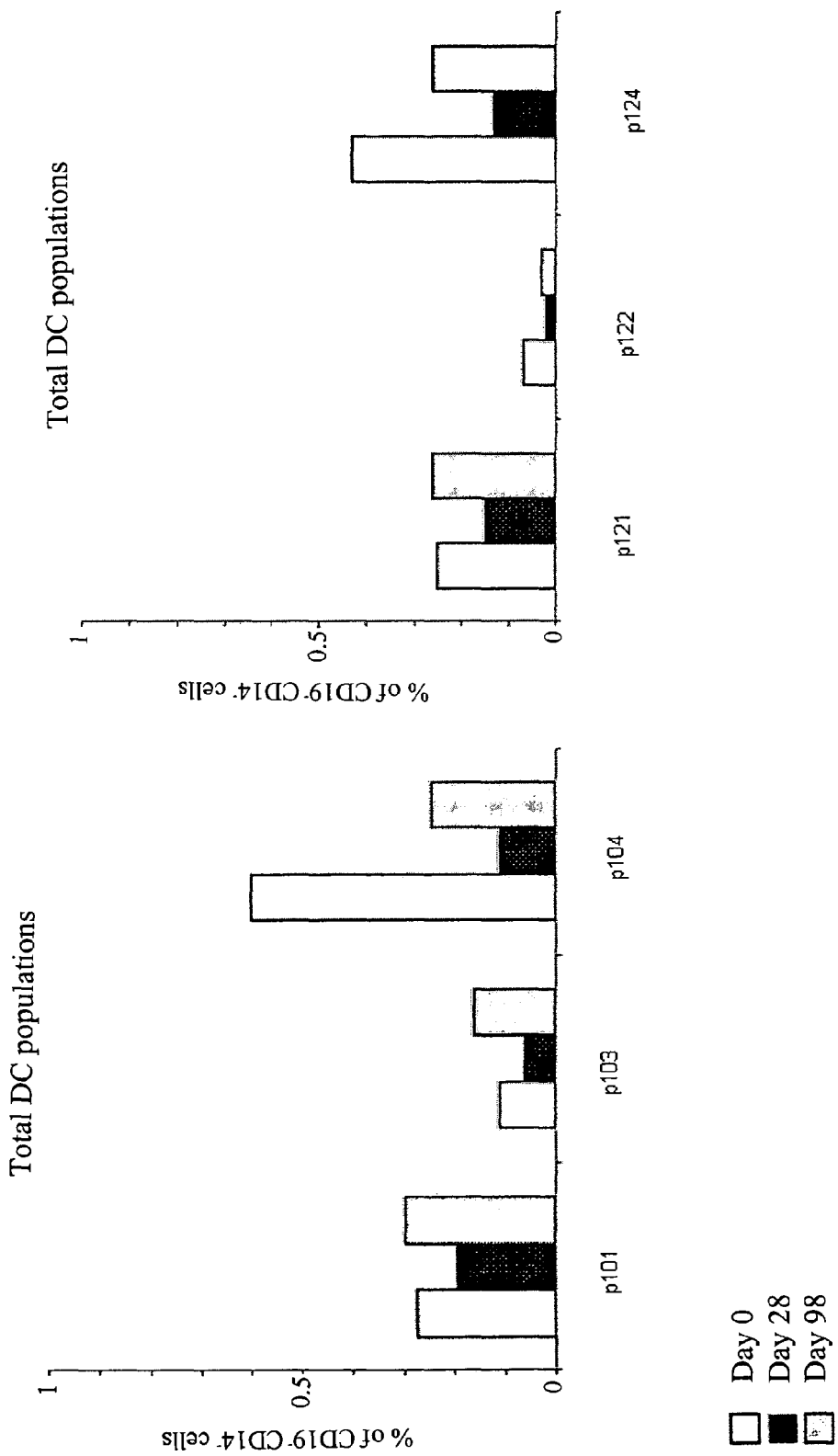
FIG. 12 shows total DC population are reduced in human SLE patients. Total DC populations are reduced in human SLE patients treated with S100A9 binding compound. SLE patients treated with 1.5 mg/day (left panel) or 3 mg/day (right panel) have a reversible downregulation of total blood DC as determined by FACS analysis. Day 0 represents baseline values before dosing, day 28 the patients are at steady-state and day 98 the patients have been withdrawn from treatment for 14 days.
Figure 13:
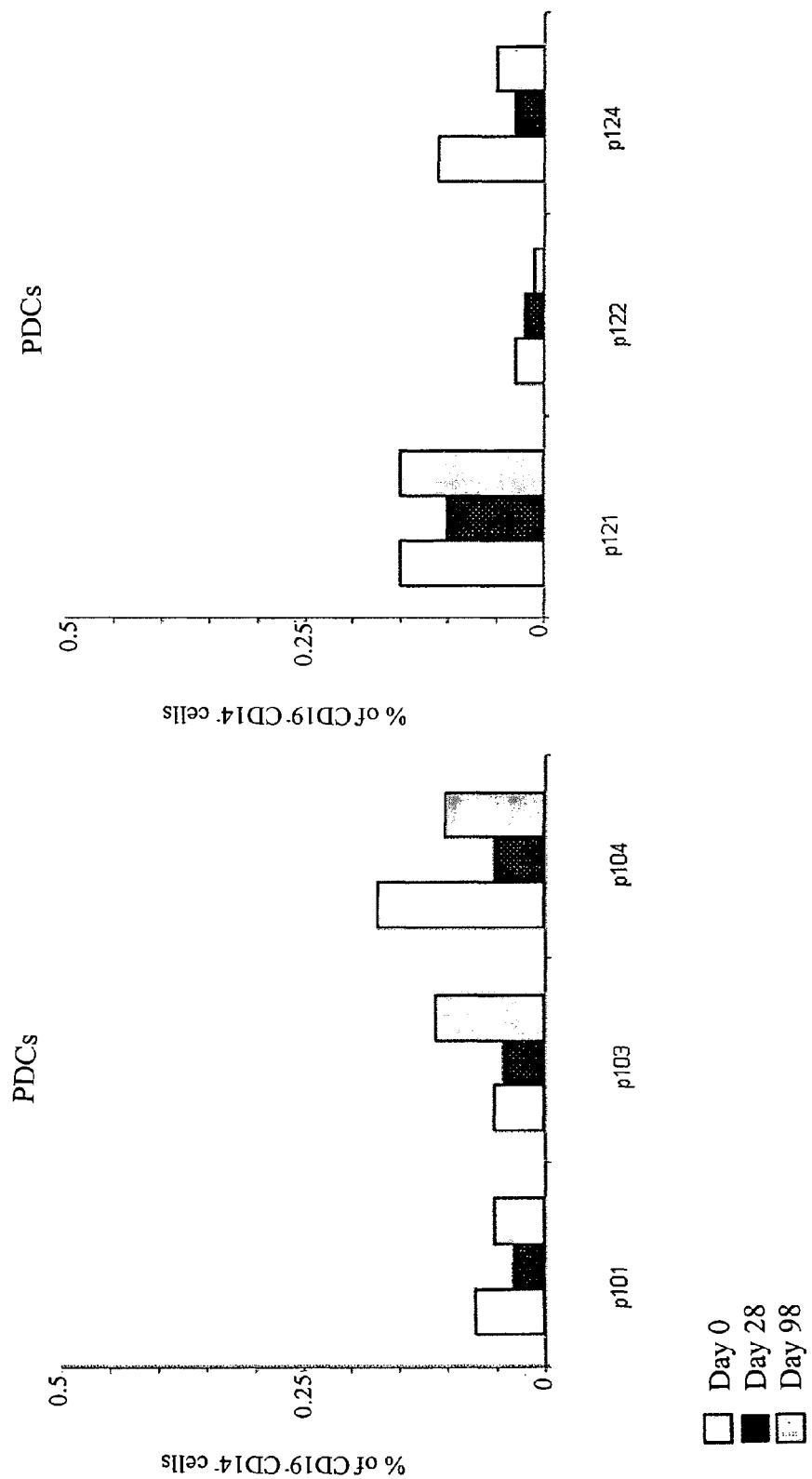
FIG. 13 shows plasmacytoid DC populations are reduced in human SLE patients treated with S100A9 binding compound. SLE patients treated with 1.5 mg/day (left panel) or 3 mg/day (right panel) have a reversible downregulation of blood plasmacytoid DC as determined by FACS analysis. Day 0 represents base-line values before dosing, day 28 the patients are at steady-state and day 98 the patients have been withdrawn from treatment for 14 days.

Human monocytes belong to a cell type that is usually referred to as Antigen Presenting Cells (APC). The monocytes can, upon proper stimulation, exit the blood stream into tissues and coupled to this process is their differentiation into distinct cellular phenotypes such as macrophages and dendritic cells (DC). DC are also found circulating in the blood stream and can be further subdivided based on surface markers. DC are also regarded as the major immunoregulatory type of APC. It was therefore of interest to investigate whether treatment of human subjects with S100A9 binding compound influenced the levels of DC in the blood. We here took advantage of an ongoing Phase Ib study where SLE patients are treated with compound A, a S100A9 binding compound. Blood samples from the patients were taken before treatment (Day 0), at steady-state one month after treatment (day 28) and two weeks after treatment was stopped (Day 98). Two dose group of three patients each were available for analysis; 1.5 mg/day and 3 mg/day. PBMCs were analysed at these times for the presence of totals DC (FIG. 12) and plasmacytoid DC (FIG. 13). As can be seen in FIGS. 15 and 16, both the percentage of total DC and of plasmacytoid DC were reduced when the patients were under treatment with compound A compared to pre- and post-treatment levels. Thus, treatment of humans with S100A9 binding compounds has an effect on APC in vivo.

Materials and Methods

Compound A

The compound A was synthesized according to the methods disclosed in U.S. Pat. No. 6,077,851. Compound A is described in formula (I) of FIG. 1 of the document.

Biosensor Analysis

Binding analysis was performed using the "surface plasmon resonance" (SPR) technology with a Biacore 3000™ system. This technology allows analysis of an interaction between proteins and small molecules in a real-time and label-free manner. A protein or low-molecular weight compound is injected over a surface (a CM5 sensor chip) with a covalently coupled ligand and the signal produced, expressed as resonance units (RU), is directly proportional to the number and mass of the molecule interacting with the ligand on the surface. Immobilization, regeneration scouting, surface performance tests and binding studies were conducted basically according to the instructions by the manufacturer. Kinetic evaluation of binding data was carried using the BIAevaluation Software Version 3.2 (Biacore AB). Optimization of conditions for immobilization and binding analysis is carried out for each interaction to be studied. A biosensor analysis cycle consists of: (i) injection of S100A9 over the RAGE surface for 3 min (association phase) or (i) injection of S100A9 over the TLR4/MD-2 surfaces, in the absence or presence of 100 ng/mL LPS, for 3 min (association phase); (ii) injection of running buffer for 2.5 min (dissociation phase); (iii) injection of a 30 s pulse of 10 mM glycine-HCl, pH 2.0-2.125 (regeneration phase); and (iv) injection of running buffer for 2 min (stabilization after regeneration) at a flow rate of 30 µl/min.

Identity and homogeneity of S100 proteins were tested on SDS-PAGE.

Immobilization of RAGE

Recombinant human RAGE was obtained from R&D Systems (cat. No. 1145-RG) as a fusion protein of the extracellular domain of RAGE, comprising a.a. 1-344, and the Fc region of human IgG$_1$ via a peptide linker. The chimeric protein was expressed in the mouse myleoma cell line NSO as a disulfide-linked homo-dimeric protein with a calculated molecular mass of 61 kDa. Prior to covalent coupling to the sensor chip, buffer was changed to a standard Biacore buffer (10 mM Hepes, 0.15 M NaCl, pH 7.4, containing 0.005% v/v Surfactant P20; HBS-P) using Fast Protein Desalting Micro-Spin Columns (Pierce). RAGE was diluted in an immobilization buffer shown to give sufficient pre-concentration and then covalently coupled using the "Aim at immobilization level" function in the Biacore Wizard to obtain various coupling densities. Activity of immobilized RAGE was tested by injecting a specific anti-human RAGE monoclonal antibody over the surface. Due to extensive glycosylation of RAGE relative to that of the Fc domain and a higher mass of the latter, it was also assumed that chimeric RAGE/Fc will be coupled predominantly via the Fc domain and result in a semi-oriented coupling to the sensor chip. HBS-P, with a final concentration of 1 mM CaCl$_2$ and 10 µM ZnCl$_2$, was used as sample and running buffer throughout the study. For regeneration of the surface after each cycle, a pulse of 10 mM glycine-HCl, pH 2.125, was used. To determine optimal zinc concentration for binding of S100A9 protein to RAGE, the interaction was allowed to take place at a fixed calcium concentration (1 mM) and with the zinc concentration titrated from zero to ten µM.

Interaction of Soluble S100A9 with the RAGE Surface

Recombinant S100A9, expressed as the full-length sequence of native protein in *E. coli* was obtained using a four-step purification protocol. Purity was checked on overloaded SDS-PAGE gels and found to be >95% homogeneous. Buffer was changed to HBS-P using the Fast Protein Desalting Spin Columns and concentration determined in the BCA protein assay from Pierce with bovine albumin as standard. A 10 µM stock solution based on the homodimeric molecular weight of S100A9 was prepared and stored in aliquots frozen at −25° C. From this, a working solution of 1000 nM in HBS-P was prepared and diluted to the concentration to be tested with ZnCl$_2$ and CaCl$_2$ added to a final concentration of 10 µM Zn$^{2+}$ and 250 or 1000 µM Ca$^{2+}$ according to the buffer system proposed by Robinson et al. (2002).

Immobilization of TLR4/MD-2 Complex

Recombinant human TLR4/MD-2 was obtained from R&D Systems (cat. no. 3146-TN/CF) as a non-covalently associated protein of the respective extracellular domains. Prior to covalent coupling to the sensor chip, buffer was changed to a standard Biacore buffer (10 mM Hepes, 0.15 M NaCl, pH 7.4, containing 0.005% v/v Surfactant P20; HBS-P) using Fast Protein Desalting Micro-Spin Columns (Pierce).

The human recombinant TLR4 amino acid sequence consists of human CD33 Signal peptide (Met 1-Ala 16), human TLR4 (Glu 24-Lys 631), and 10× histidines. The chimeric protein was expressed in a mouse myeloma cell line, NSO.

The human recombinant MD-2, amino acid sequence consists of human human CD33 Signal peptide (Met 1-Ala 16), human MD-2 (Glu 17-ASN 160), and 10× histidines. The chimeric protein was expressed in a mouse myeloma cell line, NSO.

Interaction of Soluble S100A9 with the TLFR4/MD-2 Surface

Recombinant S100A9, expressed as the full-length sequence of native protein in *E. coli* was obtained using a four-step purification protocol. Purity was checked on overloaded SDS-PAGE gels and found to be >95% homogeneous. Buffer was changed to HBS-P using the Fast Protein Desalting Spin Columns and concentration determined in the BCA protein assay from Pierce with bovine albumin as standard. A 10 μM stock solution based on the homodimeric molecular weight of S100A9 was prepared and stored in aliquots frozen at −25° C. From this, a working solution of 1000 nM in HBS-P was prepared and diluted to the concentration to be tested with $ZnCl_2$ and $CaCl_2$ added to a final concentration of 10 μM $Zn^{2+}$ and 250 or 1000 μM $Ca^{2+}$ according to the buffer system proposed by Robinson et al. (2002).

Competition Assay

In order to analyze compounds as potential inhibitors of the S100A9—RAGE interaction, S100A9 was injected over the RAGE surface in the absence or presence of serially diluted compound. Compounds were dissolved either directly as a 2 mM solution in HBS-P or in double-distilled water at 5 or 10 mM concentration and stored in aliquots at −25° C. In the latter case, compounds were diluted to a 2 mM working solution by adding 10% v/v 100 mM Hepes, 1.5 M NaCl, pH 7.4, 0.05 v/v Surfactant P20. Biomolecules known to interact with S100A9 in a calcium-dependent manner and with an affinity in the low nanomolar range are glycosaminoglycans like heparin and heparan sulfate (Robinson et al., 2002). Therefore, heparin and heparan sulfate were used as positive controls in the assay to test their ability to inhibit the S100A9 interaction with immobilized RAGE.

Evaluation of Binding Data

Binding data was evaluated by fitting to standard binding models, where appropriate, or calculation of response at late association phase using Steady state affinity function using the BIAevaluation Software version 3.2. Affinity was determined either from kinetic analysis (on- and off-rates) or from plotting of responses versus concentration of S100A9 in a saturation curve. In the inhibition assay format, the concentration of competitor yielding 50% inhibition of S100A9 bound in the absence of competitor ($IC_{50}$ value) was calculated by fitting binding data to a one-site competition model in GraphPad Prism or after log-logit transformation of data and linear regression.

Purification of Splenic DCs and Human PBMCs

Spleens and lymph nodes from treated and untreated mice were cut into small pieces and treated with collagenase and DNA:ase to release the DCs from the tissue. The DCs were positively selected using CD11c-magnetic microbeads. Human PBMCs were isolated from whole blood using gradient centrifugation.

MLR Reactions

Human PBMCs were cultured in vitro over night in tissue culture medium. The cells were either activated by the TLR ligands LPS or poly I-C or not activated. Various concentrations of compound A was added to parallel cultures. After the over night culture CD14-positive cells were purified using CD14-magnetic beads. These cells were γ-irradiated and used as stimulator cells in the MLR-reaction. From another donor, CD4-positive cells were purified using CD4-magnetic beads. The proliferation of the responder T cells was determined on day 4 of culture by measuring incorporation of $^3$H-thymidine.

Analysis of Cell Subsets by Flow Cytometry

Collagenase/DNAse-treated spleen or lymph node cell suspensions or purified DCs were blocked with anti-Fc mAb and stained with the following fluorescently labeled antibodies: CD11c, CD4 and CD8. Human PBMCs or cells from MLR-reactions were stained with the following fluorescently labeled antibodies: CD11b, CD14 and S100A8/A9. Stained cells were analysed by flow cytometry. Dead cells were excluded using 7-actinomycin D Autoimmune Disease Models Compound A shows a dose dependent inhibition of disease induction in several animal models of autoimmune disease. Compound A is suitable for use in the clinical treatment of diseases resulting from pathologic inflammation and autoimmunity, e.g., systemic lupus erythematosus (SLE), insulin-dependent diabetes mellitus (IDDM), collagen induced arthritis (CIA), multiple sclerosis (MS) and rheumatoid arthritis (RA). Compound A inhibits disease in a spontaneous animal model for systemic lupus erythematosus (SLE) in MRL lpr/lpr mice, in a spontaneous model for type I diabetes in nonobese diabetic (NOD) mice and in an induced model for multiple sclerosis, i.e., acute experimental autoimmune encephalomyelitis (aEAE) induced by immunization with spinal cord homogenate (Table 1). All these models have been the most widely used models for the human diseases.

Experimental Lupus Model in MRL lpr/lpr Mice

The MRL lpr/lpr mouse spontaneously develops an autoimmune disease resembling human SLE. The SLE-like disease in these mice is characterized by immune complex-mediated glomerulonephritis measured as proteinuria and hematuria, enlargement of spleen and lymph nodes and production of anti-double stranded DNA (dsDNA) antibodies. Clinical signs can be detected at approximately 8 weeks of age. The main cause of death in these mice is renal failure. The mice were used for experiments from the age of 14-15 weeks. The development of glomerulonephritis measured as proteinuria and hematuria was followed. The mice were sacrificed after development of full SLE-like disease. Percent survival was calculated at the end of the experiment when the mice had reached the age of 23-24 weeks. Compound A (1 or 5 mg/kg/day) was administered in drinking water from 14-15 weeks and throughout the experiment.

The Nonobese Diabetic (NOD) Mouse Model for Autoimmune Insulin-dependent Diabetes Mellitus (IDDM)

The NOD mouse spontaneously develops autoimmune IDDM and serves as an animal model for the human type I diabetes. NOD mice start to develop clinical symptoms of diabetes at 14-16 weeks of age. Mice were used in experiments from the age of 10 weeks. The development of overt diabetes was evaluated by measuring the existence of glucose in urine. If positive for glucose in urine, the animals were scored diabetic and sacrificed. Treatment with compound A (0.008, 0.04, 0.2, 1 or 5 mg/kg/day) was administered in the drinking water from 10 weeks to 26 weeks of age. Treatment with compound A (1 or 5 mg/kg/day) was administered in the drinking water from 5 weeks to 12 weeks of age.

Acute Experimental Autoimmune Encephalomyelitis (aEAE) Model

EAE is a murine model for autoimmune inflammatory disease of the central nervous system. EAE in the mouse shares many features with the human disease multiple sclerosis. SJL/N female mice were used for the experiments. Complete Freund's adjuvant containing H37Ra mycobacteria was emulsified with an equal volume of mouse spinal cord homogenate (MSCH). The inoculum was injected intradermally at the base of the base of the tail. Pertussis toxin was injected i.p. at day 0 and 3 after immunization. The disability symptoms appear about eight days post immunization (p.i.) and peaks around 12 days p.i. Treatment with compound A (0.04, 0.2 or 1 mg/kg/day) was given at days 3 to 7 and 10 to 12 p.i. Control animals received saline. The animals were scored for clinical signs of paralytic disease on a scale from 0 to 5 in the following way; 0, normal; 1, limp tail; 2, hind limb paresis; 3, hind limb paralysis, and limp foreleg; 4, bilateral hind and fore limb paralysis; 5 death. Clinical scores were monitored daily from day 9 until the end of the experiment at day 14. Treatment effects were calculated as percent inhibition of mean clinical scores compared to saline treated controls.

TABLE 1

Survival (%), MRL lpr/lpr model of SLE

| Treatment | Number of mice - start | Number of mice - end | % Survival at 22-23 weeks of age |
|---|---|---|---|
| Control | 7 | 1 | 14% |
| Compound A (1 mg/kg/day) | 7 | 6 | 86% |
| Compound A (5 mg/kg/day) | 5 | 5 | 100% |

Diabetic mice (%), NOD model of IDDM

| Treatment | Dose (mg/kg/day) | % Diabetic Mice at 26 weeks of age |
|---|---|---|
| Control | — | 80% |
| Compound A | 0.008 | 70% |
| Compound A | 0.04 | 50% |
| Compound A | 0.2 | 15% |
| Compound A | 1 | 0% |
| Compound A | 5 | 0% |

Disease inhibition(%), aEAE model in SJL mice

| Treatment | Dose (mg/kg/day) | Mean % inhibition |
|---|---|---|
| Compound A | 0.04 | 46 |
| Compound A | 0.20 | 75 |
| Compound A | 1 | 98 |

Generation of Anti-S100A9 Monoclonal Antibody 43/8

A 10 week old C57BL/6 mouse with an inactivated S100A9 gene was immunized intraperitoneally with 100 µg recombinant S100A9 protein precipitated with alum. Six weeks later the animal was boosted with the identical antigen using the same procedure. Three days after boosting the spleen was removed and fused to SP2/0 cells using a standard protocol. Stable hybridomas were selected using HAT selection. Hybridomas were screened using an ELISA were the recombinant S100A9 was used as the coating antigen and antibody reactions were revealed using an enzyme-coupled rabbit-anti mouse antibody followed by interaction with substrate giving rise to a color reaction. Positive hybridomas were cloned using limiting dilution and a clonal cell line isolated at dilutions where only single cell progeny can be expected based on Poisson statistics.

BIACORE™ Assays Demonstrates the Binding Ability of the Anti-S100A9 mAb 43/8

The binding of human and murine S100A8, S100A9 and S100A8/S100A9 complex to the anti-S100A9 mAb 43/8 was demonstrated by BIACORE™ direct binding assay. Assays were performed using the anti-S100A9 mAb 43/8 coated on a CM5 chip at high density (3000 RU) using standard amine coupling. The S100A8 and S100A9 proteins were injected at 100 nM concentration (based on the homo- or hetero-dimeric molecular weight) for 3 min at a flow rate of 30 µl/min in sample buffer (HBS-P buffer containing 1 mM $Ca^{2+}$ and 20 µM $Zn^{2+}$) (1; association phase) followed by injection of running buffer (same as sample buffer) at (2; dissociation phase). Binding was demonstrated for the human and murine proteins, S100A8, S100A9 and the S100A8/S100A9 complex, to the anti-S100A9 mAb 43/8. The binding of the S100A8 and S100A9 proteins to the anti-S100A9 mAb 43/8 was dependent on the metal ions $Zn^{2+}$ and $Ca^{2+}$. Binding was assayed in absence and presence of 1 mM $Ca^{2+}$ and 20 µM $Zn^{2+}$. It was shown that the presence of both these metal ions were required for binding to the anti-S100A9 mAb 43/8. Responses were calculated at late association phase in the absence or presence of 1 mM $Ca^{2+}$ and 20 µM $Zn^{2+}$ in HBS-P. The other conditions were as stated above.

The Anti-S100A9 mAb 43/8 is Specific to Human S100A9

Various S100 proteins were assayed for binding to immobilized anti-S100A9 mAb 43/8 at 100 nM and in the presence of $Ca^{2+}$ and $Zn^{2+}$ by BIACORE™ direct binding assay. Specificity for human S100A9 by the antibody was demonstrated. The anti-S100A9 antibody show, in addition to reactivity towards the human S100A8/S100A9 complex, human S100A12 and the murine S100A8/S100A9 complex, only weak or no reactivity for the other assayed human and murine S100 proteins.

Samples were injected for 2 min at 30 µl/min over amine coupled anti-S100A9 mAb 43/8 at a density of ~3,000 RU. Responses at late association phase (t~175 s) were calculated using the steady-state affinity model in BIAevaluation. S100 proteins to be analyzed were applied on Fast Protein Desalting Columns to obtain a stock solution of 10 µM protein in HBS-P buffer. Recombinant human S100β, S100A6, S100A1 and S100A11 were obtained from ProSpec Techno-Gene, Rehovat, Israel; S100A10 and annexin 2 (calpactin light and heavy chain), with an amino-terminal $His_6$-tag, from Randox Laboratories Ltd, Antrim, UK; human recombinant S100A4 from Assay Designs, Inc, Ann Arbor, Mich., USA; human S100AB (αβ heterodimer) was from Research Diagnostics, Inc, Concord, Mass., USA; and human recombinant S100P from BioVendor Laboratory Medicine, Inc, Brno, Czech Republic. Human and murine S100A8, S100A9 and S100A8/9 were either produced recombinantly in E. coli (rhS100A9) by us, or were obtained from elsewhere. S100A12 was purified from human granulocytes.

The Anti-S100A9 mAb 43/8 blocks Binding of Human S100A9 to RAGE

The anti-S100A9 antibody's ability to block the binding of human S100A9 to human RAGE was measured by BIACORE™ direct binding assay. The assay was performed by coating human RAGE on a standard CM5 chip at high density (3000 RU) using standard amine coupling. S100A9, with or without mAb 43/8, was injected at 100 nM concentration for 3 min at a flow rate of 30 µl/min in sample buffer (HBS-P buffer containing 1 mM $Ca^{2+}$ and 20 µM $Zn^{2+}$) (1; association phase) followed by injection of sample buffer (2; dissociation phase).

Responses at late association phase, obtained after injection of 100 nM S100A9, pre-incubated for at least 1 h at room temperature ±12.5-500 nM anti-S100A9 mAb 43/8, over immobilized RAGE were plotted versus concentration of anti-S100A9 antibody. After log-logit transformation of binding data 50% inhibition of S100A9 binding ($IC_{50}$) was calculated to $3.4 \times 10^{-8}$ M ($r^2$ 0.98).

The Anti-S100A9 mAb 43/8 Blocks Binding of Human S100A9 to TLR4/MD-2

The anti-S100A9 mAb 43/8 ability to block the binding of human S100A9 to human TLR4/MD-2 complex was measured by BIACORE™ direct binding assay. The assay was performed by coating human TLR4/MD-2 complex on a CM5 chip at a density of ~3000 RU using standard amine coupling. Human S100A9 was injected at 100 nM with or without mAb 43/8 for 3 min at a flow rate of 30 ηl/min in sample buffer (HBS-P buffer containing 1 mM $Ca^{2+}$ and 20 μM $Zn^{2+}$) (1; association phase) followed by injection of sample buffer (2; dissociation phase).

Responses at late association phase, obtained after injection of 100 nM S100A9, pre-incubated for at least 1 h at room temperature ±12.5-500 nM anti-S100A9 mAb 43/8, over immobilized TLR4/MD-2 complex were plotted versus concentration of anti-S100A9 antibody. Binding data were transformed to a log-logit plot for calculation of the $IC_{50}$ value yielding 50% inhibition at $2.7 \times 10^{-8}$ M ($r^2$ 0.91).

The Anti-S100A9 mAb 43/8 Blocks binding of Human S100A9 to Amino-linked Compound A The anti-S100A9 mAb 43/8 ability to block the binding of human S100A9 to amino-linked Compound A was measured by BIACORE™ direct binding assay. The assay was performed by coating amino-linked Compound A on a CM5 chip using standard amine coupling. S100A9 at 100 nM was injected over immobilized Compound A in the absence or presence of mAb 43/8 for 3 min at a flow rate of 30 μl/min in sample buffer (HBS-P buffer containing 1 mM $Ca^{2+}$ and 20 μM $Zn^{2+}$) (1; association phase), followed by injection of sample buffer (2; dissociation phase).

Responses at late association phase, obtained after injection of 100 nM S100A9, pre-incubated for at least 1 h at room temperature ±12.5-500 nM monoclonal anti-S100A9 antibody, over immobilized Compound A were plotted versus concentration of anti-S100A9 antibody. Binding data were transformed to a log-logit plot (D) for calculation of The $IC_{50}$ value was obtained after log-logit transformation of binding data yielding 50% inhibition at $12 \times 10^{-8}$ M ($r^2$ 0.96).

The Anti-S100A9 Antibody Recognizes a Unique Epitope

The anti-S100A9 mAb 43/8 recognizes an epitope different to that of the 1C10 anti-human S100A9 antibody. The blocking of S100A9 binding to immobilized anti-S100A9 antibody in the presence of $Ca^{2+}$ and $Zn^{2+}$ by the anti-S100A9 antibodies in solution was measured by BIACORE™ direct binding assay. S100A9, pre-incubated either with anti-S100A9 antibody 43/8 or 1C10, was injected over immobilized anti-S100A9 antibody 43/8. Pre-incubation with antibody 43/8 resulted in a more than ten-fold higher inhibition of S100A9 binding to immobilized 43/8 than for antibody 1C10.

The assay was performed by coating the mouse anti-S100A9 monoclonal antibody 43/8 on a CM5 chip at high density (3000 RU) using standard amine coupling. Human S100A9, at a concentration of 100 nM, was pre-incubated for at least one hour with either antibody 43/8 or 1C10 in the concentration range 0-400 nM in sample buffer (HBS-P buffer containing 1 mM $Ca^{2+}$ and 20 μM $Zn^{2+}$). Incubated samples were then injected for 3 min at a flow rate of 30 μl/min (1; association phase) followed by injection of sample buffer (2; dissociation phase). Responses were calculated at late association phase. The mouse anti-human S100A9 monoclonal antibody 1 C 10 was purchased from Nordic Biosite.

The Anti-S100A9 mAb 43/8 Interacts with the Surface of Human Monocytes

Human Peripheral Blood Mononuclear Cells (PBMCs) were incubated with the anti-S100A9 mAb 43/8 antibody, the anti S100A8/A9 antibody 27E10 or an isotype control antibody for 30 min at 4° C. Cell-associated fluorescence signals were measured by using a FACScan flow cytofluorometer. The anti-S100A9 mAb 43/8 could be seen to interact with the surface of human monocytes but with lower efficiency than the 27E10 antibody. The isotype control antibody did not give any staining over back-ground.

The Anti-S100A9 mAb 43/8 Stimulates TNFα-production in Peripheral Blood Mononuclear Cells To test whether the anti-S100A9 mAb 43/8 had functional properties freshly prepared monocytes from human peripheral blood was incubated with 10 μg/ml 43/8 for 24 hours. As a control, cells were incubated with medium alone (negative control), 10 μg/ml of an isotype matched antibody (negative control) or 0.5 μg/ml lipopolysaccharide (LPS) as a positive control. It was observed that the 43/8 antibody induced a robust TNFα production from human peripheral blood monocytes. This data shows that the anti-S100A9 mAb 43/8 has a unique ability to induce a transmembrane signal into human monocytes that's leads to a pro-inflammatory response.

The Anti-S100A9 mAb 43/8 Stimulates an NFκB Reporter Gene in LNCaP Cells

The human prostate cancer cell line LNCaP express RAGE and one of its known protein ligands S100A9. The anti-S100A9 mAb 43/8 induced expression of an NFκB reporter gene transfected (pLR446) into the LNCaP cells. Triplicate cell cultures with $10 \times 10^4$ cells (96 well plate) were incubated for 4 h at 37° C. in 100 μl RPMI culture medium supplemented with 10% FCS and 10 μM $Zn^{2+}$, before the luminescence was measured (Steadylite HTS; Perkin Elmer). PMA (1.5 ng/ml) was used as a positive control and as a negative isotype control mouse IgG1 was used. The data shows that the anti-S100A9 mAb 43/8 induced NFκB reporter gene activity in a dose dependent way via a transmembrane signal.

Conclusion

The anti-S100A9 monoclonal antibody of the present invention specifically binds S100A9. It is capable of modulating the interactions of S100A9 to RAGE, S100A9 to TLR4, and S100A9 to Compound A. Further, the anti-S100A9 antibody demonstrates the novel and unexpected ability of inducing transmembrane signalling into human cells that leads to a pro-inflammatory response.

Compound A is an Efficient Modulator of S100A9 Binding to RAGE and TLR4

The ability of Compound A to modulate the interactions of human S100A9 to RAGE, and to TLR4/MD-2, was compared to the substance Rolipram, (Sommer et al., Nature Medicine, vol. I, no. 3, 244-248, 1995). Rolipram is a selective inhibitor of phosphodiesterase type IV and has been shown to be effective in treatment of animal model experimental autoimmune encephalomyelitis EAE. Rolipram, (+/−)-4-(3-cyclopentyloxy-4-methoxyphenyl)-2-pyrrolidone, is of a different chemical class to that of Compound A.

The binding of S100A9 to immobilized RAGE, TLR41MD-2 or Compound A, was assayed in presence of Compound A and Rolipram. Compound A displayed a significantly higher inhibition of the assayed interactions than Rolipram.

Samples were injected for 3 min at 30 μl/min in HBS-P buffer over amine coupled RAGE, TLR4/MD-2 and Compound A. Binding +/− competitor was calculated as response at late association phase or by fit of sensorgrams to a 1:1 Langmuir model. IC50 values were calculated by fitting data to a sigmoidal dose-response (variable slope) model in Graph-Pad Prism.

TABLE 2

Summary of binding data.

| Immobilized ligand; Parameter | Compound A | Rolipram | Relative index IC$_{50}$(Rolipram): IC$_{50}$(Compound A) |
|---|---|---|---|
| RAGE; IC$_{50}$ (μM) | 73.5 | 399 | 5.4:1 |
| TLR4/MD-2; IC$_{50}$ (μM) | 81.1 | 458 | 5.7:1 |
| Compound A; IC$_{50}$ (μM) | 75.7 | 873 | 11.5:1 |

Data was fit to sigmoidal dose-response (with variable slope) model in GraphPad Prism.

The invention claimed is:

1. An antibody that specifically binds to an epitope on S100A9 which epitope is present on a region of S100A9 that binds to TLR4 and RAGE, wherein the antibody comprises 43/8.

2. The antibody according to claim 1 which is capable of:
   (i) inhibiting the binding of S100A9 to TLR4 and RAGE, and
   (ii) stimulating TNFα production in monocytes.

3. The antibody according to claim 1 which is obtainable by immunizing an S100A9 null mouse with S100A9.

4. The antibody according to claim 1 comprising an epitope binding fragment.

5. The antibody according to claim 4 comprising epitope binding fragments consisting of Fv, F(ab'), or F(ab')$_2$.

6. The antibody according to claim 1 comprising an epitope binding single chain antibody.

7. The antibody according to claim 6 comprising an epitope binding fragment.

8. The antibody according to claim 7 comprising epitope binding fragments consisting of Fv, F(ab'), or F(ab')$_2$.

9. The antibody according to claim 1 wherein the antibody recognizes a unique epitope on the S100A9 molecule, wherein the epitope overlaps with the region of the S100A9 molecule that can interact with TLR4 and RAGE.

10. The antibody according to claim 1 wherein the interaction of the antibody with S100A9 is dependent on the presence of $Ca^{2+}$ and $Zn^{2+}$ in the S100A9 protein.

* * * * *